US011062789B2

United States Patent
Chiu et al.

(10) Patent No.: US 11,062,789 B2
(45) Date of Patent: Jul. 13, 2021

(54) METHYLATION PATTERN ANALYSIS OF TISSUES IN A DNA MIXTURE

(71) Applicant: The Chinese University of Hong Kong, Shatin (CN)

(72) Inventors: Rossa Wai Kwun Chiu, Shatin (CN); Kwan Chee Chan, Mei Foo Sun Chuen (CN); Yuk-Ming Dennis Lo, Homantin (CN); Peiyong Jiang, Shatin (CN); Kun Sun, Shatin (CN)

(73) Assignee: The Chinese University of Hong Kong, New Territories (HK)

( * ) Notice: Subject to any disclaimer, the term of this patent is extended or adjusted under 35 U.S.C. 154(b) by 1040 days.

(21) Appl. No.: 14/803,692

(22) Filed: Jul. 20, 2015

(65) Prior Publication Data

US 2016/0017419 A1  Jan. 21, 2016

Related U.S. Application Data

(60) Provisional application No. 62/183,669, filed on Jun. 23, 2015, provisional application No. 62/158,466, (Continued)

(51) Int. Cl.
 *G16B 20/00* (2019.01)
 *C12Q 1/6809* (2018.01)
 (Continued)

(52) U.S. Cl.
 CPC .......... *G16B 20/00* (2019.02); *C12Q 1/6809* (2013.01); *C12Q 1/689* (2013.01); *G16B 20/10* (2019.02); *G16B 30/00* (2019.02)

(58) Field of Classification Search
 None
 See application file for complete search history.

(56) References Cited

U.S. PATENT DOCUMENTS 6,773,897 B2   8/2004  Herman et al.
7,749,702 B2   7/2010  Lofton-Day et al.
(Continued)

FOREIGN PATENT DOCUMENTS

CN   102021233 A   4/2011
CN   102105586 A   6/2011
(Continued)

OTHER PUBLICATIONS

MM Gil et al. Analysis of cell-free DNA in maternal blood screening for fetal aneuploidies: updated meta-analysis. Ultrasound Obstet Gynecol Feb. 1, 2015, vol. 45, p. 249-266 (Year: 2015).*
(Continued)

*Primary Examiner* — Olivia M. Wise
(74) *Attorney, Agent, or Firm* — Kilpatrick Townsend & Stockton LLP

(57) ABSTRACT

The contributions of different tissues to a DNA mixture are determined using methylation levels at particular genomic sites. Tissue-specific methylation levels of M tissue types can be used to deconvolve mixture methylation levels measured in the DNA mixture, to determine fraction contributions of each of the M tissue types. Various types of genomic sites can be chosen to have particular properties across tissue types and across individuals, so as to provide increased accuracy in determining contributions of the various tissue types. The fractional contributions can be used to detect abnormal contributions of a particular tissue, indicating a disease state for the tissue. A differential in fractional contributions for different sizes of DNA fragments can also be used to identify a diseased state of a particular tissue. A sequence imbalance for a particular chromosomal region can be detected in a particular tissue, e.g., identifying a location of a tumor.

48 Claims, 41 Drawing Sheets

(8 of 41 Drawing Sheet(s) Filed in Color)

Related U.S. Application Data filed on May 7, 2015, provisional application No. 62/026,330, filed on Jul. 18, 2014.

(51) Int. Cl.
 *G16B 20/10* (2019.01)
 *G16B 30/00* (2019.01)
 *C12Q 1/689* (2018.01)

(56) References Cited

U.S. PATENT DOCUMENTS

| | | | |
|---|---|---|---|
| 7,803,929 B2 | 9/2010 | Melkonyan et al. | |
| 7,899,626 B2 | 3/2011 | Kruglyak et al. | |
| 7,914,982 B2 | 3/2011 | Melkonyan et al. | |
| 7,973,154 B2 | 7/2011 | Melkonyan et al. | |
| 8,150,626 B2 | 4/2012 | Fan et al. | |
| 8,383,335 B2 | 2/2013 | Melkonyan et al. | |
| 8,455,190 B2 | 6/2013 | Makrigiorgos | |
| 8,486,626 B2 | 7/2013 | Umansky et al. | |
| RE44,596 E | 11/2013 | Stroun et al. | |
| 8,642,261 B2 | 2/2014 | Melkonyan et al. | |
| 8,712,697 B2 | 4/2014 | Struble et al. | |
| 8,741,811 B2 | 6/2014 | Lo et al. | |
| 8,822,155 B2 | 9/2014 | Sukumar et al. | |
| 8,927,209 B2 | 1/2015 | Hamamoto et al. | |
| 9,121,069 B2 | 9/2015 | Lo et al. | |
| 9,163,229 B2 | 10/2015 | Melkonyan et al. | |
| 9,183,349 B2 | 11/2015 | Kupershmidt et al. | |
| 9,222,137 B2 | 12/2015 | Tiacci et al. | |
| 9,260,745 B2 | 2/2016 | Rava et al. | |
| 9,290,803 B2 | 3/2016 | Laird et al. | |
| 9,292,660 B2 | 3/2016 | Von Hoff et al. | |
| 9,361,426 B2 | 6/2016 | Akmaev et al. | |
| 9,453,265 B2 | 9/2016 | Umansky et al. | |
| 9,598,731 B2 | 3/2017 | Talasaz | |
| 9,732,390 B2 | 8/2017 | Lo et al. | |
| 9,758,814 B2 | 9/2017 | Fehr et al. | |
| 9,834,822 B2 | 12/2017 | Talasaz | |
| 9,840,743 B2 | 12/2017 | Talasaz | |
| 9,902,992 B2 | 2/2018 | Talasaz et al. | |
| 2005/0221314 A1 | 10/2005 | Berlin et al. | |
| 2007/0141582 A1 | 6/2007 | Li et al. | |
| 2008/0081338 A1 | 4/2008 | Lo et al. | |
| 2009/0280479 A1 | 11/2009 | Hoon et al. | |
| 2010/0068720 A1 | 3/2010 | Li et al. | |
| 2011/0028333 A1 | 2/2011 | Christensen et al. | |
| 2011/0171647 A1 | 7/2011 | Tomigahara et al. | |
| 2012/0003636 A1* | 1/2012 | Lo | C12Q 1/6809 435/6.11 |
| 2012/0041683 A1 | 2/2012 | Vaske et al. | |
| 2012/0221249 A1 | 8/2012 | Lizardi et al. | |
| 2013/0085681 A1 | 4/2013 | Deciu et al. | |
| 2014/0045181 A1 | 2/2014 | Lo et al. | |
| 2014/0080715 A1 | 3/2014 | Lo | |
| 2014/0100121 A1 | 4/2014 | Lo et al. | |
| 2014/0178348 A1 | 6/2014 | Kelsey et al. | |
| 2014/0256574 A1 | 9/2014 | Herold et al. | |
| 2014/0274740 A1 | 9/2014 | Srinivasan et al. | |
| 2014/0274752 A1 | 9/2014 | Blume et al. | |
| 2014/0274767 A1 | 9/2014 | Yegnasubramanian et al. | |
| 2014/0357497 A1 | 12/2014 | Zhang et al. | |
| 2015/0197785 A1 | 7/2015 | Carter et al. | |
| 2015/0211070 A1 | 7/2015 | Seligson et al. | |
| 2015/0322513 A1 | 11/2015 | Gromminger et al. | |
| 2015/0344970 A1 | 12/2015 | Vogelstein et al. | |
| 2015/0368708 A1 | 12/2015 | Talasaz | |
| 2015/0376700 A1 | 12/2015 | Schnall-Levin et al. | |
| 2016/0002739 A1 | 1/2016 | Schutz et al. | |
| 2016/0017419 A1 | 1/2016 | Chiu et al. | |
| 2016/0040229 A1 | 2/2016 | Talasaz et al. | |
| 2016/0046979 A1 | 2/2016 | Leamon et al. | |
| 2016/0160288 A1 | 6/2016 | Pan et al. | |
| 2016/0168643 A1 | 6/2016 | Ahlquist et al. | |
| 2016/0168648 A1 | 6/2016 | Allawi et al. | |
| 2016/0201142 A1 | 7/2016 | Lo et al. | |
| 2016/0210403 A1 | 7/2016 | Zhang et al. | |
| 2016/0232290 A1 | 8/2016 | Rava et al. | |
| 2016/0239604 A1 | 8/2016 | Chudova et al. | |
| 2016/0251704 A1 | 9/2016 | Talasaz et al. | |
| 2016/0275239 A1 | 9/2016 | Devogelaere et al. | |
| 2016/0298183 A1 | 10/2016 | Wen et al. | |
| 2016/0304936 A1 | 10/2016 | Ji et al. | |
| 2016/0326593 A1 | 11/2016 | Clement et al. | |
| 2016/0333417 A1 | 11/2016 | Talasaz | |
| 2016/0340740 A1 | 11/2016 | Zhang | |
| 2017/0016054 A1 | 1/2017 | Southern et al. | |
| 2017/0024513 A1 | 1/2017 | Lo et al. | |
| 2017/0029900 A1 | 2/2017 | Lo et al. | |
| 2017/0073774 A1 | 3/2017 | Lo et al. | |
| 2017/0101685 A1 | 4/2017 | Lo et al. | |
| 2017/0107576 A1 | 4/2017 | Babiarz et al. | |
| 2017/0121767 A1 | 5/2017 | Dor et al. | |
| 2017/0211143 A1 | 7/2017 | Shendure et al. | |
| 2017/0233829 A1 | 8/2017 | Lo et al. | |
| 2017/0249421 A1 | 8/2017 | Eberle et al. | |
| 2017/0260590 A1 | 9/2017 | Eltoukhy et al. | |
| 2017/0342500 A1 | 11/2017 | Marquard et al. | |
| 2017/0349948 A1 | 12/2017 | Lo et al. | |
| 2017/0362638 A1 | 12/2017 | Chudova et al. | |
| 2018/0023125 A1 | 1/2018 | Talasaz et al. | |
| 2018/0119230 A1 | 5/2018 | Velculescu et al. | |

FOREIGN PATENT DOCUMENTS

| | | |
|---|---|---|
| CN | 103902809 A | 7/2014 |
| EP | 1342794 A1 | 9/2003 |
| EP | 2771483 A1 | 9/2014 |
| EP | 2893040 A1 | 7/2015 |
| EP | 2997159 A1 | 3/2016 |
| EP | 3018213 A1 | 5/2016 |
| EP | 3194612 A1 | 7/2017 |
| TW | 201418474 A | 5/2014 |
| WO | 2005019477 A2 | 3/2005 |
| WO | 2005118852 A2 | 12/2005 |
| WO | 2006128192 A2 | 11/2006 |
| WO | 2008038000 A1 | 4/2008 |
| WO | 2009013492 A1 | 1/2009 |
| WO | 2011038507 A1 | 4/2011 |
| WO | 2011/130751 A1 | 10/2011 |
| WO | 2012031329 A1 | 3/2012 |
| WO | 2012071621 A1 | 6/2012 |
| WO | 2012/103031 A1 | 8/2012 |
| WO | 2012012703 A3 | 10/2012 |
| WO | 2013045432 A1 | 4/2013 |
| WO | 2013052907 A2 | 4/2013 |
| WO | 2013/066641 A1 | 5/2013 |
| WO | 2013060762 A1 | 5/2013 |
| WO | 2014/043763 A1 | 3/2014 |
| WO | 2014039556 A1 | 3/2014 |
| WO | 2014184199 A1 | 11/2014 |
| WO | 2015116837 A1 | 8/2015 |
| WO | 2015159292 A2 | 10/2015 |
| WO | 2015169947 A1 | 11/2015 |
| WO | 2015159292 A3 | 12/2015 |
| WO | 2016008451 A1 | 1/2016 |
| WO | 2016028316 A1 | 2/2016 |
| WO | 2016097251 A1 | 6/2016 |
| WO | 2016101258 A1 | 6/2016 |
| WO | 2016112850 A1 | 7/2016 |
| WO | 2016127844 A1 | 8/2016 |
| WO | 2016183106 A1 | 11/2016 |
| WO | 2016189288 A1 | 12/2016 |

OTHER PUBLICATIONS

YMD Lo et al. Maternal Plasma DNA Sequencing Reveals the Genome-Wide Genetic and Mutational Profile of the Fetus. Science Translation Medicine vol. 2, Issue 61,61 ra91, p. 1-13 (Year: 2010).*

Wong et al. Noninvasive fetal genomic, methylomic, and transcriptomic analyses using maternal plasma and clinical implications.Trends in Molecular Medicine Feb. 2015, vol. 21, No. 2, p. 98-108 (Year: 2015).*

(56) References Cited

OTHER PUBLICATIONS

Chu et al. Chapter 12 Solving Linear Equations—An Introduction to Optimization, Spring 2014, pp. 1-47, https://www.cs.ccu.edu.tw/~wtchu/courses/2015s_OPT/Lectures/Chapter%2012%20Solving%20Linear%20Equations.pdf (Year: 2014).*
Kit et al. DNA Methylation based biomarkers: Practical considerations and applciations. Biochimie 2012, vol. 94, pp. 2314-2337 (Year: 2012).*
Lee et al. Analyzing the cancer methylome through targeted bisulfite sequencing. Cancer Letters 2013, vol. 340, pp. 171-178 (Year: 2013).*
Extended European Search Report dated Dec. 1, 2017 in EP Patent Application No. 15821804.0. 6 pages.
International Search Report and Written Opinion dated Feb. 26, 2018 in International Patent Application No. PCT/CN2017/113813. 13 pages.
The Cancer Genome Atlas Research Network; "Comprehensive molecular characterization or urothelial bladder carcinoma"; Nature; Mar. 20, 2014; vol. 507; pp. 315-322.
International Search Report and Written Opinion dated Sep. 30, 2015 in PCT/CN2015/084442, 8 pages.
Houseman, Eugene Andres, et al., "Reference-free cell mixture adjustments in analysis of DNA methylation data," Bioinformatics, Jan. 21, 2014, vol. 30, No. 10, pp. 1431-1449.
Houseman, Eugene Andres, et al., "DNA methylation arrays as surrogate measures of cell mixture distribution," BMC Bioinformatics, 2012, vol. 13, No. 86, 16 pages.
Houseman, Eugene Andres, et al., "Cell-composition effects in the analysis of DNA methylation array data: a mathematical perspective," BMC Bioinformatics, 2015, vol. 16, No. 95, 16 pages.
Accomando, William, P., et al., "Quantitative reconstruction of leukocyte subsets using DNA methylation", Genome Biology, 2014, vol. 15, No. R50, 12 pages.
Koh, Winston, et al., "Noninvasive in vivo monitoring of tissue-specific global gene expression in humans," PNAS, May 20, 2014, vol. 111, No. 20, pp. 7361-7366 plus Koh, et al., "Supporting Information" 10 pages.
Fernandez, Agustin, F., et al., "A DNA methylation fingerprint of 1628 human samples," Genome Research, 2012, vol. 22, pp. 407-419.
Avraham, Ayelet et al.; "Tissue Specific DNA Methylation in Normal Human Breast Epithelium and in Breast Cancer"; PLoS One; Mar. 2014; vol. 9, Issue 3; e91805; 8 pages.
Guo, Shicheng et al.; "Identification of methylation haplotype blocks aids in deconvolution of heterogeneous tissue samples and tumor tissue-of-origin mapping from plasma DNA"; Nature Genetics; Published in final edited form Apr. 2017, vol. 49, No. 4, pp. 635-642; Author Manuscript available in PMC Sep. 6, 2017; 21 pages.
Husseiny, Mohamed I. et al.; "Tissue-Specific Methylation of Human Insulin Gene and PCR Assay for Monitoring Beta Cell Death"; PLoS One; Apr. 2014; vol. 9, Issue 4; e94591; 9 pages.
Husseiny, Mohamed I. et al.; "Development of a Quantitative Methylation-Specific Polymerase Chain Reaction Method for Monitoring Beta Cell Death in Type 1 Diabetes"; PLoS One; Oct. 2012; vol. 7, Issue 10; e47942; 11 pages.
Lebastchi, Jasmin et al.; "Immune Therapy and b-Cell Death in Type 1 Diabetes"; Diabetes; May 2013; vol. 62, No. 5; pp. 1676-1680.
Madi, Tania et al.; "The determination of tissue-specific DNA methylation patterns in forensic biofluids using bisulfite modification and pyrosequencing"; Electrophoresis; Jul. 2012; vol. 33, No. 12; pp. 1736-1745.
Toyota, Minoru et al.; "Identification of Differentially Methylated Sequences in Colorectal Cancer by Methylated CpG Island Amplification"; Cancer Research; May 15, 1999; vol. 59, Issue 10; pp. 2307-2312 (7 pages).
Castellanos-Rizaldos, Elena et al.; "COLD-PCR Amplification of Bisulfite-Converted DNA Allows the Enrichment and Sequencing of Rare Un-Methylated Genomic Regions"; PLoS One; Apr. 2014; vol. 9, Issue 4; e94103; https://doi.org/10.1371/journal.pone.0094103; 5 pages.
Chan, K.C. Allen et al.; "Noninvasive detection of cancer-associated genome-wide hypomethylation and copy number aberrations by plasma DNA bisulfite sequencing"; PNAS; Nov. 19, 2013 (Epub Nov. 4, 2013); vol. 110, No. 47; pp. 18761-18768.
Communication pursuant to Article 94(3) EPC dated Aug. 29, 2018 in EP Patent Application No. 15821804.0. 4 pages.
Jin, Hongchuan et al.; "Circulating Methylated DNA as Biomarkers for Cancer Detection"; Methylation Anica Dricu, IntechOpen; Nov. 28, 2012; DOI: 10.5772/51419; available from: https://www.intechopen.com/books/methylation-from-dna-rna-and-histones-to-diseases-and-treatment/circulating-methylated-dna-as-biomarkers-for-cancer-detection; pp. 137-152 (Chapter 6; 16 pages).
Miller, Christopher A. et al.; "ReadDepth: A Parallel R Package for Detecting Copy Number Alterations from Short Sequencing Reads"; PLoS One; Jan. 2011; vol. 6, Issue 1; e16327; 7 pages.
Page, K. et al.; "Detection of HER2 amplification in circulating free DNA in patients with breast cancer"; British Journal of Cancer; 2011; vol. 104, No. 8; pp. 1342-1348.
Radpour, Ramin et al.; "Hypermethylation of Tumor Suppressor Genes Involved in Critical Regulatory Pathways for Developing a Blood-Based Test in Breast Cancer"; PLoS One; Jan. 2011; vol. 6, Issue 1; e16080; 11 pages.
Schwarzenbach, Heidi et al.; "Cell-free nucleic acids as biomarkers in cancer patients"; Nature Reviews Cancer; Jun. 2011; vol. 11, No. 6; pp. 426-437.
Shaw, Jacqueline A. et al.; "Genomic analysis of circulating cell-free DNA infers breast cancer dormancy"; Genome Research; Feb. 2012; vol. 22, No. 2; pp. 220-231 (13 pages).
Al-Yatama et al., Detection of Y Chromosome-Specific Dna in the Plasma and Urine of Pregnant Women Using Nested Polymerase Chain Reaction, Prenatal Diagnosis, vol. 21, Issue 5, May 2001, pp. 399-402.
Beroukhim et al., The Landscape of Somatic Copy-Number Alteration Across Human Cancers, Nature, vol. 463, Feb. 18, 2010, pp. 899-905.
Botezatu et al., Genetic Analysis of DNA Excreted in Urine: A New Approach for Detecting Specific Genomic DNA Sequences from Cells Dying in an Organism, Clinical Chemistry, vol. 46, No. 8, Aug. 2000, pp. 1078-1084.
Chan et al., Cancer Genome Scanning in Plasma: Detection of Tumor-Associated Copy Number Aberrations, Single-Nucleotide Variants, and Tumoral Heterogeneity by Massively Parallel Sequencing, Clinical Chemistry, vol. 59, No. 1, Jan. 2013, pp. 211-224.
Chan et al., Quantitative Analysis of the Transrenal Excretion of Circulating EBV DNA in Nasopharyngeal Carcinoma Patients, Clinical Cancer Research, vol. 14, No. 15, Aug. 1, 2008, pp. 4809-4813.
Chen et al., Microsatellite Alterations in Plasma DNA of Small Cell Lung Cancer D Patients, Nature Medicine, vol. 2, No. 9, Sep. 1996, pp. 1033-1035.
Chiu et al., Noninvasive Prenatal Diagnosis of Fetal Chromosomal Aneuploidy by Massively Parallel Genomic Sequencing of DNA in Maternal Plasma, Proceedings of the National Academy of Sciences, vol. 105, No. 51, Dec. 23, 2008, pp. 20458-20463.
De Vlaminck et al., Circulating Cell-Free DNA Enables Noninvasive Diagnosis of Heart Transplant Rejection, Science Translational Medicine, vol. 6, No. 241, 241ra77, Jun. 18, 2014, pp. 1-8.
Demtroder et al., Genomic Alterations in Liquid Biopsies from Patients with Bladder Cancer, European Urology, vol. 70, Issue 1, Jul. 2016, pp. 75-82.
European Application No. EP15821804.0, Notice of Decision to Grant dated May 16, 2019, 2 pages.
European Application No. EP19171637.2, Extended European Search Report dated Jun. 21, 2019, 8 pages.
Feinberg et al., Hypomethylation Distinguishes Genes of Some Human Cancers From their Normal Counterparts, Nature, vol. 301, Jan. 6, 1983, pp. 89-92.

(56) References Cited

OTHER PUBLICATIONS

Hodges et al., Directional DNA Methylation Changes and Complex Intermediate States Accompany Lineage Specificity in the Adult Hematopoietic Compartment, Molecular Cell, vol. 44, Oct. 7, 2011, pp. 17-28.
Hung et al., Presence of Donor-Derived DNA and Cells in the Urine of Sex—Mismatched Hematopoietic Stem Cell Transplant Recipients: Implication for the Transrenal Hypothesis, Clinical Chemistry, vol. 55, No. 4, Apr. 2009, pp. 715-722.
Ito et al., Human Urine DNase I: Immunological Identity with Human Pancreatic DNase I, and Enzymic and Proteochemical Properties of the Enzyme, Journal of Biochemistry, vol. 95, No. 5, May 1984, pp. 1399-1406.
Jiang et al., Lengthening and Shortening of Plasma DNA in Hepatocellular Carcinoma Patients, PNAS, vol. 112, No. 11, Feb. 2, 2015, pp. E1317-E1325.
Jiang et al., Methy-Pipe: An Integrated Bioinformatics Pipeline for Whole Genome Bisulfite Sequencing Data Analysis, PLOS One, vol. 9, Issue 6, e100360, Jun. 2014, pp. 1-11.
Krzywinski et al., Circos: An Information Aesthetic for Comparative Genomics, Genome Research, vol. 19, No. 9, Jun. 18, 2009, pp. 1639-1645.
Kundaje et al., Integrative Analysis of 111 Reference Human Epigenomes, Nature, vol. 518, Feb. 19, 2015, pp. 317-330.
Leary et al., Detection of Chromosomal Alterations in the Circulation of Cancer Patients with Whole-Genome Sequencing, Science Translational Medicine, vol. 4, No. 162, Nov. 28, 2012, 21 pages.
Li et al., Inability to Detect Cell Free Fetal DNA in the Urine of Normal Pregnant Women nor in Those Affected by Preeclampsia Associated HELLP Syndrome, J Soc Gynecol Investig, vol. 10, No. 8, Dec. 2003, pp. 503-508.
Lo et al., Presence of Donor-Specific DNA in Plasma of Kidney and Liver-Transplant Recipients, The Lancet, vol. 351, No. 9112, May 2, 1998, pp. 1329-1330.
Lo et al., Presence of Fetal DNA in Maternal Plasma and Serum, The Lancet, vol. 350, No. 9076, Aug. 16, 1997, pp. 485-487.
Lui et al., Predominant Hematopoietic Origin of Cell-Free DNA in Plasma and Serum After Sex-Mismatched Bone Marrow Transplantation, Clinical Chemistry, vol. 48, Issue 3, Mar. 2002, pp. 421-427.
Lun et al., Noninvasive Prenatal Methylomic Analysis by Genomewide Bisulfite Sequencing of Maternal Plasma DNA, Clinical Chemistry, vol. 59, No. 11, Nov. 2013, pp. 1583-1594.
Meersche et al., xsample (): An R Function for Sampling Linear Inverse Problems, Journal of Statistical Software, vol. 30, Code Snippet 1, Apr. 2009, pp. 1-15.
Nadano et al., Measurement of Deoxyribonuclease I Activity in Human Tissues and Body Fluids by a Single Radial Enzyme-Diffusion Method, Clinical Chemistry, vol. 39, No. 3, Mar. 1993, pp. 448-452.
Patel et al., Association of Plasma and Urinary Mutant DNA with Clinical Outcomes in Muscle Invasive Bladder Cancer, Scientific Reports, vol. 7, No. 5554, 2017, pp. 1-12.
International Application No. PCT/CN2015/084442, International Preliminary Report on Patentability dated Feb. 2, 2017, 6 pages.
International Application No. PCT/CN2017/113813, International Preliminary Report on Patentability dated Jun. 13, 2019, 7 pages.
Snyder et al., Cell-Free DNA Comprises an In Vivo Nucleosome Footprint that Informs its Tissues-of-Origin, Cell, vol. 164, Issue 1-2, Jan. 14, 2016, pp. 57-68.
Stroun et al., The Origin and Mechanism of Circulating DNA, Annals New York Academy of Sciences, vol. 906, Issue 1, Apr. 2000, pp. 161-168.
Su et al., Detection of Mutated K-ras DNA in Urine, Plasma, and Serum of Patients with Colorectal Carcinoma or Adenomatous Polyps, Annals of the New York Academy of Sciences, vol. 1137, 2008, pp. 197-206.
Sun et al., Plasma DNA Tissue Mapping by Genome-Wide Methylation Sequencing for Noninvasive Prenatal, Cancer, and Transplantation Assessments, Proc Natl Acad Sci U.S.A, vol. 112, No. 40, Sep. 21, 2015, pp. E5503-E5512.
Szarvas et al., Deletion Analysis of Tumor and Urinary DNA to Detect Bladder Cancer: Urine Supernatant Versus Urine Sediment, Oncology Reports, vol. 18, Issue 2, Aug. 2007, pp. 405-409.
Togneri et al., Genomic Complexity of Urothelial Bladder Cancer Revealed in Urinary cfDNA, European Journal of Human Genetics, vol. 24, No. 8, Aug. 2016, pp. 1167-1174.
Tsui et al., High Resolution Size Analysis of Fetal DNA in the Urine of Pregnant Women by Paired-End Massively Parallel Sequencing, PLoS One, vol. 7, Issue 10, e48319, Oct. 31, 2012, pp. 1-7.
Underhill et al., Fragment Length of Circulating Tumor DNA, PLOS Genetics, vol. 12, No. 7, Jul. 18, 2016, pp. 1-24.
Yu et al., High-Resolution Profiling of Fetal DNA Clearance from Maternal Plasma by Massively Parallel Sequencing, Clinical Chemistry, vol. 59, Issue 8, Aug. 2013, pp. 1-10.
Zhang et al., Presence of Donor- and Recipient-Derived DNA in Cell-Free Urine Samples of Renal Transplantation Recipients: Urinary DNA Chimerism, Clinical Chemistry, vol. 45, Issue 10, Oct. 1999, pp. 1741-1746.
Beermann, Agnes et al.; "Methods for Separate Isolation of Cell-Free DNA and Cellular DNA from Urine-Application of Methylation-Specific PCR on both DNA Fractions"; The Open Biomarkers Journal; 2011; vol. 4; pp. 15-17.
Lichtenstein, Anatoly V. et al.; "Novel Applications of Polymerase Chain Reaction to Urinary Nucleic Acid Analysis"; Methods in Molecular Biology; Feb. 2006; vol. 336: Clinical Applications of PCR; pp. 145-154.
Yong, Wai-Shin et al.; "Profiling genome-wide DNA methylation"; Epigenetics & Chromatin; 2016; vol. 9, Issue 26; pp. 1-16.
Extended European Search Report dated May 28, 2020 in EP Patent Application No. 17875411.5. 11 pages.
English translation of Office Action and Search Report dated Jun. 9, 2020 in TW Patent Application No. 107111553. 5 pages.
Final Office Action dated Aug. 26, 2020 in U.S. Appl. No. 15/827,565, filed Nov. 30, 2017. 27 pages.
Kim, Wun-Jae et al.; "Epigenetic biomarkers in urothelial bladder cancer"; Expert Review of Molecular Diagnostics; 2009; vol. 9, Issue 3; pp. 259-269.
Examination Report No. 1 dated Aug. 28, 2020 in AU Patent Application No. 2017369018. 5 pages.
Written Opinion dated Sep. 14, 2020 in SG Patent Application No. 11201904042X. 10 pages.

* cited by examiner

400

Percentage contributions of plasma DNA (%)

| Case no. | Liver | Lungs | Colon | Small intestines | Pancreas | Adrenal glands | Esophagus | Adipose tissues | Heart | Brain | Neutrophils | Lymphocytes | Placenta | SNP-based fetal DNA fraction (%) | Gestational age (weeks) |
|---|---|---|---|---|---|---|---|---|---|---|---|---|---|---|---|
| 1 | 1.5 | 9.3 | 0.0 | 0.0 | 0.0 | 1.9 | 0.0 | 12.1 | 0.0 | 0.0 | 48.1 | 17.0 | 10.0 | 13.6 | 13 1/7 |
| 2 | 2.5 | 7.6 | 0.0 | 2.8 | 0.0 | 0.0 | 0.0 | 12.6 | 0.0 | 0.0 | 46.1 | 18.6 | 9.9 | 13.9 | 13 |
| 3 | 3.8 | 5.8 | 0.0 | 0.7 | 0.0 | 0.6 | 0.0 | 12.4 | 0.0 | 0.0 | 49.2 | 17.4 | 10.1 | 14.0 | 12 6/7 |
| 4 | 0.6 | 9.2 | 0.0 | 1.8 | 0.0 | 0.0 | 0.0 | 10.6 | 0.0 | 0.0 | 44.1 | 21.1 | 12.7 | 16.1 | 13 |
| 5 | 11.1 | 5.2 | 0.0 | 5.7 | 0.0 | 0.0 | 0.0 | 5.1 | 0.0 | 0.0 | 45.0 | 11.7 | 16.2 | 17.1 | 12 6/7 |
| 6 | 8.1 | 6.4 | 0.0 | 0.0 | 0.0 | 1.3 | 0.0 | 4.5 | 0.0 | 0.0 | 51.9 | 17.0 | 10.8 | 13.1 | 21 3/7 |
| 7 | 3.0 | 8.2 | 0.0 | 0.0 | 0.0 | 0.5 | 0.0 | 10.1 | 1.7 | 0.0 | 39.5 | 24.5 | 12.5 | 15.2 | 20 6/7 |
| 8 | 0.8 | 8.5 | 0.0 | 0.0 | 0.0 | 0.0 | 0.0 | 10.2 | 0.0 | 0.0 | 51.7 | 15.5 | 13.3 | 16.4 | 22 2/7 |
| 9 | 2.6 | 8.0 | 0.0 | 0.0 | 0.0 | 0.0 | 0.0 | 9.2 | 0.0 | 0.0 | 41.7 | 18.1 | 20.4 | 22.3 | 22 1/7 |
| 10 | 0.0 | 2.6 | 0.0 | 0.0 | 1.6 | 0.0 | 0.0 | 4.1 | 0.0 | 0.0 | 40.5 | 16.3 | 34.9 | 34.3 | 21 /7 |
| 11 | 0.0 | 7.4 | 0.0 | 0.0 | 0.0 | 0.0 | 0.0 | 9.8 | 0.0 | 0.0 | 41.5 | 22.0 | 19.3 | 21.0 | 38 1/7 |
| 12 | 0.6 | 10.1 | 0.0 | 0.8 | 0.0 | 1.7 | 0.0 | 6.6 | 0.0 | 0.0 | 39.0 | 18.7 | 24.3 | 27.0 | 38 3/7 |
| 13 | 0.0 | 7.4 | 0.0 | 0.0 | 0.0 | 0.0 | 0.0 | 6.3 | 0.0 | 0.0 | 36.7 | 18.7 | 29.2 | 33.0 | 38 1/7 |
| 14 | 0.0 | 5.9 | 0.0 | 0.0 | 0.0 | 0.0 | 0.0 | 8.3 | 0.0 | 0.0 | 39.6 | 12.9 | 33.3 | 36.8 | 38 2/7 |
| 15 | 0.0 | 7.3 | 0.0 | 0.0 | 0.0 | 0.0 | 0.0 | 7.2 | 0.0 | 0.0 | 32.5 | 14.6 | 38.4 | 39.5 | 38 3/7 |

| Case no. | Percentage contributions of plasma DNA (%) | | | | | | | | | | | | |
|---|---|---|---|---|---|---|---|---|---|---|---|---|---|
| | Liver | Lungs | Colon | Small intestines | Pancreas | Adrenal glands | Esophagus | Adipose tissues | Heart | Brain | Neutrophils | Lymphocytes | Placenta |
| 1 | 5.8 | 6.6 | 0.0 | 1.3 | 0.0 | 0.0 | 0.0 | 6.2 | 2.9 | 0.0 | 58.2 | 18.6 | 0.0 |
| 2 | 5.1 | 5.3 | 0.0 | 7.3 | 0.0 | 0.0 | 0.0 | 4.5 | 0.0 | 0.0 | 61.8 | 16.1 | 0.0 |
| 3 | 5.6 | 7.8 | 0.0 | 2.1 | 0.0 | 0.0 | 0.0 | 6.5 | 0.6 | 0.0 | 58.8 | 18.6 | 0.0 |
| 4 | 4.1 | 6.4 | 0.0 | 4.5 | 0.0 | 0.0 | 0.0 | 5.9 | 1.3 | 0.4 | 59.0 | 18.4 | 0.0 |
| 5 | 4.4 | 2.5 | 0.7 | 5.4 | 0.0 | 0.0 | 0.0 | 5.6 | 2.7 | 0.8 | 59.6 | 17.1 | 0.3 |
| 6 | 5.6 | 4.1 | 0.0 | 5.3 | 0.0 | 0.0 | 0.0 | 5.2 | 0.5 | 0.6 | 55.2 | 22.7 | 0.5 |
| 7 | 4.9 | 4.1 | 0.0 | 4.5 | 0.0 | 0.0 | 0.0 | 6.3 | 0.0 | 0.0 | 60.2 | 20.0 | 0.0 |
| 8 | 4.4 | 7.4 | 0.0 | 5.3 | 0.0 | 0.0 | 0.0 | 3.1 | 0.3 | 0.3 | 61.7 | 17.5 | 0.0 |
| 9 | 4.5 | 9.4 | 0.0 | 4.0 | 0.0 | 0.0 | 0.0 | 6.2 | 0.1 | 1.2 | 55.9 | 18.6 | 0.0 |
| 10 | 4.8 | 0.1 | 0.2 | 1.3 | 0.0 | 0.0 | 0.0 | 7.5 | 0.0 | 2.4 | 60.0 | 23.9 | 0.0 |
| 11 | 4.7 | 4.5 | 0.0 | 5.5 | 0.0 | 0.0 | 0.0 | 5.6 | 0.8 | 0.5 | 62.4 | 16.0 | 0.0 |
| 12 | 7.3 | 4.9 | 0.0 | 4.4 | 0.0 | 0.0 | 0.0 | 6.0 | 1.8 | 0.9 | 54.0 | 20.7 | 0.0 |
| 13 | 2.4 | 10.9 | 0.0 | 1.7 | 0.0 | 0.0 | 0.0 | 5.7 | 0.0 | 0.6 | 53.9 | 24.5 | 0.3 |
| 14 | 3.8 | 3.5 | 0.0 | 0.0 | 0.0 | 0.0 | 0.0 | 8.9 | 0.0 | 0.0 | 61.2 | 22.7 | 0.0 |
| 15 | 5.3 | 7.3 | 0.0 | 4.2 | 0.0 | 0.2 | 0.0 | 5.1 | 0.0 | 0.1 | 56.3 | 21.8 | 0.0 |
| 16 | 4.9 | 6.5 | 0.0 | 7.9 | 0.0 | 0.0 | 0.0 | 4.3 | 0.5 | 1.2 | 55.4 | 18.9 | 0.4 |
| 17 | 16.6 | 12.8 | 0.0 | 0.0 | 0.0 | 0.0 | 0.0 | 4.4 | 0.0 | 0.0 | 47.7 | 18.5 | 0.0 |
| 18 | 8.3 | 5.6 | 0.0 | 2.1 | 0.0 | 0.0 | 0.0 | 7.5 | 0.6 | 0.2 | 56.2 | 19.4 | 1.3 |
| 19 | 6.0 | 0.0 | 1.0 | 2.3 | 0.0 | 0.0 | 0.0 | 9.3 | 0.0 | 0.0 | 54.5 | 26.3 | 0.6 |
| 20 | 2.0 | 4.8 | 0.0 | 0.0 | 0.0 | 0.5 | 0.0 | 10.5 | 0.0 | 0.0 | 58.5 | 22.5 | 1.1 |
| 21 | 8.5 | 0.0 | 0.0 | 4.5 | 0.0 | 0.0 | 0.0 | 9.4 | 0.0 | 0.0 | 53.9 | 23.4 | 0.2 |
| 22 | 6.4 | 11.1 | 0.0 | 4.0 | 0.0 | 0.0 | 0.0 | 6.7 | 0.0 | 0.0 | 53.7 | 18.1 | 0.0 |
| 23 | 2.0 | 2.6 | 0.0 | 8.7 | 0.0 | 0.0 | 0.0 | 6.5 | 1.1 | 0.0 | 62.5 | 15.0 | 1.3 |
| 24 | 5.4 | 2.2 | 0.0 | 2.7 | 0.0 | 0.0 | 0.0 | 5.9 | 0.0 | 1.6 | 65.2 | 15.2 | 0.9 |
| 25 | 21.0 | 0.0 | 0.0 | 7.1 | 0.0 | 0.0 | 0.0 | 3.8 | 0.0 | 0.0 | 51.6 | 16.4 | 0.0 |
| 26 | 7.0 | 6.4 | 0.0 | 5.1 | 0.0 | 0.0 | 0.0 | 4.1 | 1.6 | 0.0 | 55.9 | 19.0 | 0.0 |
| 27 | 7.9 | 10.4 | 0.0 | 0.3 | 0.0 | 0.0 | 0.0 | 4.8 | 0.0 | 0.0 | 58.1 | 17.5 | 0.0 |
| 28 | 5.4 | 9.7 | 0.0 | 4.2 | 0.0 | 0.0 | 0.0 | 5.1 | 0.0 | 0.0 | 55.7 | 20.0 | 0.0 |
| 29 | 6.2 | 6.8 | 0.0 | 0.0 | 0.0 | 0.0 | 0.0 | 6.3 | 0.0 | 0.0 | 60.7 | 20.2 | 0.0 |
| 30 | 6.9 | 5.1 | 0.0 | 5.2 | 0.0 | 0.0 | 0.0 | 6.4 | 1.4 | 0.0 | 58.8 | 16.2 | 0.0 |
| 31 | 14.0 | 6.4 | 0.0 | 4.5 | 0.0 | 0.0 | 0.0 | 4.9 | 0.7 | 0.0 | 53.2 | 16.2 | 0.0 |
| 32 | 9.9 | 5.5 | 0.0 | 1.9 | 0.0 | 0.0 | 0.0 | 6.3 | 0.6 | 0.0 | 60.1 | 15.6 | 0.0 |
| Median | 5.5 | 5.3 | 0.0 | 4.2 | 0.0 | 0.0 | 0.0 | 6.1 | 0.0 | 0.0 | 58.3 | 18.7 | 0.0 |
| Lower quartile | 4.6 | 3.9 | 0.0 | 1.9 | 0.0 | 0.0 | 0.0 | 5.0 | 0.0 | 0.0 | 55.0 | 16.5 | 0.0 |
| Upper quartile | 7.1 | 7.3 | 0.0 | 5.3 | 0.0 | 0.0 | 0.0 | 6.6 | 0.8 | 0.5 | 60.1 | 21.0 | 0.3 |

FIG. 6

| 700 | Pregnant women | | | | | | | | | | | Non-pregnant subjects | | | |
|---|---|---|---|---|---|---|---|---|---|---|---|---|---|---|---|
| | 1 | 2 | 3 | 4 | 5 | 6 | 7 | 8 | 9 | 10 | 11 | 1 | 2 | 3 | 4 |
| Buffy coat | 58% | 64% | 65% | 53% | 83% | 52% | 75% | 71% | 52% | 66% | 69% | 87% | 83% | 96% | 80% |
| Esophagus | 0% | 0% | 0% | 2% | 0% | 0% | 0% | 3% | 0% | 0% | 0% | 0% | 0% | 0% | 0% |
| Small intestines | 0% | 0% | 0% | 4% | 0% | 0% | 0% | 0% | 0% | 0% | 0% | 0% | 0% | 0% | 0% |
| Colon | 0% | 0% | 0% | 0% | 0% | 0% | 0% | 0% | 0% | 0% | 0% | 0% | 5% | 0% | 0% |
| Pancreas | 0% | 1% | 0% | 1% | 0% | 0% | 0% | 0% | 1% | 3% | 2% | 1% | 0% | 0% | 0% |
| Liver | 3% | 8% | 10% | 1% | 0% | 11% | 6% | 7% | 4% | 9% | 8% | 7% | 7% | 3% | 6% |
| Lung | 0% | 0% | 0% | 0% | 0% | 0% | 0% | 0% | 0% | 0% | 0% | 0% | 0% | 0% | 0% |
| Heart | 0% | 0% | 0% | 0% | 0% | 0% | 0% | 0% | 0% | 0% | 10% | 0% | 0% | 0% | 2% |
| Adrenal gland | 0% | 1% | 0% | 1% | 0% | 4% | 1% | 4% | 3% | 3% | 4% | 2% | 5% | 0% | 5% |
| Hippocampus | 1% | 3% | 0% | 1% | 2% | 0% | 0% | 0% | 0% | 3% | 4% | 2% | 0% | 0% | 5% |
| Placenta | 38% | 24% | 25% | 36% | 15% | 34% | 18% | 15% | 40% | 19% | 7% | 2% | 5% | 1% | 2% |
| Fetal DNA fraction determined by counting fetal specific alleles | 32% | 21% | 26% | 28% | 11% | 25% | 17% | 13% | 13% | 32% | 3% | 0% | 0% | 0% | 0% |

FIG. 7

|  | Pregnant women | | | | | | | | | | | Non-pregnant subjects | | | |
|---|---|---|---|---|---|---|---|---|---|---|---|---|---|---|---|
|  | 1 | 2 | 3 | 4 | 5 | 6 | 7 | 8 | 9 | 10 | 11 | 1 | 2 | 3 | 4 |
| Buffy coat | 43% | 44% | 47% | 40% | 47% | 41% | 38% | 41% | 43% | 39% | 45% | 10% | 11% | 1% | 13% |
| Esophagus | 0% | 0% | 0% | 0% | 0% | 0% | 0% | 0% | 0% | 0% | 0% | 0% | 0% | 0% | 0% |
| Small intestines | 0% | 4% | 1% | 2% | 3% | 0% | 1% | 5% | 0% | 0% | 0% | 0% | 0% | 0% | 0% |
| Colon | 25% | 18% | 10% | 23% | 14% | 23% | 24% | 20% | 27% | 25% | 16% | 17% | 7% | 22% | 27% |
| Pancreas | 0% | 0% | 0% | 0% | 0% | 0% | 0% | 0% | 0% | 0% | 0% | 0% | 0% | 0% | 0% |
| Liver | 4% | 8% | 11% | 4% | 8% | 11% | 9% | 0% | 0% | 0% | 0% | 0% | 0% | 0% | 0% |
| Lung | 0% | 0% | 0% | 1% | 0% | 0% | 0% | 3% | 0% | 0% | 11% | 0% | 0% | 0% | 0% |
| Heart | 0% | 0% | 1% | 3% | 0% | 0% | 1% | 0% | 0% | 0% | 0% | 0% | 0% | 0% | 0% |
| Adrenal gland | 0% | 3% | 6% | 0% | 0% | 0% | 7% | 4% | 3% | 7% | 7% | 24% | 23% | 20% | 4% |
| Hippocampus | 7% | 10% | 7% | 11% | 12% | 10% | 8% | 15% | 9% | 11% | 16% | 44% | 42% | 41% | 50% |
| Placenta | 21% | 13% | 18% | 16% | 15% | 16% | 11% | 12% | 18% | 18% | 6% | 4% | 16% | 15% | 7% |
| Fetal DNA fraction determined by counting fetal specific alleles | 32% | 21% | 26% | 28% | 11% | 25% | 17% | 13% | 13% | 32% | 3% | 0% | 0% | 0% | 0% |

FIG. 8

| | HCC patient | | | | | | | | | | Healthy subjects without a cancer | | | |
|---|---|---|---|---|---|---|---|---|---|---|---|---|---|---|
| | 1 | 2 | 3 | 4 | 5 | 6 | 7 | 8 | 9 | 10 | 1 | 2 | 3 | 4 |
| Buffy coat | 34% | 61% | 74% | 65% | 60% | 7% | 62% | 76% | 57% | 56% | 91% | 83% | 80% | 84% |
| Esophagus | 0% | 1% | 0% | 0% | 0% | 0% | 0% | 0% | 0% | 0% | 0% | 1% | 0% | 2% |
| Small intestines | 5% | 0% | 0% | 6% | 7% | 0% | 3% | 0% | 0% | 0% | 0% | 0% | 16% | 2% |
| Colon | 0% | 1% | 0% | 1% | 5% | 10% | 0% | 0% | 3% | 0% | 0% | 0% | 0% | 0% |
| Pancreas | 1% | 0% | 0% | 0% | 6% | 3% | 2% | 0% | 0% | 1% | 0% | 1% | 0% | 0% |
| Liver | 22% | 16% | 4% | 13% | 12% | 49% | 17% | 10% | 0% | 0% | 2% | 3% | 4% | 1% |
| Lung | 9% | 3% | 8% | 4% | 0% | 17% | 8% | 10% | 3% | 3% | 0% | 5% | 0% | 6% |
| Heart | 9% | 10% | 10% | 4% | 5% | 0% | 2% | 1% | 0% | 0% | 5% | 6% | 0% | 4% |
| Adrenal glands | 1% | 0% | 0% | 2% | 0% | 0% | 0% | 0% | 0% | 0% | 0% | 0% | 0% | 0% |
| Hippocampus | 6% | 0% | 2% | 2% | 1% | 1% | 0% | 1% | 0% | 0% | 2% | 0% | 0% | 0% |
| HCC tumor | 14% | 7% | 2% | 3% | 4% | 13% | 7% | 2% | 37% | 40% | 0% | 0% | 0% | 0% |
| Tumor-derived DNA fraction determined by genomewide methylation level | 14% | 10% | 6% | 7% | 11% | 25% | 11% | 5% | 20% | 47% | 0% | 0% | 0% | 0% |

FIG. 10

| Case no. | Liver | Lungs | Colon | Small intestines | Pancreas | Adrenal glands | Esophagus | Adipose tissues | Heart | Brain | Neutrophils | Lymphocytes | SNP-based donor DNA fraction (%) |
|---|---|---|---|---|---|---|---|---|---|---|---|---|---|
| LTP-1 | 4.4 | 0.8 | 0.0 | 6.2 | 0.6 | 1.0 | 0.0 | 4.8 | 2.4 | 1.0 | 61.3 | 17.7 | 9.1 |
| LTP-2 | 23.6 | 0.1 | 0.0 | 13.2 | 0.0 | 0.0 | 0.0 | 4.9 | 2.3 | 0.0 | 45.9 | 10.0 | 28.8 |
| LTP-3 | 5.9 | 4.4 | 0.4 | 0.0 | 1.1 | 0.0 | 0.0 | 10.0 | 0.0 | 0.0 | 56.8 | 21.4 | 5.5 |
| LTP-4 | 7.5 | 4.0 | 7.9 | 8.9 | 0.0 | 0.0 | 0.0 | 7.1 | 0.0 | 1.4 | 48.6 | 14.6 | 7.8 |
| BMT-1 | 0.4 | 9.3 | 0.0 | 0.0 | 0.0 | 0.0 | 0.0 | 13.8 | 0.0 | 0.0 | 39.0 | 17.5 | 79.8 |
| BMT-2 | 5.8 | 4.1 | 1.0 | 3.3 | 0.0 | 0.0 | 0.0 | 12.3 | 0.0 | 2.3 | 49.7 | 21.6 | 74.1 |
| BMT-3 | 4.3 | 2.1 | 0.0 | 0.0 | 0.0 | 0.0 | 0.0 | 13.8 | 0.0 | 0.0 | 53.0 | 26.8 | 75.7 |

LTP: Liver transplant recipient; BMT: Bone marrow transplant recipient.

FIG. 13

| | HCC | | | | | | | | | | Lung cancer | | Colorectal cancer | Healthy subjects without cancer | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Buffy coat | 43% | 65% | 74% | 80% | 72% | 1% | 70% | 81% | 49% | 55% | 60% | 70% | 55% | 92% | 89% | 89% | 85% |
| Esophagus | 0% | 2% | 1% | 2% | 2% | 5% | 2% | 0% | 5% | 0% | 0% | 0% | 9% | 0% | 0% | 0% | 0% |
| Small intestines | 0% | 6% | 12% | 0% | 3% | 3% | 2% | 7% | 0% | 5% | 0% | 0% | 0% | 0% | 1% | 1% | 3% |
| Colon | 10% | 3% | 0% | 0% | 0% | 5% | 1% | 0% | 10% | 0% | 0% | 0% | 28% | 0% | 0% | 0% | 0% |
| Pancreas | 1% | 3% | 1% | 1% | 5% | 7% | 2% | 0% | 10% | 9% | 2% | 0% | 4% | 0% | 1% | 0% | 1% |
| Liver | 28% | 9% | 5% | 11% | 14% | 49% | 12% | 8% | 26% | 27% | 13% | 3% | 3% | 3% | 3% | 3% | 4% |
| Lung | 0% | 0% | 4% | 0% | 0% | 21% | 8% | 3% | 0% | 0% | 17% | 16% | 0% | 0% | 2% | 0% | 6% |
| Heart | 10% | 6% | 0% | 5% | 1% | 5% | 4% | 1% | 0% | 0% | 9% | 11% | 0% | 4% | 3% | 6% | 0% |
| Adrenal glands | 6% | 4% | 0% | 0% | 3% | 4% | 0% | 0% | 0% | 5% | 0% | 0% | 0% | 0% | 0% | 0% | 0% |
| Hippocampus | 0% | 2% | 3% | 1% | 0% | 1% | 0% | 0% | 0% | 5% | 0% | 0% | 0% | 1% | 0% | 1% | 0% |

| | HCC patient | | | | | | | | | | Lung cancer | | Colorectal cancer |
|---|---|---|---|---|---|---|---|---|---|---|---|---|---|
| | 1 | 2 | 3 | 4 | 5 | 6 | 7 | 8 | 9 | 10 | 1 | 2 | 3 |
| Buffy coat | -46% | -24% | -15% | -9% | -17% | -88% | -19% | -8% | -40% | -34% | -29% | -19% | -34% |
| Esophagus | 0% | 2% | 1% | 2% | 2% | 5% | 2% | 0% | 5% | 0% | 0% | 0% | 9% |
| Small intestines | -1% | 5% | 11% | -1% | 2% | 2% | 1% | 6% | -1% | 4% | -1% | -1% | -1% |
| Colon | 10% | 3% | 0% | 0% | 0% | 5% | 1% | 0% | 10% | 0% | 0% | 0% | 28% |
| Pancreas | 1% | 3% | 1% | 1% | 5% | 7% | 2% | -1% | 10% | 9% | 2% | -1% | 4% |
| Liver | 25% | 6% | 2% | 8% | 11% | 46% | 9% | 5% | 23% | 24% | 10% | 0% | 0% |
| Lung | -2% | -2% | 2% | -2% | -2% | 19% | 6% | 1% | -2% | -2% | 15% | 14% | -2% |
| Heart | 7% | 3% | -3% | 2% | -2% | 2% | 1% | -2% | -3% | -3% | 6% | 8% | -3% |
| Adrenal glands | 6% | 4% | 0% | 0% | 3% | 4% | 0% | 0% | 0% | 0% | 0% | 0% | 0% |
| Hippocampus | -1% | 2% | 3% | 1% | -1% | 1% | -1% | -1% | -1% | 5% | -1% | -1% | -1% |

| Cancer type | Case no. | Percentage contributions of plasma DNA (%) | | | | | | | | | | | |
|---|---|---|---|---|---|---|---|---|---|---|---|---|---|
| | | Liver | Lungs | Colon | Small Intestines | Pancreas | Adrenal glands | Esophagus | Adipose tissues | Heart | Brain | Neutrophils | Lymphocytes |
| HCC | HCC-1 | 36.5 | 4.3 | 8.7 | 0.0 | 2.1 | 0.0 | 0.0 | 0.0 | 0.0 | 0.0 | 34.0 | 14.3 |
| HCC | HCC-2 | 38.1 | 2.8 | 0.0 | 0.0 | 7.0 | 0.0 | 0.0 | 0.0 | 0.0 | 0.0 | 38.9 | 13.2 |
| HCC | HCC-3 | 4.6 | 9.7 | 0.0 | 10.4 | 0.0 | 0.0 | 0.0 | 7.7 | 4.8 | 0.4 | 47.7 | 14.6 |
| HCC | HCC-4 | 20.6 | 6.8 | 1.9 | 3.3 | 0.0 | 0.0 | 0.0 | 4.2 | 0.0 | 0.0 | 50.8 | 12.4 |
| HCC | HCC-5 | 10.7 | 18.1 | 0.0 | 3.7 | 0.0 | 0.0 | 0.0 | 0.1 | 1.2 | 0.0 | 51.5 | 14.7 |
| HCC | HCC-6 | 33.3 | 9.5 | 0.0 | 11.0 | 0.9 | 0.0 | 0.0 | 6.9 | 0.3 | 0.0 | 31.5 | 6.6 |
| HCC | HCC-7 | 13.4 | 13.1 | 1.8 | 10.4 | 0.0 | 0.0 | 0.0 | 0.0 | 0.0 | 0.9 | 49.9 | 10.4 |
| HCC | HCC-8 | 12.2 | 5.9 | 0.0 | 8.0 | 0.2 | 0.6 | 0.0 | 4.5 | 0.5 | 0.0 | 51.8 | 16.3 |
| HCC | HCC-9 | 32.9 | 13.9 | 0.0 | 13.1 | 1.7 | 2.8 | 0.0 | 5.9 | 2.0 | 2.3 | 20.7 | 5.1 |
| HCC | HCC-10 | 12.4 | 15.3 | 0.2 | 6.3 | 0.0 | 0.9 | 0.0 | 4.0 | 0.0 | 0.5 | 33.3 | 27.0 |
| HCC | HCC-11 | 43.1 | 8.1 | 1.3 | 8.8 | 2.7 | 0.0 | 0.5 | 4.1 | 0.0 | 0.0 | 24.4 | 7.0 |
| HCC | HCC-12 | 11.5 | 9.5 | 0.0 | 6.6 | 0.0 | 0.0 | 0.0 | 1.5 | 2.6 | 0.4 | 49.4 | 18.4 |
| HCC | HCC-13 | 23.0 | 6.4 | 0.7 | 0.0 | 5.8 | 0.0 | 0.0 | 0.0 | 0.0 | 0.0 | 47.3 | 16.8 |
| HCC | HCC-14 | 4.9 | 11.4 | 0.4 | 6.0 | 0.0 | 0.0 | 0.0 | 7.7 | 0.0 | 1.6 | 53.2 | 14.7 |
| HCC | HCC-15 | 8.1 | 7.3 | 0.0 | 4.4 | 0.0 | 0.0 | 0.0 | 5.2 | 0.0 | 0.0 | 61.2 | 13.7 |
| HCC | HCC-16 | 11.1 | 9.7 | 0.0 | 8.7 | 0.0 | 0.0 | 0.0 | 5.2 | 0.5 | 0.0 | 47.3 | 17.4 |
| HCC | HCC-17 | 13.3 | 11.4 | 0.0 | 13.9 | 0.0 | 0.0 | 0.0 | 0.6 | 0.0 | 0.0 | 47.6 | 13.1 |
| HCC | HCC-18 | 19.4 | 6.4 | 0.0 | 16.1 | 1.8 | 0.0 | 0.0 | 5.1 | 1.8 | 0.3 | 33.9 | 15.2 |
| HCC | HCC-19 | 12.9 | 14.1 | 0.0 | 3.0 | 0.0 | 0.0 | 0.0 | 5.6 | 2.1 | 0.0 | 47.6 | 14.7 |
| HCC | HCC-20 | 8.7 | 13.0 | 0.0 | 2.1 | 0.0 | 0.0 | 0.0 | 8.9 | 0.0 | 0.0 | 49.8 | 17.5 |
| HCC | HCC-21 | 67.0 | 4.2 | 6.0 | 3.5 | 12.5 | 0.0 | 0.0 | 0.0 | 0.3 | 0.0 | 5.6 | 0.8 |
| HCC | HCC-22 | 5.8 | 13.2 | 0.0 | 0.1 | 0.0 | 0.0 | 0.0 | 8.2 | 0.0 | 0.0 | 46.3 | 23.4 |
| HCC | HCC-23 | 5.4 | 7.2 | 0.0 | 5.8 | 0.0 | 0.0 | 0.0 | 4.4 | 0.0 | 0.4 | 57.6 | 19.1 |
| HCC | HCC-24 | 7.2 | 10.1 | 0.0 | 1.6 | 0.0 | 0.0 | 0.0 | 10.8 | 2.6 | 0.0 | 49.4 | 18.4 |
| HCC | HCC-25 | 19.9 | 7.6 | 0.6 | 11.3 | 0.0 | 1.0 | 0.0 | 1.2 | 4.7 | 1.1 | 39.5 | 13.2 |
| HCC | HCC-26 | 11.6 | 8.7 | 0.0 | 6.2 | 0.0 | 0.0 | 0.0 | 7.1 | 0.0 | 0.0 | 52.8 | 13.5 |
| HCC | HCC-27 | 7.7 | 7.5 | 0.0 | 5.5 | 0.0 | 0.0 | 0.0 | 8.6 | 0.0 | 0.0 | 53.6 | 17.0 |
| HCC | HCC-28 | 37.9 | 1.3 | 0.0 | 0.0 | 7.3 | 0.0 | 0.0 | 0.0 | 0.0 | 0.0 | 38.3 | 15.1 |
| HCC | HCC-29 | 61.4 | 1.8 | 4.3 | 0.0 | 6.2 | 0.0 | 0.0 | 0.0 | 0.0 | 0.0 | 18.4 | 5.6 |
| | Median | 12.9 | 8.7 | 0.0 | 5.8 | 0.0 | 0.0 | 0.0 | 4.4 | 0.0 | 0.0 | 47.6 | 14.7 |
| | Lower quantile | 8.7 | 6.4 | 0.0 | 2.1 | 0.0 | 0.0 | 0.0 | 0.1 | 0.0 | 0.0 | 34.0 | 13.1 |
| | Upper quantile | 32.9 | 11.4 | 0.6 | 8.8 | 1.8 | 0.0 | 0.0 | 6.9 | 1.2 | 0.4 | 50.8 | 17.0 |
| Lung cancer | LC-1 | 3.2 | 11.1 | 5.6 | 6.0 | 1.7 | 0.0 | 4.2 | 10.4 | 2.8 | 1.2 | 42.4 | 11.5 |
| Lung cancer | LC-2 | 6.0 | 16.7 | 0.0 | 6.6 | 0.0 | 0.0 | 0.0 | 2.3 | 3.2 | 0.7 | 49.4 | 15.1 |
| Lung cancer | LC-3 | 1.4 | 11.9 | 1.0 | 0.5 | 0.0 | 0.0 | 0.0 | 7.0 | 0.9 | 0.1 | 59.3 | 17.9 |
| Lung cancer | LC-4 | 9.2 | 35.3 | 0.0 | 0.0 | 0.0 | 0.0 | 0.0 | 0.2 | 6.9 | 0.0 | 34.5 | 13.8 |
| | Median | 3.2 | 11.9 | 1.0 | 6.0 | 0.0 | 0.0 | 0.0 | 7.0 | 2.8 | 0.7 | 49.4 | 15.1 |
| | Lower quantile | 2.3 | 11.5 | 0.5 | 3.2 | 0.0 | 0.0 | 0.0 | 4.6 | 1.8 | 0.4 | 45.9 | 13.3 |
| | Upper quantile | 4.6 | 14.3 | 3.3 | 6.3 | 0.8 | 0.0 | 2.1 | 8.7 | 3.0 | 0.9 | 54.4 | 16.5 |
| Colorectal Cancer | CRC-1 | 4.4 | 0.0 | 32.4 | 0.0 | 1.5 | 0.0 | 10.6 | 0.0 | 0.0 | 2.1 | 24.0 | 24.9 |

HCC, hepatocellular carcinoma

| Case | Liver | Lung | Colon | Small intestines | Pancreas | Adrenal gland | Esophagus | Adipose | Heart | Brain | Neutrophils | Lymphocytes |
|------|-------|------|-------|------------------|----------|---------------|-----------|---------|-------|-------|-------------|-------------|
| 1 | 6.1 | 9.8 | 0.0 | 2.7 | 0.0 | 0.0 | 0.0 | 5.7 | 1.7 | 0.4 | 51.0 | 22.5 |
| 2 | 4.2 | 10.2 | 0.0 | 0.5 | 0.0 | 0.0 | 0.0 | 4.8 | 0.0 | 0.0 | 59.7 | 20.7 |
| 3 | 5.4 | 8.8 | 0.0 | 2.4 | 0.0 | 0.0 | 0.0 | 4.0 | 2.4 | 0.3 | 55.6 | 21.1 |
| 4 | 3.5 | 7.6 | 0.0 | 4.7 | 0.0 | 0.0 | 0.0 | 2.7 | 2.8 | 0.2 | 52.9 | 25.6 |
| 5 | 5.1 | 16.1 | 0.0 | 0.0 | 0.0 | 0.0 | 0.0 | 4.5 | 3.0 | 0.0 | 55.6 | 15.8 |
| 6 | 5.3 | 10.3 | 0.0 | 2.3 | 0.0 | 0.0 | 0.0 | 3.1 | 1.2 | 0.0 | 60.0 | 17.8 |
| 7 | 4.4 | 13.9 | 0.0 | 2.1 | 0.0 | 0.0 | 0.0 | 8.8 | 1.1 | 0.0 | 49.5 | 20.3 |
| 8 | 15.8 | 9.8 | 0.0 | 5.1 | 0.0 | 0.0 | 0.0 | 1.5 | 4.6 | 0.0 | 47.1 | 16.1 |
| 9 | 52.9 | 6.8 | 0.0 | 4.5 | 0.0 | 0.0 | 0.0 | 1.4 | 0.0 | 0.0 | 19.7 | 14.8 |

Percentage contribution (%)

FIG. 25

| Organ | Percentage contributions of plasma DNA (%) |
|---|---|
| Liver | 0.0 |
| Lungs | 0.0 |
| Colon | 10.3 |
| Small intestines | 0.0 |
| Pancreas | 0.0 |
| Adrenal glands | 0.0 |
| Esophagus | 0.9 |
| Adipose tissues | 0.0 |
| Heart | 0.0 |
| Brain | 0.2 |
| Neutrophils | 2.3 |
| T-cells | 8.0 |
| B-cells | 62.2 |
| Placenta | 16.1 |

3500

| Groups | Case no. | Raw reads | Mapped reads | Mappability (%) | Nonduplicated reads | Duplication rate (%) | Sequence Depth |
|---|---|---|---|---|---|---|---|
| Pregnant women | 1 | 152,872,939 | 122,960,143 | 80.4 | 115,939,334 | 5.7 | 5.8 |
| | 2 | 131,088,905 | 98,718,701 | 75.3 | 73,286,374 | 25.8 | 3.7 |
| | 3 | 142,201,104 | 107,249,493 | 75.4 | 67,029,452 | 37.5 | 3.4 |
| | 4 | 186,789,363 | 145,354,184 | 77.8 | 116,164,567 | 20.0 | 5.8 |
| | 5 | 179,753,851 | 140,610,344 | 78.2 | 115,860,114 | 17.6 | 5.8 |
| | 6 | 141,102,611 | 105,071,140 | 74.5 | 63,340,770 | 39.7 | 3.2 |
| | 7 | 147,382,666 | 108,972,384 | 73.9 | 65,389,224 | 40.0 | 3.3 |
| | 8 | 152,714,034 | 120,208,080 | 78.7 | 105,380,449 | 12.3 | 5.3 |
| | 9 | 113,760,046 | 87,942,163 | 77.3 | 71,155,869 | 19.1 | 3.6 |
| | 10 | 146,362,683 | 108,629,367 | 74.1 | 56,639,794 | 48.0 | 2.8 |
| | 11 | 155,641,485 | 125,480,847 | 80.6 | 119,380,234 | 4.8 | 6.0 |
| | 12 | 160,565,961 | 130,639,639 | 81.4 | 126,815,444 | 2.9 | 6.3 |
| | 13 | 143,489,292 | 115,776,354 | 80.7 | 105,459,104 | 8.9 | 5.3 |
| | 14 | 156,059,015 | 126,846,709 | 81.2 | 122,397,946 | 3.4 | 6.1 |
| | 15 | 163,738,994 | 130,797,282 | 79.9 | 118,923,309 | 9.1 | 5.9 |
| Organ transplant recipients | LTP1 | 87,162,575 | 64,201,436 | 73.7 | 62,310,466 | 3.0 | 3.2 |
| | LTP2 | 102,071,655 | 73,329,149 | 71.8 | 71,970,658 | 1.9 | 3.7 |
| | LTP3 | 81,333,418 | 58,889,025 | 72.4 | 57,186,389 | 2.9 | 2.9 |
| | LTP4 | 72,670,331 | 54,563,050 | 75.1 | 53,493,357 | 2.0 | 2.7 |
| | BMT1 | 121,174,338 | 97,291,012 | 80.3 | 96,476,153 | 0.8 | 4.9 |
| | BMT2 | 99,754,528 | 78,565,631 | 78.8 | 77,293,636 | 1.6 | 3.8 |
| | BMT3 | 87,875,700 | 66,725,179 | 76.1 | 64,893,510 | 2.8 | 3.3 |
| HCC patients | HCC-1 | 183,208,657 | 149,626,481 | 81.7 | 118,353,426 | 20.9 | 3.0 |
| | HCC-2 | 200,193,884 | 160,746,469 | 80.3 | 134,106,038 | 16.6 | 3.4 |
| | HCC-3 | 170,718,448 | 137,260,507 | 80.4 | 106,701,398 | 22.3 | 2.7 |
| | HCC-4 | 157,123,507 | 124,966,177 | 79.5 | 80,506,281 | 35.6 | 2.0 |
| | HCC-5 | 197,193,431 | 154,811,402 | 78.5 | 104,389,826 | 32.6 | 2.6 |
| | HCC-6 | 160,235,821 | 129,686,216 | 80.9 | 108,691,121 | 16.2 | 2.7 |
| | HCC-7 | 194,402,134 | 155,465,046 | 80.0 | 84,866,890 | 45.4 | 2.1 |
| | HCC-8 | 175,778,779 | 139,651,243 | 79.4 | 97,335,892 | 30.3 | 2.4 |
| | HCC-9 | 170,003,416 | 135,265,696 | 79.6 | 114,514,323 | 15.3 | 2.9 |
| | HCC-10 | 216,348,490 | 166,436,075 | 76.9 | 141,625,528 | 14.9 | 3.5 |
| | HCC-11 | 179,496,062 | 142,453,607 | 79.4 | 122,615,917 | 13.9 | 3.1 |
| | HCC-12 | 180,754,659 | 143,883,053 | 79.6 | 123,613,547 | 14.1 | 3.1 |
| | HCC-13 | 160,489,200 | 114,965,828 | 71.6 | 99,132,580 | 13.8 | 2.5 |
| | HCC-14 | 159,476,901 | 126,788,478 | 79.5 | 94,863,555 | 25.1 | 2.4 |
| | HCC-15 | 163,509,987 | 139,157,545 | 78.9 | 104,858,008 | 18.3 | 2.6 |
| | HCC-16 | 166,021,743 | 128,502,931 | 77.4 | 93,226,828 | 27.5 | 2.3 |
| | HCC-17 | 127,458,566 | 99,340,619 | 77.9 | 85,569,282 | 13.9 | 2.1 |
| | HCC-18 | 128,681,079 | 102,632,297 | 79.8 | 92,672,298 | 9.7 | 2.3 |
| | HCC-19 | 180,997,328 | 145,319,878 | 80.3 | 122,489,348 | 15.7 | 3.1 |
| | HCC-20 | 171,346,367 | 140,206,256 | 81.8 | 116,122,664 | 17.2 | 2.9 |
| | HCC-21 | 145,708,246 | 109,755,892 | 75.3 | 93,920,112 | 14.4 | 2.3 |
| | HCC-22 | 164,510,182 | 131,354,954 | 79.8 | 112,546,748 | 14.3 | 2.8 |
| | HCC-23 | 144,497,935 | 113,055,922 | 78.2 | 94,961,863 | 16.0 | 2.4 |
| | HCC-24 | 189,884,319 | 142,264,969 | 74.9 | 114,311,112 | 19.7 | 2.9 |
| | HCC-25 | 137,871,045 | 109,599,375 | 79.5 | 99,068,869 | 9.6 | 2.5 |
| | HCC-26 | 187,605,052 | 145,723,576 | 77.6 | 108,798,513 | 25.3 | 2.7 |
| | HCC-27 | 196,128,614 | 148,018,621 | 75.5 | 117,373,019 | 20.7 | 2.9 |
| | HCC-28 | 203,248,321 | 157,165,850 | 77.3 | 137,996,036 | 12.2 | 3.4 |
| | HCC-29 | 191,895,021 | 143,424,050 | 74.7 | 126,378,570 | 11.9 | 3.2 |
| | HCC-30 | 196,128,614 | 148,018,621 | 75.5 | 117,373,019 | 20.7 | 2.9 |
| | HCC-31 | 203,248,321 | 157,165,850 | 77.3 | 137,996,036 | 12.2 | 3.4 |
| | HCC-32 | 191,895,021 | 143,424,050 | 74.7 | 126,378,570 | 11.9 | 3.2 |
| Healthy Controls | 1 | 192,531,153 | 144,093,083 | 74.8 | 109,868,604 | 23.8 | 2.7 |
| | 2 | 192,241,189 | 153,590,009 | 79.9 | 85,796,741 | 44.1 | 2.1 |
| | 3 | 164,610,618 | 128,707,389 | 78.1 | 100,079,252 | 22.2 | 2.5 |
| | 4 | 185,360,008 | 146,406,266 | 79.0 | 98,687,734 | 32.6 | 2.5 |
| | 5 | 173,102,664 | 139,662,668 | 80.7 | 78,954,815 | 43.5 | 2.0 |
| | 6 | 154,314,792 | 117,201,487 | 76.0 | 57,169,204 | 51.3 | 1.4 |
| | 7 | 225,512,421 | 165,337,630 | 73.3 | 97,447,016 | 41.1 | 2.4 |
| | 8 | 236,838,421 | 174,910,823 | 73.9 | 74,080,823 | 57.6 | 1.9 |
| | 9 | 169,813,693 | 134,097,600 | 79.0 | 98,179,128 | 26.8 | 2.5 |
| | 10 | 215,037,461 | 161,508,737 | 75.1 | 68,867,681 | 57.3 | 1.7 |
| | 11 | 163,894,182 | 126,172,635 | 77.0 | 86,571,379 | 31.4 | 2.2 |
| | 12 | 152,743,960 | 121,372,255 | 79.5 | 75,991,318 | 37.4 | 1.9 |
| | 13 | 151,999,190 | 113,577,704 | 74.7 | 75,833,684 | 33.2 | 1.9 |
| | 14 | 202,852,675 | 159,675,213 | 78.7 | 117,345,298 | 26.5 | 2.9 |
| | 15 | 141,474,977 | 112,673,941 | 79.6 | 72,672,242 | 35.5 | 1.8 |
| | 16 | 142,268,726 | 115,664,234 | 81.3 | 75,488,660 | 34.7 | 1.9 |

FIG. 37

| Groups | Case no. | Raw reads | Mapped reads | Mappability (%) | Nonduplicated reads | Duplication rate (%) | Sequence Depth |
|---|---|---|---|---|---|---|---|
| Healthy Controls | 17 | 152,891,582 | 121,139,929 | 79.2 | 67,600,448 | 44.2 | 1.7 |
| | 18 | 72,063,850 | 54,830,589 | 76.1 | 39,491,302 | 28.0 | 1.0 |
| | 19 | 102,624,178 | 75,639,416 | 73.9 | 39,343,211 | 48.1 | 1.0 |
| | 20 | 73,026,647 | 56,299,441 | 77.1 | 41,317,154 | 26.6 | 1.0 |
| | 21 | 96,392,731 | 71,852,951 | 72.8 | 55,930,990 | 21.9 | 1.4 |
| | 22 | 168,621,616 | 137,019,620 | 81.3 | 115,916,753 | 15.4 | 2.9 |
| | 23 | 75,634,959 | 58,746,138 | 77.7 | 46,764,110 | 20.4 | 1.2 |
| | 24 | 110,255,565 | 81,307,613 | 73.7 | 67,761,917 | 16.7 | 1.7 |
| | 25 | 102,260,394 | 72,287,645 | 70.7 | 62,608,240 | 13.4 | 1.6 |
| | 26 | 199,671,495 | 159,834,677 | 70.7 | 78,056,894 | 51.2 | 2.0 |
| | 27 | 205,140,024 | 166,513,358 | 70.7 | 131,431,962 | 21.1 | 3.3 |
| | 28 | 207,846,830 | 168,188,748 | 70.7 | 137,596,001 | 18.2 | 3.4 |
| | 29 | 191,182,941 | 154,980,939 | 70.7 | 122,902,907 | 20.7 | 3.1 |
| | 30 | 142,599,302 | 109,911,016 | 70.7 | 80,170,054 | 27.1 | 2.0 |
| | 31 | 181,310,671 | 145,090,367 | 70.7 | 93,229,176 | 35.7 | 2.3 |
| | 32 | 139,872,943 | 112,162,434 | 70.7 | 91,187,231 | 18.7 | 2.3 |
| Lung cancer patients | LC-1 | 172,759,700 | 139,873,272 | 81.0 | 120,046,259 | 14.2 | 3.0 |
| | LC-2 | 192,662,437 | 152,014,403 | 78.9 | 117,805,216 | 22.5 | 2.9 |
| | LC-3 | 189,026,133 | 148,943,046 | 78.8 | 118,315,825 | 20.6 | 3.0 |
| | LC-4 | 169,205,034 | 138,964,558 | 82.1 | 123,818,863 | 10.9 | 3.1 |
| Colorectal cancer patient | CRC-1 | 184,082,571 | 151,144,896 | 82.1 | 124,287,467 | 17.8 | 3.1 |

FIG. 38

METHYLATION PATTERN ANALYSIS OF TISSUES IN A DNA MIXTURE

CROSS-REFERENCES TO RELATED APPLICATIONS

This application claims priority to and is a non-provisional of U.S. Provisional Application 62/026,330, entitled "Determining the Compositions of a DNA Mixture by Tissue-Specific Methylation Pattern Analysis," by Chiu et al., filed Jul. 18, 2014; U.S. Provisional Application 62/158,466, entitled "Determining the Compositions of a DNA Mixture by Tissue-Specific Methylation Pattern Analysis," by Chiu et al., filed May 7, 2015; and U.S. Provisional Application 62/183,669, entitled "Determining the Compositions of a DNA Mixture by Tissue-Specific Methylation Pattern Analysis," by Chiu et al., filed Jun. 23, 2015, which are herein incorporated by reference in their entirety for all purposes. This application is also related to commonly owned PCT Publication WO2014/043763 entitled "Non-Invasive Determination Of Methylome Of Fetus Or Tumor From Plasma," which is herein incorporated by reference in its entirety for all purposes.

BACKGROUND

The analysis of cell-free DNA in plasma has been shown to be useful for different diagnostic purposes including noninvasive prenatal testing and cancer detection. It is believed that the presence of cell-free DNA in plasma is due to the release of DNA from apoptotic cells (Jahr et al. Cancer Res 2001; 61: 1659-1665 and Lo et al. Sci Transl Med. 2010; 2:61ra91.). In previous studies, it has been shown that hematopoietic cells are the major source of plasma DNA in healthy subjects and organ transplant recipients (Lui Y Y et al. Clin Chem 2002; 48:421-7 and Zheng Y W et al. Clin Chem 2012; 58:549-58). In these previous studies, organ transplant models were used to determine the contribution of different organs to the plasma DNA. In those scenarios, the genetic difference between the organ donor and the transplant recipients are used to calculate the contribution of the transplanted organ to the plasma DNA of the transplant recipient. However, in this model, only the contribution of the transplanted organ can be determined and the contribution of the other organs which are from the recipient cannot be determined at the same time.

Further, even for techniques that can determine a contribution from other organs using methylation patterns, the accuracy of such techniques has not been comprehensively tested, and thus deficiencies in accuracy have not been adequately identified. And, the application of the determination of contributions from other organs has been limited.

BRIEF SUMMARY

Embodiments are described for determining the contributions of different tissues to a biological sample that includes a mixture of cell-free DNA molecules from various tissues types, e.g., as occurs in plasma and other body fluids. Embodiments can analyze the methylation patterns of the DNA mixture (e.g., methylation levels at particular genomic sites) and determine fractional contributions of various tissue types to the DNA mixture. Various types of genomic sites can be chosen to have particular properties across tissue types and across individuals, so as to provide increased accuracy in determining contributions of the various tissue types. For example, genomic sites that have at least a threshold amount of variability can be used, as opposed to just using genomic sites that are specific to one tissue type.

In some embodiments, the methylation patterns of the tissue types that potentially contribute to the DNA mixture (candidate tissues) can be determined. Then, the methylation pattern of the DNA mixture of interest is determined. For example, methylation levels can be computed at various sites. As the DNA mixture is composed of the DNA from the candidate tissues, the composition of the DNA mixture can be determined by comparing the methylation patterns of the DNA mixture and the candidate tissue types. For example, methylation levels at N genomic sites can be used to compute a contribution from M tissues, where M is less than or equal to N. The methylation levels at each site can be computed for each tissue. The linear system of equations $Ax=b$ can be solved, where b is a vector of the measured methylation densities at the N sites, x is a vector of the contribution from the M tissues, and A is a matrix of M rows and N columns, with each row providing the methylation densities at the M tissues at the particular site of that row. If M is less than N, then a least squares optimization can be performed.

In various embodiments, a significant separation value (i.e., a subtracted difference or a ratio) in a contribution percentage of a particular tissue type in the DNA mixture relative to a reference value can indicate a diseased state. The reference value may correspond to a contribution percentage determined in a healthy individual, and a separation value greater than a threshold can determine a diseased state, as the diseased tissue releases more cell-free DNA molecules than healthy tissue.

In other embodiments, two fractional contributions of a tissue type can be determined using methylation levels of two sets of cell-free DNA molecules, each set being for a different size range, to identify a classification of whether the tissue type is diseased. A separation value between the two fractional contributions can be compared to a threshold, and a classification can be determined for whether the first tissue type has a disease state based on the comparison. For example, such a technique can identify diseased tissue that releases shorter cell-free DNA molecules by measuring a higher fractional contribution for shorter cell-free DNA molecules than for longer cell-free DNA molecules.

In yet other embodiments, two fractional contributions of a tissue type can be determined using methylation levels of two sets of cell-free DNA molecules, each set being for a different chromosomal region, to identify a classification of whether a first chromosomal region has a sequence imbalance. A separation value between the two fractional contributions can be compared to a threshold, and a classification can be determined for whether the first chromosomal region has a sequence imbalance based on the comparison. For example, regions of different copy number will correspond to different contribution percentages for a tissue type that is the origin of the copy number aberration, as may occur when the tissue type has a tumor with an aberration.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 shows a table of percentage contributions determined from a plasma DNA tissue mapping analysis among pregnant women according to embodiments of the present invention.

FIG. 6 shows a table of percentage contributions from plasma DNA tissue mapping analysis among the non-pregnant healthy control subjects according to embodiments of the present invention.

FIG. 7 shows a table of the estimated contributions of different organs to the plasma DNA for 11 pregnant women and 4 non-pregnant healthy subjects using the first set of markers (with high organ specificity) according to embodiments of the present invention.

FIG. 8 shows a table of the estimated contributions of different organs to the plasma DNA for 11 pregnant women and 4 non-pregnant healthy subjects using the second set of markers (with low organ specificity) according to embodiments of the present invention.

FIG. 10 shows a table 1000 of contributions of different tissues to the plasma DNA of cancer and healthy patients based on organ-specific methylation pattern analysis according to embodiments of the present invention.

FIG. 13 is a table showing plasma DNA tissue mapping analysis among organ transplantation patients according to embodiments of the present invention.

FIG. 19 is a table showing contributions of different tissues to the plasma DNA of patients with various cancers and healthy subjects based on organ-specific methylation pattern analysis according to embodiments of the present invention.

FIG. 20 shows a table shows the contributions of the different organs for each cancer patient compared with the mean of the four control subjects according to embodiments of the present invention.

FIG. 23 is a table showing plasma DNA tissue mapping analysis among cancer patients according to embodiments of the present invention.

FIG. 25 is a table showing the percentage contribution of different organs to the plasma DNA by methylation deconvolution in nine SLE patients according to embodiments of the present invention.

FIGS. 37 and 38 show a table of basic sequencing parameters, including the sequencing depth, of various samples used in identifying a tissue of origin.

Figure 1:
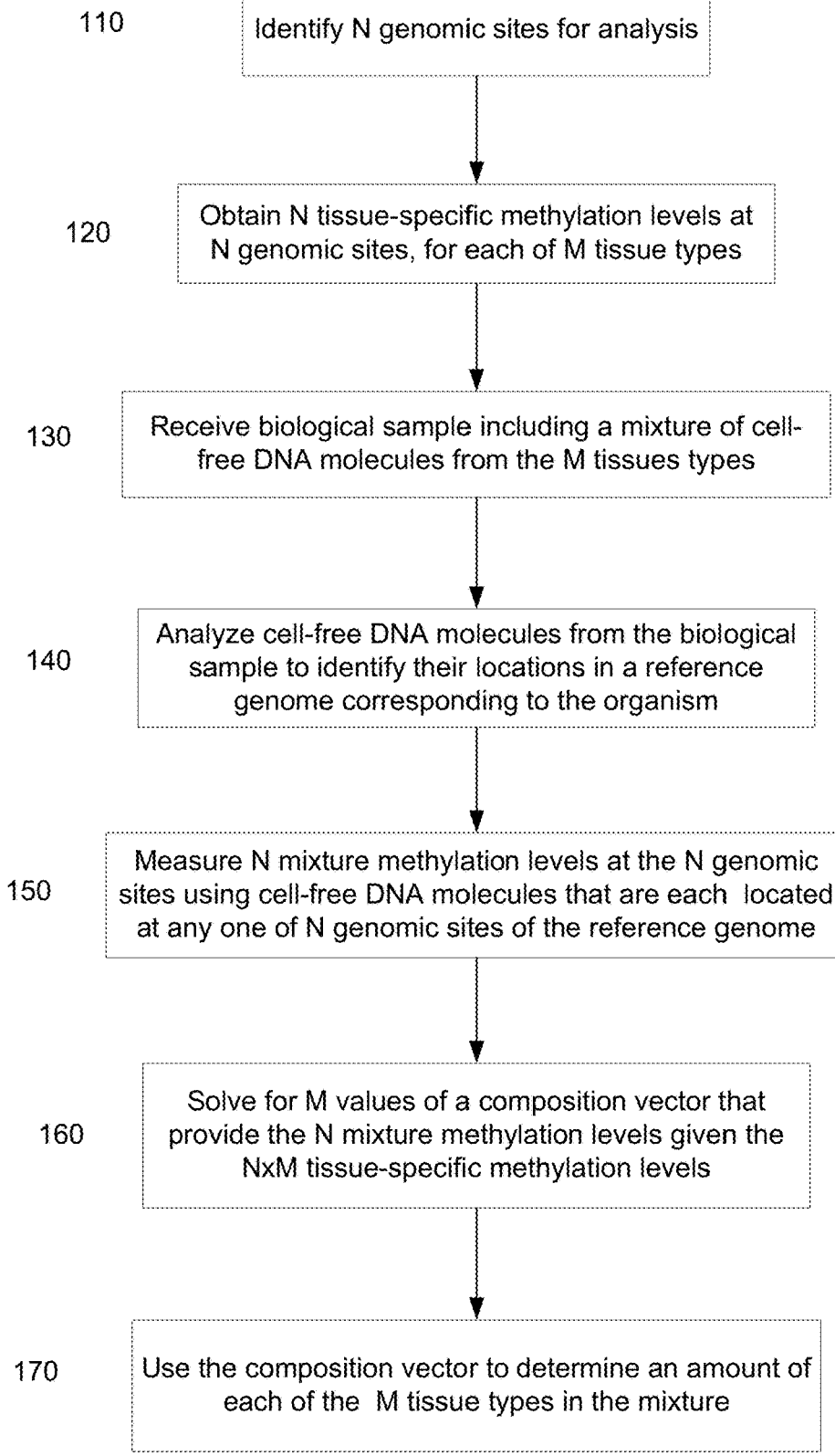
FIG. 1 is a flowchart illustrating a method of analyzing a DNA mixture of cell-free DNA molecules to determine fractional contributions from various tissue types from methylation levels according to embodiments of the present invention.

Appendix A shows table S1 of type I and type II markers.

TERMS

A "methylome" provides a measure of an amount of DNA methylation at a plurality of sites or loci in a genome. The methylome may correspond to all of the genome, a substantial part of the genome, or relatively small portion(s) of the genome. A "fetal methylome" corresponds to a methylome of a fetus of a pregnant female. The fetal methylome can be determined using a variety of fetal tissues or sources of fetal DNA, including placental tissues and cell-free fetal DNA in maternal plasma. A "tumor methylome" corresponds to a methylome of a tumor of an organism (e.g., a human). The tumor methylome can be determined using tumor tissue or cell-free tumor DNA in maternal plasma. The fetal methylome and the tumor methylome are examples of a methylome of interest. Other examples of methylomes of interest are the methylomes of organs (e.g. methylomes of brain cells, bones, the lungs, the heart, the muscles and the kidneys, etc.) that can contribute DNA into a bodily fluid (e.g. plasma, serum, sweat, saliva, urine, genital secretions, semen, stools fluid, diarrheal fluid, cerebrospinal fluid, secretions of the gastrointestinal tract, ascitic fluid, pleural fluid, intraocular fluid, fluid from a hydrocele (e.g. of the testis), fluid from a cyst, pancreatic secretions, intestinal secretions, sputum, tears, aspiration fluids from breast and thyroid, etc.). The organs may be transplanted organs.

A "plasma methylome" is a methylome determined from the plasma or serum of an animal (e.g., a human). The plasma methylome is an example of a cell-free methylome since plasma and serum include cell-free DNA. The plasma methylome is also an example of a mixed methylome since it is a mixture of fetal/maternal methylome or tumor/patient methylome or DNA derived from different tissues or organs. The "placental methylome" can be determined from a chorionic villus sample (CVS) or a placental tissue sample (e.g., obtained following delivery). The "cellular methylome" corresponds to the methylome determined from cells (e.g., blood cells) of the patient. The methylome of the blood cells is called the blood cell methylome (or blood methylome).

A "site" corresponds to a single site, which may be a single base position or a group of correlated base positions, e.g., a CpG site. A "locus" may correspond to a region that includes multiple sites. A locus can include just one site, which would make the locus equivalent to a site in that context.

The "methylation index" for each genomic site (e.g., a CpG site) refers to the proportion of sequence reads showing methylation at the site over the total number of reads covering that site. The "methylation density" of a region is the number of reads at sites within the region showing methylation divided by the total number of reads covering the sites in the region. The sites may have specific characteristics, e.g., being CpG sites. Thus, the "CpG methylation density" of a region is the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g. 50-kb or 1-Mb, etc. A region could be the entire genome or a chromosome or part of a chromosome (e.g. a chromosomal arm). The methylation index of a CpG site is the same as the methylation density for a region when the region only includes that CpG site. The "proportion of methylated cytosines" refers the number of cytosine sites, "C's", that are shown to be methylated (for example unconverted after bisulfite conversion) over the total number of analyzed cytosine residues, i.e. including cytosines outside of the CpG context, in the region. The methylation index, methylation density and proportion of methylated cytosines are examples of "methylation levels."

A "methylation profile" (also called methylation status) includes information related to DNA methylation for a region. Information related to DNA methylation can include, but not limited to, a methylation index of a CpG site, a methylation density of CpG sites in a region, a distribution of CpG sites over a contiguous region, a pattern or level of methylation for each individual CpG site within a region that contains more than one CpG site, and non-CpG methylation. A methylation profile of a substantial part of the genome can be considered equivalent to the methylome. "DNA methylation" in mammalian genomes typically refers to the addition of a methyl group to the 5' carbon of cytosine residues (i.e. 5-methylcytosines) among CpG dinucleotides. DNA methylation may occur in cytosines in other contexts, for example CHG and CHH, where H is adenine, cytosine or thymine. Cytosine methylation may also be in the form of 5-hydroxymethylcytosine. Non-cytosine methylation, such as $N^6$-methyladenine, has also been reported.

A "tissue" corresponds to a group of cells of a same type. Different types of tissue may consist of different types of cells (e.g., hepatocytes, alveolar cells or blood cells), but also may correspond to tissue from different organisms (mother vs. fetus) or to healthy cells vs. tumor cells. "Reference tissues" correspond to tissues used to determine tissue-specific methylation levels. Multiple samples of a same tissue type from different individuals may be used to determine a tissue-specific methylation level for that tissue type.

A "biological sample" refers to any sample that is taken from a subject (e.g., a human, such as a pregnant woman, a person with cancer, or a person suspected of having cancer, an organ transplant recipient or a subject suspected of having a disease process involving an organ (e.g., the heart in myocardial infarction, or the brain in stroke) and contains one or more nucleic acid molecule(s) of interest. The biological sample can be a bodily fluid, such as blood, plasma, serum, urine, vaginal fluid, fluid from a hydrocele (e.g. of the testis), or vaginal flushing fluids, pleural fluid, ascitic fluid, cerebrospinal fluid, saliva, sweat, tears, sputum, bronchoalveolar lavage fluid, etc. Stool samples can also be used.

The term "level of cancer" can refer to whether cancer exists, a stage of a cancer, a size of tumor, whether there is metastasis, the total tumor burden of the body, and/or other measure of a severity of a cancer. The level of cancer could be a number or other indicia, such as symbols, alphabet letters, and colors. The level could be zero. The level of cancer also includes premalignant or precancerous conditions (states) associated with mutations or a number of mutations. The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a patient dying of cancer, or the chance of the cancer progressing after a specific duration or time, or the chance of cancer metastasizing. Detection can mean 'screening' or can mean checking if someone, with suggestive features of cancer (e.g. symptoms or other positive tests), has cancer.

The term "sequence imbalance" of a chromosomal region means any significant deviation in an amount of cell-free DNA molecules from the chromosomal region relative to an expected value, if the organism was healthy. For example, a chromosomal region may exhibit an amplification or a deletion in a certain tissue, thereby resulting in a sequence imbalance for the chromosomal region in a DNA mixture containing DNA from the tissue, mixed with DNA from other tissues. As examples, the expected value can be obtained from another sample or from another chromosomal region that is assumed to be normal (e.g., an amount representative of two copies for a diploid organism). A chromosomal region can be composed of multiple disjoint subregions.

A "type" for a genomic locus (marker) corresponds to specific attributes for a locus across tissue types. The description primarily refers to type I loci and type II loci, whose properties are provided in detail below. A locus of a given type can have specific statistical variation in methylation levels across tissue types. A "category" for a genomic locus (marker) corresponds to specific variation in methylation levels for a locus across different individuals for a same tissue type. A set of genomic loci (markers) can be composed of any number of loci of various types and/or categories. Thus, a set of loci corresponds to loci selected for a particular measurement and does not connote any particular properties of the loci in the set.

A "separation value" corresponds to a difference or a ratio involving two values, e.g., two fractional contributions or two methylation levels. The separation value could be a simple difference or ratio. The separation value can include other factors, e.g., multiplicative factors. As other examples, a difference or ratio of functions of the values can be used, e.g., a difference of the natural logarithms (ln) of the two values.

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1). The term "cutoff" and "threshold" refer to a predetermined number used in an operation. For example, a cutoff size can refer to a size above which fragments are excluded. A threshold value may be a value above or below which a particular classification applies. Either of these terms can be used in either of these contexts.

DETAILED DESCRIPTION

Embodiments of the present invention can determine percentages of cell-free DNA in plasma (or other DNA mixture) from various tissue types using known methylation levels at certain genomic sites for the specific tissue types. For example, methylation levels at the genomic sites can be measured for a liver sample, and these tissue-specific methylation levels can be used to determine how much cell-free DNA in the mixture is from the liver. Methylation levels can also be measured for tissue types that provide substantial contributions to the DNA mixture, so that a predominance (e.g., more than 90%, 95%, or 99%) of the cell-free DNA mixture can be accounted for. Such other samples can include, but not limited to, some or all of the following: lung, colon, small intestines, pancreas, adrenal glands, esophagus, adipose tissues, heart, and brain.

A deconvolution process can be used to determine fractional contributions (e.g., percentage) for each of the tissue types for which tissue-specific methylation levels are known. In some embodiments, a linear system of equations can be created from the known tissue-specific methylation levels and the mixture methylation levels at the specified genomic sites, and the fractional contributions that best approximate the measured mixture methylation levels can be determined (e.g., using least squares).

Specific genomic sites can be selected to provide a desired level of accuracy. For example, genomic sites that have at least a threshold amount of variability can be used, as opposed to just using genomic sites that are specific to one tissue type. A first set (e.g., 10) of the genomic sites can be selected such that each have a coefficient of variation of methylation levels of at least 0.15 across the tissue types and such that each have a difference between a maximum and a minimum methylation level for the M tissue types that exceeds 0.1 for one or more other samples. This first set of genomic sites may not have a specific methylation signature for a specific tissue type, e.g., only or predominantly methylated in the specific tissue type. Such a first set is referred to as type II sites. These genomic sites can be used in combination with genomic sites that do have a specific signature, which are referred to as type I sites.

Using the type II sites can ensure that the full space of methylation levels across the tissue types is spanned by the genomic sites, thereby providing increased accuracy over the type I sites. Just using more type I sites provides redundant basis vectors for the methylation space (i.e., more genomic sites that have the same pattern as other sites), while adding other genomic sites whose methylation levels have various values across different tissues adds new basis vectors for discriminating fractional contributions via the linear system of equations.

Once the fractional contributions are determined (regardless of types of sites chosen), the fractional contributions can be used for various purposes. Reference fractional contributions for the various tissue types can be determined for a particular set of people that are healthy for those tissue types (e.g., healthy individuals for all tissue types or individual healthy for certain tissue types). When a tissue type (e.g., for the liver) is diseased, then that tissue would release more cell-free DNA molecules, as may occur via apoptosis. For example, a substantial increase (i.e., threshold greater than reference values) in the fractional contribution for liver indicates that the liver is diseased.

Such an increase in fractional contribution of a particular tissue type can be subjected to further analysis, e.g., a size analysis of the cell-free DNA. The size analysis can be performed by itself as well. Two fractional contributions can be determined for different size ranges (e.g., short and long), and separations (i.e., difference or ratio) between the two fractional contributions can indicate that there are more short cell-free DNA molecules from the particular tissue type than long cell-free DNA molecules. As a diseased tissue has shorter cell-free DNA molecules, the higher fractional contribution for the shorter cell-free DNA molecules relative to longer cell-free DNA molecules in the particular tissue type indicates that the particular tissue type is diseased.

Separations between fractional contributions for a tissue type using different chromosomal regions can be used to determine whether the tissue type has a sequence imbalance. For an example of a pregnant female where the tissue type is fetal tissue, if there are three copies of chromosome 21, then the percentage of fetal tissue will be measured to be higher using cell-free DNA from chromosome 21 than it will for another chromosome having two copies. A significant separation (e.g., greater than a threshold) in fractional contribution of the fetal tissue indicates that chromosome 21 has a sequence imbalance.

As another example for detecting sequence imbalances, a particular chromosomal region can be identified as having a copy number aberration, but the origin of the aberration may not be known. A region can also be suspected of having an aberration. A first fractional contribution for a tissue type can be determined using cell-free DNA from the identified region, and a second fractional contribution for the tissue type can be determined using cell-free DNA from another region. A significant separation between the fractional contributions indicates that the tissue type is the one exhibiting a sequence imbalance, e.g., the sequence imbalance identified via the copy number aberration or simply a sequence imbalance being tested for the identified region.

I. Composition of DNA Mixture by Methylation Deconvolution

Different tissue types can have different levels of methylation for a genomic site. These differences can be used to determine the fractional contributions of DNA from the various tissue types in a mixture. Thus, the composition of a DNA mixture can be determined by a tissue-specific methylation pattern analysis. The examples below discuss methylation densities, but other methylation levels can be used.

A. Single Genomic Site

The principle of methylation deconvolution can be illustrated using a single methylation genomic site (methylation marker) to determine a composition of a DNA mixture from an organism. Assume that tissue A is completely methylated for the genomic site, i.e. methylation density (MD) of 100% and tissue B is completely unmethylated, i.e. MD of 0%. In this example, methylation density refers to the percentage of cytosine residues with the context of CpG dinucleotides being methylated in the region of interest.

If the DNA mixture C is composed of tissue A and tissue B and the overall methylation density of the DNA mixture C is 60%, we can deduce the proportional contribution of tissues A and B to the DNA mixture C according to the following formula:

$$MD_C = MD_A \times a + MD_B \times b,$$

where $MD_A$, $MD_B$, $MD_C$ represent the MD of tissues A, tissue B and the DNA mixture C, respectively; and a and b are the proportional contributions of tissues A and B to the DNA mixture C. In this particular example, it is assumed that tissues A and B are the only two constituents of the DNA mixture. Therefore, a+b=100%. Thus, it is calculated that tissues A and B contribute 60% and 40%, respectively, to the DNA mixture.

The methylation densities in tissue A and tissue B can be obtained from samples of the organism or from samples from other organisms of the same type (e.g., other humans, potentially of a same subpopulation). If samples from other organisms are used, a statistical analysis (e.g., average, median, geometric mean) of the methylation densities of the samples of tissue A can be used to obtain the methylation density $MD_A$, and similarly for $MD_B$.

Genomic site can be chosen to have minimal inter-individual variation, for example, less than a specific absolute amount of variation or being within a lowest portion of genomic sites tested. For instance, for the lowest portion, embodiments can select only genomic sites having the lowest 10% of variation among a group of genomic sites tested. The other organisms can be taken from healthy persons, as well as those with particular physiologic (e.g. pregnant women, or people with different ages or people of a particular sex), which may correspond to a particular subpopulation that includes the current organism being tested.

The other organisms of a subpopulation may also have other pathologic conditions (e.g. patients with hepatitis or diabetes, etc.). Such a subpopulation may have altered tissue-specific methylation patterns for various tissues. The methylation pattern of the tissue under such disease condition can be used for the deconvolution analysis in addition to using the methylation pattern of the normal tissue. This deconvolution analysis may be more accurate when testing an organism from such a subpopulation with those conditions. For example, a cirrhotic liver or a fibrotic kidney may have a different methylation pattern compared with a normal liver and normal kidney, respectively. Thus, if a patient with liver cirrhosis was screened for other diseases, it can be more accurate to include a cirrhotic liver as one of the candidates contributing DNA to the plasma DNA, together with the healthy tissues of other tissue types.

B. Multiple Genomic Sites

More genomic sites (e.g., 10 or more) may be used to determine the constitution of the DNA mixture when there are more potential candidate tissues. The accuracy of the estimation of the proportional composition of the DNA mixture is dependent on a number of factors including the number of genomic sites, the specificity of the genomic sites (also called "sites") to the specific tissues, and the variability of the sites across different candidate tissues and across different individuals used to determine the reference tissue-specific levels. The specificity of a site to a tissue refers to the difference in the methylation density of the genomic sites between the particular tissue and other tissue types.

The larger the difference between their methylation densities, the more specific the site to the particular tissue would be. For example, if a site is completely methylated in the liver (methylation density=100%) and is completely unmethylated in all other tissues (methylation density=0%), this site would be highly specific for the liver. Whereas, the variability of a site across different tissues can be reflected by, for example, but not limited to, the range or standard deviation of methylation densities of the site in different types of tissue. A larger range or higher standard deviation would allow a more precise and accurate determination of the relative contributions of the different organs to the DNA mixture mathematically. The effects of these factors on the accuracy of estimating the proportional contribution of the candidate tissues to the DNA mixture are illustrated in the later sections of this application.

Here, we use mathematical equations to illustrate the deduction of the proportional contribution of different organs to the DNA mixture. The mathematical relationship between the methylation densities of the different sites in the DNA mixture and the methylation densities of the corresponding sites in different tissues can be expressed as:

$$\overline{MD}_i = \Sigma_k(p_k \times MD_{ik}),$$

where $\overline{MD}_i$ represents the methylation density of the site i in the DNA mixture; $p_k$ represents the proportional contribution of tissue k to the DNA mixture; $MD_{ik}$ represents the methylation density of the site i in the tissue k. When the number of sites is the same or larger than the number of organs, the values of individual $p_k$ can be determined. The tissue-specific methylation densities can be obtained from other individuals, and the sites can be chosen to have minimal inter-individual variation, as mentioned above.

Additional criteria can be included in the algorithm to improve the accuracy. For example, the aggregated contribution of all tissues can be constrained to be 100%, i.e.

$$\Sigma_k p_k = 100\%.$$

Furthermore, all the organs' contributions can be required to be non-negative:

$$p_k \geq 0, \forall k$$

Due to biological variations, the observed overall methylation pattern may not be completely identical to the methylation pattern deduced from the methylation of the tissues. In such a circumstance, mathematical analysis would be required to determine the most likely proportional contribution of the individual tissues. In this regard, the difference between the observed methylation pattern in the DNA and the deduced methylation pattern from the tissues is denoted by W.

$$W = O - \sum_k (p_k \times M_k)$$

where O is the observed methylation pattern for the DNA mixture and $M_k$ is the methylation pattern of the individual tissue k. $p_k$ is the proportional contribution of tissue k to the DNA mixture. The most likely value of each $p_k$ can be determined by minimizing W, which is the difference between the observed and deduced methylation patterns. This equation can be resolved using mathematical algorithms, for example by using quadratic programming, linear/non-linear regression, expectation-maximization (EM) algorithm, maximum likelihood algorithm, maximum a posteriori estimation, and the least squares method.

C. Method of Methylation Deconvolution

As described above, a biological sample including a mixture of cell-free DNA molecules from an organism can be analyzed to determine the composition of the mixture, specifically the contributions from different tissue types. For example, the percentage contribution of the cell-free DNA molecules from the liver can be determined. These measurements of the percentage contributions in the biological sample can be used to make other measurements of the biological sample, e.g., identifications of where a tumor is located, as is described in later sections.

FIG. 1 is a flowchart illustrating a method 100 of analyzing a DNA mixture of cell-free DNA molecules to determine fractional contributions from various tissue types from methylation levels according to embodiments of the present invention. A biological sample includes a mixture of cell-free DNA molecules from M tissues types. The biological sample can be any one of various examples, e.g., as mentioned herein. The number M of tissue types is greater than two. In various embodiments, M can be 3, 7, 10, 20, or more, or any number in between. Method 100 can be performed using a computer system.

At block 110, N genomic sites are identified for analysis. The N genomic sites can have various attributes, e.g., as described in more detail in section II, which describes type I and type II genomic sites. As examples, the N genomic sites can include type I or type II sites only, or a combination of both. The genomic sites can be identified based on analyses of one or more other samples, e.g., based on data obtained from databases about methylation levels measured in various individuals.

In some embodiments, at least 10 of the N genomic sites are type II and each have a coefficient of variation of methylation levels of at least 0.15 across the M tissue types. A more stringent threshold for the coefficient of variation can be used, e.g., 0.25. The at least 10 genomic sites can also each have a difference between a maximum and a minimum methylation level for the M tissue types that exceeds 0.1. A more stringent threshold for the coefficient of variation can be used, e.g., 0.2. The N genomic sites can also include type I sites (e.g., at least 10).

These methylation properties of the genomic loci can be measured for one sample or a set of samples. The set of samples may be for a subpopulation of organisms that includes the instant organism being tested, e.g., a subpopulation having a particular trait that is shared with the instant organism. These other samples can be referred to as reference tissues, and different reference tissues may be used from different samples.

At block 120, N tissue-specific methylation levels are obtained at the N genomic sites for each of M tissue types. N is greater than or equal to M, so that the tissue-specific methylation levels can be used in the deconvolution to determine the fractional percentages. The tissue-specific methylation levels can form a matrix A of dimensions N by M. Each column of the matrix A can correspond to a methylation pattern for a particular tissue type, where the pattern is of methylation levels at the N genomic sites.

In various embodiments, the tissue-specific methylation patterns can be retrieved from public database(s) or previous studies. In examples herein, the methylation data for neutrophils and B cells were downloaded from the Gene Expression Omnibus (Hodges et al. Mol Cell 2011; 44:17-28). Methylation patterns for other tissues (hippocampus, liver, lung, pancreas, atrium, colon (including its various parts, e.g. sigmoid colon, transverse colon, ascending colon, descending colon), adrenal gland, esophagus, small intestines and CD4 T cell) were downloaded from the RoadMap Epigenomics project (Ziller et al. Nature 2013; 500:477-81). The methylation patterns for the buffy coat, placenta, tumor and plasma data were from published reports (Lun et al. Clin Chem. 2013; 59:1583-94; Chan et al. Proc Natl Acad Sci USA. 2013; 110:18761-8). These tissue-specific methylation patterns can be used to identify the N genomic sites to be used in the deconvolution analysis.

At block 130, the biological sample including a mixture of cell-free DNA molecules from the M tissues types is received. The biological sample may be obtained from the patient organism in a variety of ways. The manner of obtaining such samples may be non-invasive or invasive. Examples of non-invasively obtained samples include certain types of fluids (e.g. plasma or serum or urine) or stools. For instance, plasma includes cell-free DNA molecules from many organ tissues, and is thus useful for analyzing many organs via one sample.

At block 140, cell-free DNA molecules from the biological sample are analyzed to identify their locations in a reference genome corresponding to the organism. For example, the cell-free DNA molecules can be sequenced to obtain sequence reads, and the sequence reads can be mapped (aligned) to the reference genome. If the organism was a human, then the reference genome would be a reference human genome, potentially from a particular subpopulation. As another example, the cell-free DNA molecules can be analyzed with different probes (e.g., following PCR or other amplification), where each probe corresponds to a different genomic site. In some embodiments, the analysis of the cell-free DNA molecules can be performed by receiving sequence reads or other experimental data corresponding to the cell-free DNA molecules, and then analyzing the experimental data.

A statistically significant number of cell-free DNA molecules can be analyzed so as to provide an accurate deconvolution for determining the fractional contributions from the M tissue types. In some embodiments, at least 1,000 cell-free DNA molecules are analyzed. In other embodiments, at least 10,000 or 50,000 or 100,000 or 500,000 or 1,000,000 or 5,000,000 cell-free DNA molecules or more can be analyzed. The total number of molecules to analyze can depend on M and N, and the desired precision (accuracy).

At block 150, N mixture methylation levels are measured at the N genomic sites using a first group of cell-free DNA molecules that are each located at any one of N genomic sites of the reference genome. The N mixture methylation levels refer to methylation levels in the mixture of the biological sample. As an example, if a cell-free DNA molecule from the mixture is located at one of the N genomic sites, then a methylation index for that molecule at the site can be included in an overall methylation density for that site. The N mixture methylation levels can form a methylation vector b of length N, where b corresponds to observed values from which the fractional contributions of the tissue types can be determined.

In one embodiment, the methylation levels for the genomic sites in the DNA mixture can be determined using whole genome bisulfite sequencing. In other embodiments, the methylation levels for the genomic sites can be determined using methylation microarray analysis, such as the Illumina HumanMethylation450 system, or by using methylation immunoprecipitation (e.g. using an anti-methylcytosine antibody) or treatment with a methylation-binding protein followed by microarray analysis or DNA sequencing, or by using methylation-sensitive restriction enzyme treatment followed by microarray or DNA sequencing, or by using methylation aware sequencing e.g. using a single molecule sequencing method (e.g. by a nanopore sequencing (Schreiber et al. Proc Natl Acad Sci 2013; 110: 18910-18915) or by the Pacific Biosciences single molecule real time analysis (Flusberg et al. Nat Methods 2010; 7: 461-465)). Tissue-specific methylation levels can be measured in a same way. As other example, targeted bisulfite sequencing, methylation-specific PCR, non-bisulfite based methylation-aware sequencing (e.g. by single molecule sequencing platforms (Powers et al. Efficient and accurate whole genome assembly and methylome profiling of *E. coli*. BMC Genomics. 2013; 14:675) can be used for the analysis of the methylation level of the plasma DNA for plasma DNA methylation deconvolution analysis. Accordingly, methylation-aware sequencing results can be obtained in a variety of ways.

At block 160, M values of a composition vector are determined. Each M value corresponds to a fractional contribution of a particular tissue type of the M tissue types to the DNA mixture. The M values of the composition vector can be solved to provide the N mixture methylation levels (e.g., methylation vector b) given the N×M tissue-specific methylation levels. The M fractional contributions can correspond to a vector x that is determined by solving Ax=b. When N is greater than M, the solution can involve a minimization of errors, e.g., using least-squares.

At block 170, the composition vector is used determine an amount of each of the M tissue types in the mixture. The M values of the composition vector may be taken directly as the fractional contributions of the M tissue types. In some implementations, the M values can be converted to percentages. Error terms can be used to shift the M values to higher or lower values. Each of the values of the composition vector can be considered a component, and a first component can correspond to a first tissue type.

D. Applications

As mentioned above, the fractional contributions can be used in further measurements of the biological sample and other determinations, e.g., whether a particular chromosomal region has a sequence imbalance or whether a particular tissue type is diseased.

Figure 2:
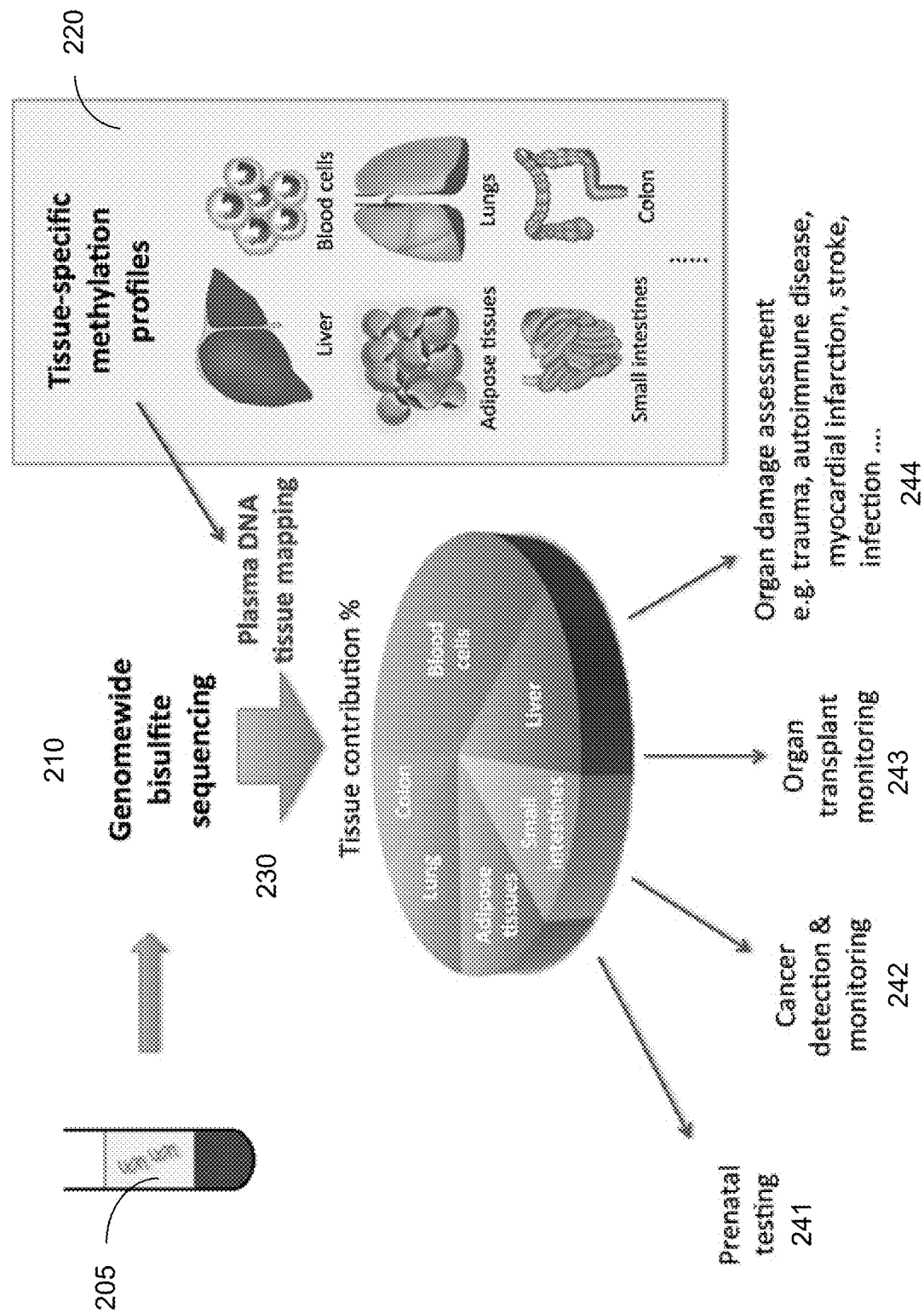
FIG. 2 shows a schematic diagram showing several potential applications of DNA methylation deconvolution (e.g., using plasma) and its applications according to embodiments of the present invention.

FIG. 2 shows a schematic diagram showing several potential applications of DNA methylation deconvolution (e.g., using plasma) according to embodiments of the present invention. In FIG. 2, a biological sample 205 is subjected to genome-wide bisulfite sequencing at 210. At 230, plasma DNA tissue mapping uses tissue-specific methylation profiles 220 to determine tissue contribution percentages. Example tissue-specific methylation profiles are shown as liver, blood cells, adipose tissues, lungs, small intestines, and colon. The contribution percentages can be determined as described above and elsewhere, e.g., solving Ax=b. Examples of applications include prenatal testing 241, cancer detection and monitoring 242, organ transplant monitoring 243, and organ damage assessment 244.

A list of methylation markers (genomic sites) that are useful for determining the contributions of different organs to the plasma DNA can be identified by comparing the methylation profiles (FIG. 2) of different tissues, including the liver, lungs, esophagus, heart, pancreas, sigmoid colon, small intestines, adipose tissues, adrenal glands, colon, T cells, B cells, neutrophils, brain and placenta. In various examples, whole genome bisulfite sequencing data for the liver, lungs, esophagus, heart, pancreas, colon, small intestines, adipose tissues, adrenal glands, brain and T cells were retrieved from the Human Epigenome Atlas from the Baylor College of Medicine (genboree.org/epigenomeatlas/index.rhtml). The bisulfite sequencing data for B cells and neutrophils were from the publication by Hodges et al. (Hodges et al; Directional DNA methylation changes and complex intermediate states accompany lineage specificity in the adult hematopoietic compartment. Mol Cell 2011; 44: 17-28). The bisulfite sequencing data for the placenta were from Lun et al (Lun et al. Clin Chem 2013; 59:1583-94). In other embodiments, markers can be identified from datasets generated using microarray analyses, e.g. using the Illumina Infinium HumanMethylation450 BeadChip Array.

II. Selection of Methylation Markers

Above, we have described the principle of using methylation analysis to determine the composition of a DNA mixture. In particular, the percentage contribution of different organs (or tissues) to the plasma DNA can be determined using methylation analysis. In this section, we further describe the method for the selection of methylation markers and clinical applications of this technology.

The results of determining the composition of the DNA mixture by methylation analysis are affected by the methylation markers used for the deconvolution of the composition of the DNA mixture. Thus, the selection of appropriate genomic methylation markers can be important for the accurate determination of the constitution of the DNA mixture.

A. Criteria for a Methylation Marker for Deconvolution

For marker selection, the following three attributes may be considered. (i) It is desirable for a methylation marker to have a low variability in the methylation level measured in the same tissue type across different individuals. As the determination of the composition of the DNA mixture is dependent on the recognition of the tissue-specific methylation patterns, the low variability in methylation level in the same tissue type across different individuals would be useful for accurate identification of the tissue-specific patterns in the DNA mixture. In embodiments where the tissue-specific methylation levels are obtained from samples of other organisms (e.g., from a database), the low variability means that the methylation levels from the other samples are similar to the tissue-specific methylation levels for the current organism being tested.

(ii) It is desirable for a methylation marker to have a high variability in methylation levels across different tissues. For a particular marker, a higher difference in the methylation levels across different tissues can provide a more precise determination of the contribution of different tissues to the DNA mixture. In particular, an improvement in precision can be obtained by using one set of markers having attribute (ii) and another set of markers having attribute (iii).

(iii) It is desirable for a methylation marker to have a particularly different methylation level in a particular tissue when compared with those from most or all of the other tissues. In contrast to point (ii) above, a marker can have low variability in the methylation level of most tissues but its methylation level in one particular tissue is different from most of the other tissues. This marker would be particularly useful for the determination of the contribution of the tissue that has a different methylation level from other tissues.

B. Example

A principle of marker selection is illustrated in the following hypothetical examples in table 1.

TABLE 1

Methylation densities in different tissues for 6 hypothetical methylation markers.

| | Marker 1 | Marker 2 | Marker 3 | Marker 4 | Marker 5 | Marker 6 |
|---|---|---|---|---|---|---|
| Liver 1 | 20% | 69% | 9% | 9% | 10% | 90% |
| Liver 2 | 50% | 70% | 10% | 10% | 10% | 90% |
| Liver 3 | 90% | 71% | 11% | 11% | 10% | 90% |
| Heart | 20% | 20% | 30% | 13% | 12% | 12% |
| Lung | 30% | 30% | 60% | 17% | 14% | 84% |
| Colon | 40% | 40% | 90% | 20% | 80% | 80% |

In this hypothetical example, marker 2 has lower variability in methylation density in the liver from three individuals when compared with marker 1. Therefore, marker 2 is superior to marker 1 as a signature for determining the contribution of the liver in a DNA mixture.

Compared with marker 4, marker 3 has a higher variability in methylation density across different tissue types. The same level of change in the estimated contribution from the different tissues would provide a bigger change in the deduced methylation density of the DNA mixture for marker 3 than for marker 4 according to the mathematical relationship discussed above. Therefore, the estimation of the contribution of each tissue can be more precise with marker 3.

Marker 5 has a low variability in methylation density across the liver, heart and lung. Their methylation densities vary from 10% to 14%. However, the methylation density of colon is 80%. This marker would be particularly useful for determining the contribution of the colon in the DNA mixture. Similarly, the heart is hypomethylated compared with the other tissues for marker 6. Therefore, the contribution of the heart can be accurately determined by marker 6. Thus, the combination of markers 5 and 6 would be able to accurately determine the contributions of the colon and the heart. The addition of markers 2 and 3 would then be sufficient to deduce the contribution of each of the four organs, including the liver, heart, lung and colon.

C. Different Types of Markers

A methylation marker may not necessarily need to have all of the above three attributes. A type I methylation marker would typically have attribute (iii) above. A number of such markers may also have attribute (i). On the other hand, a type II methylation marker would typically have attribute (ii) above. A number of such markers may also have attribute (i). It is also possible that a particular marker may have all three attributes.

In some embodiments, markers are broadly divided into two types (type I and type II). Type I markers have tissue specificity. The methylation level of these markers for a particular group of one or more tissues is different from most of the other tissues. For example, a particular tissue can have a significant methylation level compared with the methylation level of all the other tissues. In another example, two tissues (e.g., tissue A and tissue B) have similar methylation levels, but the methylation levels of tissues A and B are significantly different from those of the remaining tissues.

Type II markers have a high inter-tissue methylation variability. The methylation levels of these markers are highly variable across different tissues. A single marker in this category may not be sufficient to determine the contribution of a particular tissue to the DNA mixture. However, a combination of type II markers, or in combination with one or more type I markers can be used collectively to deduce the contribution of individual tissues. Under the above definition, a particular marker can be a type I marker only, a type II marker only, or be simultaneously both a type I and type II marker.

1. Type I Markers

In one embodiment, a type I marker can be identified by comparing the methylation density of the marker with the mean and standard deviation (SD) of methylation densities of this particular marker for all candidate tissues. In one implementation, a marker is identified if its methylation density in one tissue is different from the mean of all the tissues by 3 standard deviations (SD).

The methylation profiles of 14 tissues obtained from sources mentioned above were studied to select markers. In one analysis, a total of 1,013 type I markers were identified (markers labeled type I in Table S1 of Appendix A) using the above criteria. In other embodiments, other cutoffs between the particular tissues and the mean methylation densities can be used, for example, 1.5 SD, 2 SD, 2.5 SD, 3.5 SD and 4 SD. In yet another embodiment, a type I marker can identified through the comparison of the methylation density of the particular tissue to the median methylation density of all tissues.

In other embodiments, the type I markers can be obtained when more than one tissue (e.g., two, three, four or five tissues) show significantly different methylation densities than the mean methylation density of all the candidate tissues. In one implementation, a cutoff methylation density can be calculated from the mean and SD of the methylation densities of all the candidate tissues. For illustration purpose, the cutoff (threshold level) can be defined as 3 SD higher or lower than the mean methylation densities. Thus, a marker can be selected when the methylation densities of a specified number of tissues are more than 3 SD higher than the mean methylation density or more than 3 SD lower than the mean methylation density of the tissues.

2. Type II Markers

For identification of type II markers, the mean and SD of methylation densities across all 14 candidate tissues were calculated and the ratio of SD to the mean was denoted as the coefficient of variation (CV). In this illustrative example, we used a cutoff of >0.25 for the CV to identify the qualified type II markers, as well as the difference between the maximum and minimum methylation densities for the group of tissues exceeding 0.2. Using these criteria, 5820 type II markers were identified (markers labeled type II in Table S1 of Appendix A). Other examples of cutoffs for the CV include 0.15, 0.2, 0.3 and 0.4. Other examples of cutoffs for the difference between the maximum and minimum methylation densities include 0.1, 0.15, 0.25, 0.3, 0.35, 0.4, 0.45 and 0.5.

In other embodiments, the average values across multiple samples of the same tissue type can be used to measure a variation of the methylation levels across different tissues. For example, 10 methylation levels of a same genomic site from 10 samples can be averaged to obtain a single methylation level for the genomic site. A similar process can be performed to determine average methylation levels for other tissue types for the genomic site. The average values across tissue types can then be used for determining whether the genomic site has significant variation across tissue types. Other statistical values can be used besides an average, e.g., a median or a geometric mean. Such statistical values can be used to identify type I and/or type II markers.

The different samples of a same tissue type (e.g., from different individuals) can be used to determine a variation of methylation levels across the different samples. Thus, if there are multiple samples of the same tissue type, embodiments can further measure the variation of a particular marker amongst such samples of the same tissue type. A marker with a low variation across samples would be a more reliable marker than one with a high variation.

Embodiments are also directed to the markers in table S1 and the use of any combination of the markers, e.g., using any 10 or more markers of type I or type II in table S1, as well as any combination of 10 or more from each table. For example, embodiments are directed to using 50 (or 100, 250, 500, or 1,000) markers of type I and 50 (or 100, 250, 500, 1,000, 2,000, or 5,000) markers of type II from table S1.

D. Different Categories of Markers

A "category" for a genomic locus (methylation marker) corresponds to specific variation in methylation levels for a locus across different individuals for a same tissue type. Different categories can have different ranges of variation among a particular tissue type across individuals. A first category of methylation markers might have a difference of 10% in the methylation levels or lower among the individuals tested. A second category of methylation markers might have a difference of more than 10% in the methylation levels among the individuals tested. The use of methylation markers with low inter-individual variations (first category markers) would potentially improve the accuracy of determining the contribution of the particular organ in the DNA mixture.

E. Identification of Potential Methylation Markers

In some embodiments, potential methylation markers were identified in the following manner. Such potential methylation markers can then be subjected to the above criteria to identify type I and type II markers. In other embodiments, an identification of type I or type II is not needed. And, other embodiments may use other techniques to identify potential methylation markers.

In some embodiments, all CpG islands (CGIs) and CpG shores on autosomes were considered for potential methylation markers. CGIs and CpG shores on sex chromosomes were not used so as to minimize variation in methylation levels related to the sex-associated chromosome dosage difference in the source data. CGIs were downloaded from the University of California, Santa Cruz (UCSC) database (genome.ucsc.edu/, 27,048 CpG islands for the human genome) (Kent et al. The human genome browser at UCSC. Genome Res. 2002; 12(6):996-1006) and CpG shores were defined as 2 kb flanking windows of the CpG islands (Irizarry et al. The human colon cancer methylome shows similar hypo- and hypermethylation at conserved tissue-specific CpG island shores. Nat Genet 2009; 41(2):178-186). Then, the CpG islands and shores were subdivided into non-overlapping 500 bp units and each unit was considered as a potential methylation marker.

The methylation densities (i.e., the percentage of CpGs being methylated within a 500 bp unit) of all the potential loci were compared between the 14 tissue types. As previously reported (Lun et al. Clin Chem. 2013; 59: 1583-94), the placenta was found to be globally hypomethylated when compared with the remaining tissues. Thus, the methylation profile of the placenta was not included at the marker identification phase. Using the methylation profiles of the remaining 13 tissue types, the two types of methylation markers were identified. For example, type I markers can refer to any genomic sites with methylation densities that are 3 SD below or above in one tissue when compared with the mean level of the 13 tissue types. Type II markers can considered highly variable when (A) the methylation density of the most hypermethylated tissue is at least 20% higher than that of the most hypomethylated one; and (B) the SD of the methylation densities across the 13 tissue types when divided by the mean methylation density (i.e. the coefficient of variation) of the group is at least 0.25. Lastly, in order to reduce the number of potentially redundant markers, only one marker may be selected in one contiguous block of two CpG shores flanking one CpG island.

F. Selection Based on Application

The set of methylation markers chosen for particular applications can be varied depending on the parameters of the desired applications. For example, for determining the origin of a genomic aberration (e.g. copy number aberration (CNA)), a large number of markers spread across the genome would be advantageous. As another example, for applications in which the release of DNA from a particular tissue into plasma is of special significance, one can select a preferentially larger number of methylation markers that are differentially methylated in this tissue type (e.g. type I marker) when compared with the others in the marker set.

The number and choice of methylation markers in the deconvolution analysis can be varied according to the intended use. If the fractional contribution of the liver is of particular interest, e.g. in a patient who has received a liver transplant, more type I liver specific markers can be used in the deconvolution analysis to increase the precision of the quantification of the contribution of the transplanted liver to the plasma DNA.

III. Composition Accuracy

As described above, embodiments can identify the tissue contributors of plasma DNA. In various examples, genome-wide bisulfite sequencing of plasma DNA was performed and analyzed with reference to methylation profiles of different tissues. Using quadratic programming as an example, the plasma DNA sequencing data were deconvoluted into proportional contributions from different tissues. Embodiments were tested for pregnant women, patients with hepatocellular, lung and colorectal carcinoma, and subjects following bone marrow and liver transplantation.

In most subjects, white blood cells were the predominant contributors to the circulating DNA pool. The placental contributions in pregnant women correlated with the proportional contributions as revealed by fetal-specific genetic markers. The graft-derived contributions to the plasma in the transplant recipients correlated with those determined using donor-specific genetic markers. Patients with hepatocellular, lung or colorectal cancer showed elevated plasma DNA contributions from the organ with the tumor. The liver contributions in hepatocellular carcinoma patients also correlated with measurements made using tumor-associated copy number aberrations.

In cancer patients and in pregnant women exhibiting copy number aberrations in plasma, methylation deconvolution pinpointed the tissue type responsible for the aberrations. In a pregnant woman diagnosed as having follicular lymphoma during pregnancy, methylation deconvolution indicated a grossly elevated contribution from B-cells into the plasma DNA pool and localized B-cells (instead of the placenta) as the origin of the copy number aberrations observed in plasma. Accordingly, embodiments may serve as a powerful tool for assessing a wide range of physiological and pathological conditions based on the identification of perturbed proportional contributions of different tissues into plasma.

A. Contribution of Different Types of Blood Cells

As an example of the methylation deconvolution, we determined the contribution of different tissues and cell types to the circulating DNA. Two blood samples were collected from two patients suffering from systemic lupus erythematosus (SLE). After collection, the venous blood samples were centrifuged at 1,500 g for 10 minutes. After centrifugation, the blood cells and the plasma were separated. DNA was then extracted from the blood cells. The DNA was bisulfate converted and sequenced using one lane of a flow cell in a HiSeq2000 sequencer. Two blood cell samples were analyzed using the cell-type-specific methylation pattern analysis. The methylation patterns of neutrophils, lymphocytes, the esophagus, colon, pancreas, liver, lung, heart, adrenal glands and hippocampus were included as potential candidates of the blood cell DNA. 609 methylation markers were selected for the analysis. The whole blood samples of the two subjects were also sent for cell counting to determine the fractional composition of the neutrophils and lymphocytes of the blood cells.

TABLE 2

Blood tissue contributions by deconvolution pattern analysis and cell counting

| | Blood sample 1 | | Blood sample 2 | |
|---|---|---|---|---|
| | Cell type-specific methylation pattern analysis | Blood cell counting | Cell type-specific methylation pattern analysis | Blood cell counting |
| Neutrophils | 90.5% | 93.6% | 89.4% | 89.9% |
| Lymphocytes | 9.5% | 6.4% | 10.6% | 10.1% |
| Esophagus | 0% | — | 0% | — |
| Colon | 0% | — | 2% | — |
| Pancreas | 0% | — | 0% | — |
| Liver | 0% | — | 1% | — |
| Lung | 1% | — | 1% | — |
| Heart | 0% | — | 3% | — |
| Adrenal gland | 0% | — | 0% | — |
| Hippocampus | 0% | — | 0% | — |

For methylation pattern analysis, neutrophils and lymphocytes were determined as the major components constituting the blood cell DNA. The relative proportion of the contribution of neutrophils and lymphocytes resemble their relative abundance in the blood samples according to the cell counting analysis.

B. Pregnant Women

The contributions of different tissues, including the liver, lung, pancreas, colon, hippocampus, small intestines, blood cells, heart, adrenal gland, esophagus and placenta, were analyzed using methylation analysis of the plasma DNA of pregnant women. As the placental genotype is in general identical to the fetus's genotype but different from the pregnant woman's genotype, the precise contribution of the placenta to the maternal plasma can be accurately determined by counting the number of fetal specific-alleles in the sample.

1. Composition and Correlation to Fetal DNA Percentage

Genome-wide bisulfite sequencing of plasma DNA was performed for 15 pregnant women, five from each of first, second and third trimesters. Methylation deconvolution was performed and the percentage contributions from different tissues were deduced. The contributions of different organs were determined based on the methylation levels (such as methylation densities) of all the type I and type II markers in table S1 using quadratic programming analysis.

Figure 3A:
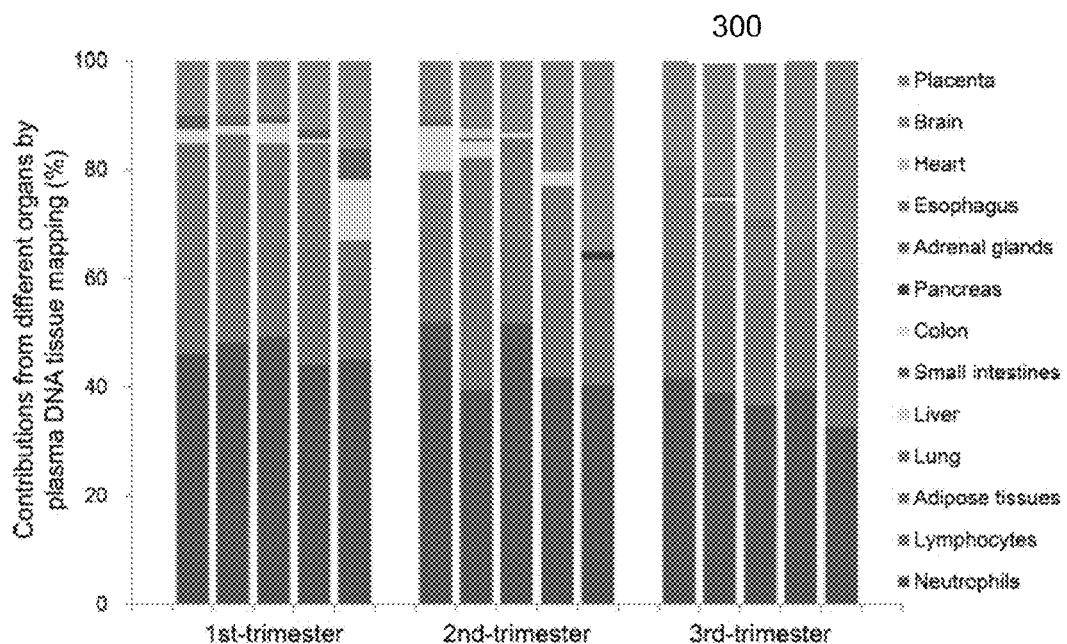
FIG. 3A shows a graph of percentage contributions of different organs to plasma DNA for 15 pregnant women according to embodiments of the present invention.

FIG. 3A shows a graph 300 of percentage contributions of different organs to plasma DNA for 15 pregnant women according to embodiments of the present invention. Each bar corresponds to the results of one sample. The different colors represent the contributions of different organs into plasma. These results show that the white blood cells (i.e. neutrophils and lymphocytes) are the most important contributors to the plasma DNA pool. This observation is consistent with those previously obtained following bone marrow transplantation (Lui Y Y et al. Clin Chem 2002; 48: 421-7).

FIG. 4 shows a table 400 of percentage contributions determined from a plasma DNA tissue mapping analysis among pregnant women according to embodiments of the present invention. These results also show that the placenta is another key contributor of the plasma DNA in pregnant women, with fractional concentrations from 9.9% to 38.4%.

We also measured the placental contributions using paternally-inherited fetal single nucleotide polymorphism (SNP) alleles that were not possessed by the pregnant women. To analyze the fetal-specific SNP alleles, the genotypes of the fetuses were determined by analyzing the chorionic villus samples or the placenta. The genotypes of the pregnant women were determined by analyzing the blood cells. The SNP-based results show the independent validation of the methylation deconvolution results.

Figure 3B:
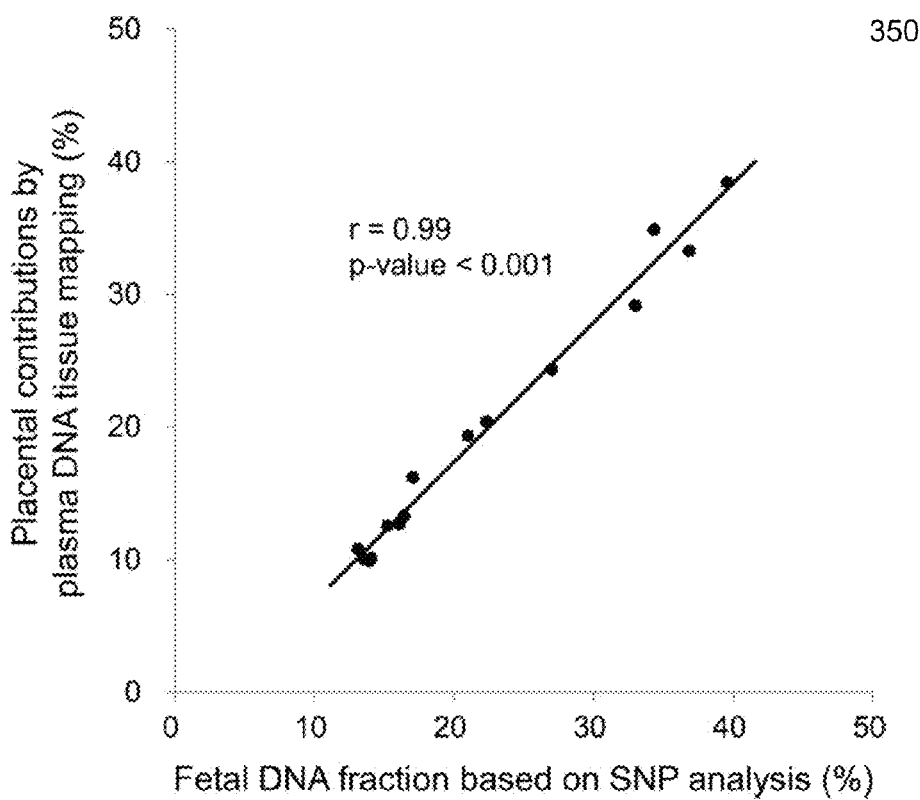
FIG. 3B shows a plot 350 of a correlation between the plasma DNA fractions contributed by the placenta deduced from plasma DNA methylation deconvolution and the fetal DNA fractions deduced using fetal-specific SNP alleles according to embodiments of the present invention.

FIG. 3B shows a plot 350 of a correlation between the plasma DNA fractions contributed by the placenta deduced from plasma DNA methylation deconvolution and the fetal DNA fractions deduced using fetal-specific SNP alleles according to embodiments of the present invention. Plot 350 shows that the placental contributions determined by methylation deconvolution has a strong correlation with the fetal DNA fractions measured using SNPs (r=0.99, p<0.001, Pearson correlation). Accordingly, a good positive correlation was observed between the values of the two parameters, suggesting that the plasma DNA methylation deconvolution accurately determined the contribution of the placenta to the maternal plasma samples.

Figure 5:
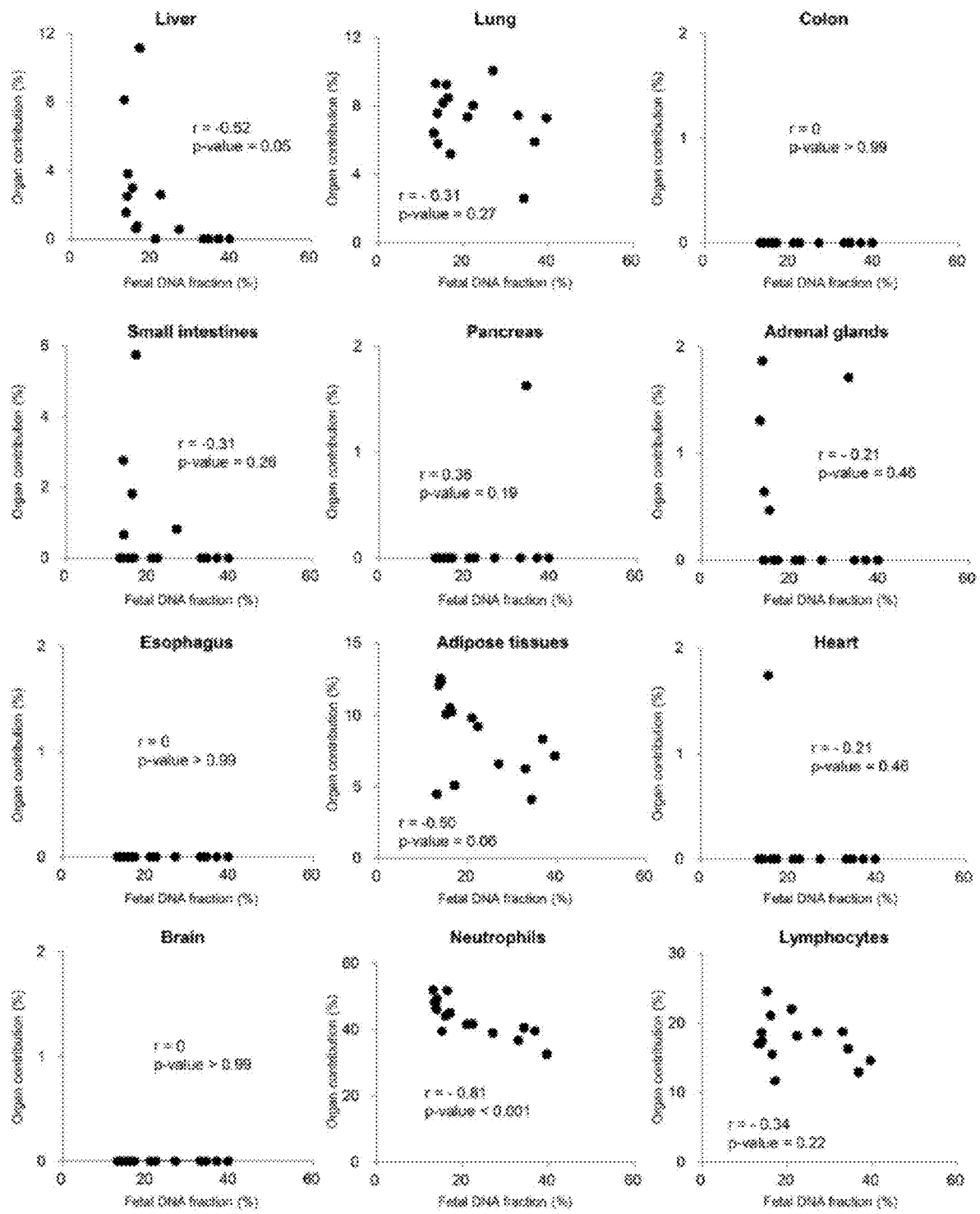
FIG. 5 shows plots of percentage contributions of organs other than the placenta by plasma DNA tissue mapping and fetal DNA fractions based on fetal-specific SNP alleles according to embodiments of the present invention.

FIG. 5 shows plots of percentage contributions of organs other than the placenta by plasma DNA tissue mapping and fetal DNA fractions based on fetal-specific SNP alleles according to embodiments of the present invention. The X-axis represents the fetal DNA fractions estimated by SNP-based analysis and the Y-axis represents the percentage contribution deduced by plasma tissue DNA mapping analysis. Plasma DNA contributions of the neutrophils showed a reverse correlation. This is likely due to the fact that neutrophils were a major contributor to the plasma DNA pool and hence, as the placental contribution increased, the relative contribution from the neutrophils would by necessity reduce. The methylation deconvolution results of the remaining tissues show no correlation with the fetal DNA fraction.

FIG. 6 shows a table 600 of percentage contributions from plasma DNA tissue mapping analysis among the non-pregnant healthy control subjects according to embodiments of the present invention. When the process was applied to plasma of non-pregnant healthy controls, placental contribution was absent in most samples (median: 0%; interquartile range: 0% to 0.3%).

2. Comparison of Selected Markers vs. Random Markers

The accuracy of the percentage contributions was tested with select markers relative to random markers. Different composition calculations were done for different sets of markers. One set was chosen based on criteria mention above, and the other is a random set. The results show that it is important to judicially choose the methylation markers (genomic loci) use, in order to obtain accurate results.

Eleven pregnant women and four healthy non-pregnant subjects were recruited for this analysis. Their plasma DNA was bisulfate converted and sequenced using the Illumina HiSeq2000 sequencer. Each plasma sample was sequenced with one lane of a sequencing flow cell. The sequenced reads were then analyzed using a bioinformatic program, MethyPipe (Jiang P. PLoS One 2014; 9: e100360). This program can align the bisulfate-converted sequence reads to the reference genome and determine the methylation status of each CpG site on each sequenced fragment. Thus, mixture methylation levels can be measured using sequence reads that each aligns to at least one of the genomic sites of the reference genome.

The first set of markers have high specificity for identifying the different tissues in the plasma DNA. For each tissue type, markers that have the biggest difference in methylation density compared with the other tissues were selected. The markers were determined from genomic regions containing at least one CpG dinucleotide. In this example, CpG islands (CGIs) were used as potential markers, having a high frequency of CpG sites in a particular stretch of DNA. CGIs in this particular example are downloaded from the University of California, Santa Cruz (UCSC) database: (genome.ucsc.edu). In total, we obtained 27,048 CpG islands from the human genome. The median size of a CpG island is 565 bp (range: 200 bp to 45 kb). 90% of the islands are less than 1.5 kb.

For each methylation marker, the difference in methylation density between the tissue-of-interest and the other tissues was determined. The difference is then expressed as the number of standard deviations (SDs) across the other tissues. For the tissue-of-interest, all the markers were ranked according to this difference in methylation density. The 20 markers with the biggest difference above (10 markers) and below (10 markers) the mean methylation densities of the other tissues were selected. Other examples of the number of markers include 5, 15, 20, 30, 40, 50, 100 and 200.

In addition, markers with a high variability across all the different tissues were also selected. In this example, markers with >50% difference between the tissues with the highest and lowest methylation densities were selected. Other examples of values for the difference include 20%, 30%, 40%, 60%, 70% and 80%. Furthermore, the variability of methylation densities across different tissues was also calculated based on the mean and SD. In this example, a marker was also selected if the value of SD is more than two times the mean. Other examples of cutoff values can include standard deviations of 1, 1.5, 2.5 and 3. Based on these selection criteria, 344 methylation markers were selected for the first set.

For the second set, 341 markers were randomly selected from the 27,048 CGIs discussed above. All the CGIs were first numbered from 1 to 27,048. Then, a random number (between 1 to 27,048) was generated by a computer for marker selection. This process was then repeated until a total of 341 markers were selected. If a random number generated had been used, another one would be generated. This set of markers is expected to have a much lower specificity in identifying the tissue-specific methylation patterns. Thus, the accuracy of determining the composition of the plasma DNA is expected to be reduced.

FIG. 7 shows a table 700 of the estimated contributions of different organs to the plasma DNA for 11 pregnant women and 4 non-pregnant healthy subjects using the first set of markers (with high organ specificity) according to embodiments of the present invention. The fetal DNA fractions were determined by counting fetal-specific alleles and are shown in the bottom row. In each of the four non-pregnant control subjects, the contribution of the placenta to the plasma was determined to be close to 0%. This indicates the specificity of this approach.

FIG. 8 shows a table 800 of the estimated contributions of different organs to the plasma DNA for 11 pregnant women and 4 non-pregnant healthy subjects using the second set of markers (with low organ specificity) according to embodiments of the present invention. The fetal DNA fractions determined by counting fetal-specific alleles are shown in the bottom row. Using these less specific markers, a relatively non-concordant percentage of contribution from the placenta was observed, and considerable contributions from the placenta were observed in the four non-pregnant control subjects. This indicates that the tissue specificity of the markers is important in this approach.

Figure 9A:
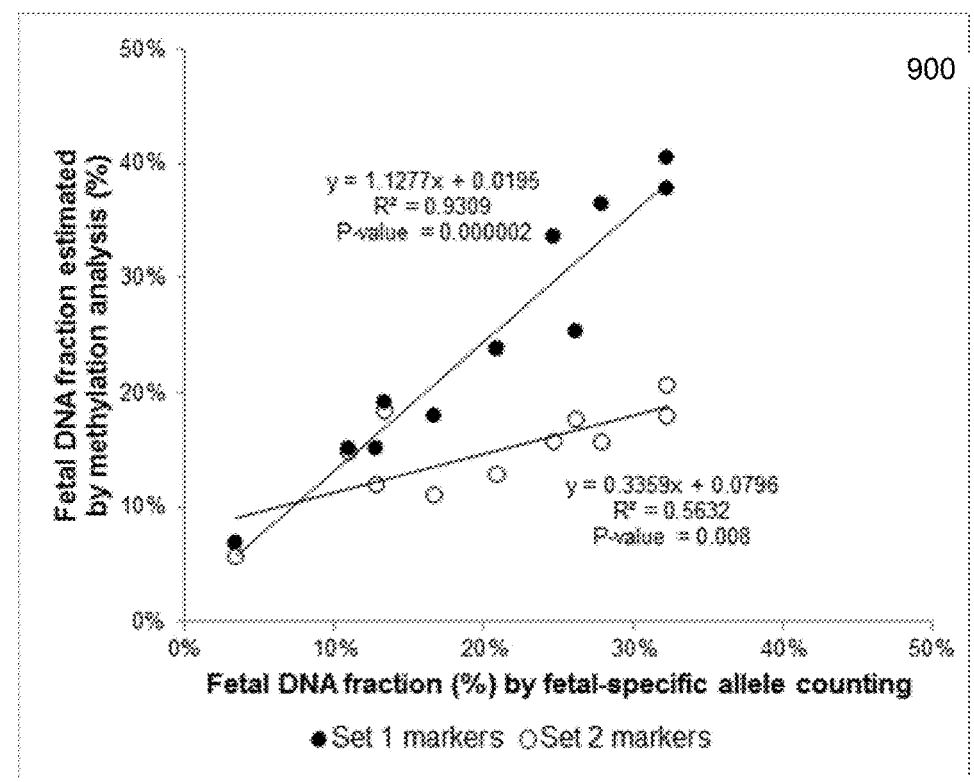
FIG. 9A is a plot showing the correlation between the estimated fetal DNA fraction (contribution from the placenta) and the fetal DNA fraction determined by counting the fetal-specific alleles in the maternal plasma samples.

FIG. 9A is a plot 900 showing the correlation between the estimated fetal DNA fraction (contribution from the placenta) and the fetal DNA fraction determined by counting the fetal-specific alleles in the maternal plasma samples. The results from the two techniques have good correlation using the first set of methylation markers. However, using the second set of methylation markers, the estimation by using the methylation analysis showed significant deviation from the true values determined using fetal-specific alleles counting.

Figure 9B:
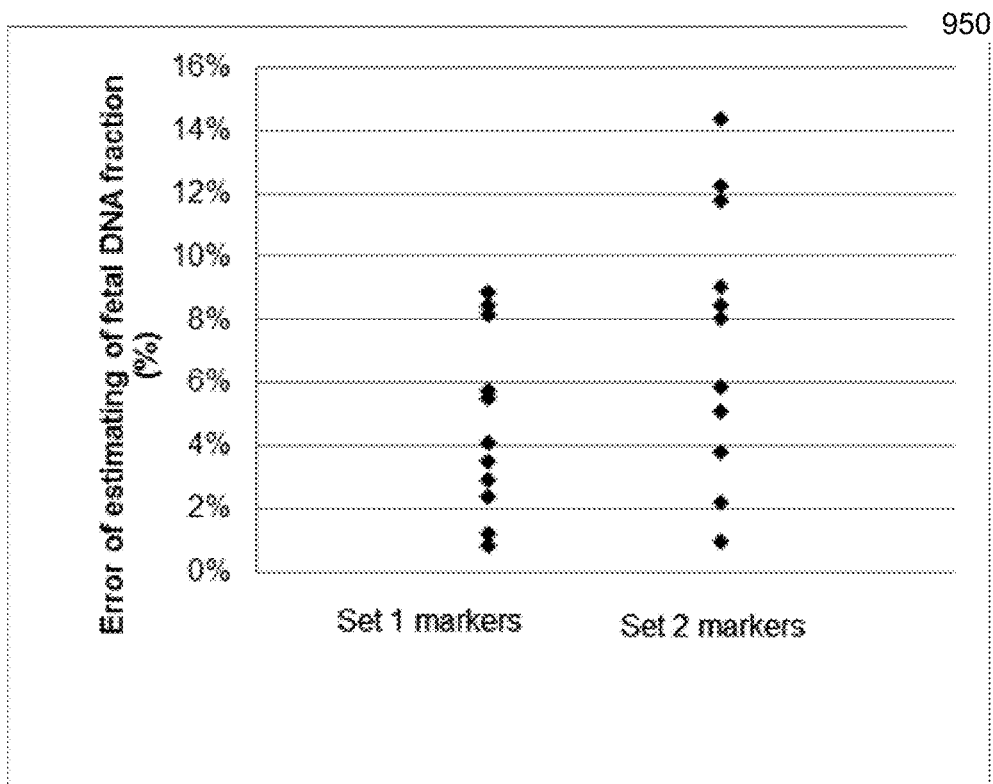
FIG. 9B is a plot showing absolute difference between the estimation from methylation markers and fetal DNA fraction determined by fetal-specific alleles counting.

FIG. 9B is a plot 950 showing absolute difference between the estimation from methylation markers and fetal DNA fraction determined by fetal-specific alleles counting. The median error of the estimation using methylation analysis were 4% and 8% using the first set of markers and the second set of markers, respectively.

C. Cancer Patients

Embodiments can also be used for determining the amount of cancer-derived DNA in the plasma of cancer patients. In this example, venous blood samples were collected from 10 patients suffering from hepatocellular carcinoma (HCC). The percentage contribution of the different organs including the liver, lung, colon, small intestines, pancreas, esophagus, adrenal glands, heart, brain and blood cells were determined using tissue-specific methylation pattern analysis as described above. In addition, the tumor tissues were also analyzed using bisulfite sequencing to identify the tumor-specific methylation patterns. The results of all the different tissues were averaged to determine a representative tumor tissue pattern. Using these tumor-specific methylation markers, the contribution of the tumor to the plasma DNA was also determined.

A total of 828 organ-specific markers were used for this analysis. As controls, four healthy control subjects without cancer were also included in the analysis. For each case, the actual contribution of the tumor tissues to the plasma DNA in the cancer patients was determined by the total methylation level of the plasma. It has been shown that tumor tissues are generally hypomethylated compared with non-tumor tissues (Feinberg et al. Nature. 1983; 301:89-92 and Chan et al. Proc Natl Acad Sci USA. 2013; 110:18761-8). The genome-wide methylation level of non-malignant tissues was approximately 70% whereas that of tumor tissues was around 45%. Thus, the tumoral contribution to the plasma DNA can be estimated using the following formula:

$$f \times 45\% + (1-f) \times 75\% = MD_P$$

where $MD_P$ is the measured genome-wide methylation level for the plasma sample and f is the fractional concentration of tumor-derived DNA in the plasma. This method of estimating tumor-derived DNA fraction has been shown to correlate well with methods based on the detection of chromosomal aberrations (Chan et al. Proc Natl Acad Sci USA. 2013; 110:18761-8).

FIG. 10 shows a table 1000 of contributions of different tissues to the plasma DNA of cancer and healthy patients based on organ-specific methylation pattern analysis according to embodiments of the present invention. In each of the four healthy control subjects without a cancer, the contribution from tumor tissues was determined as 0%. This indicates that the methylation pattern analysis is specific.

Figure 11A:
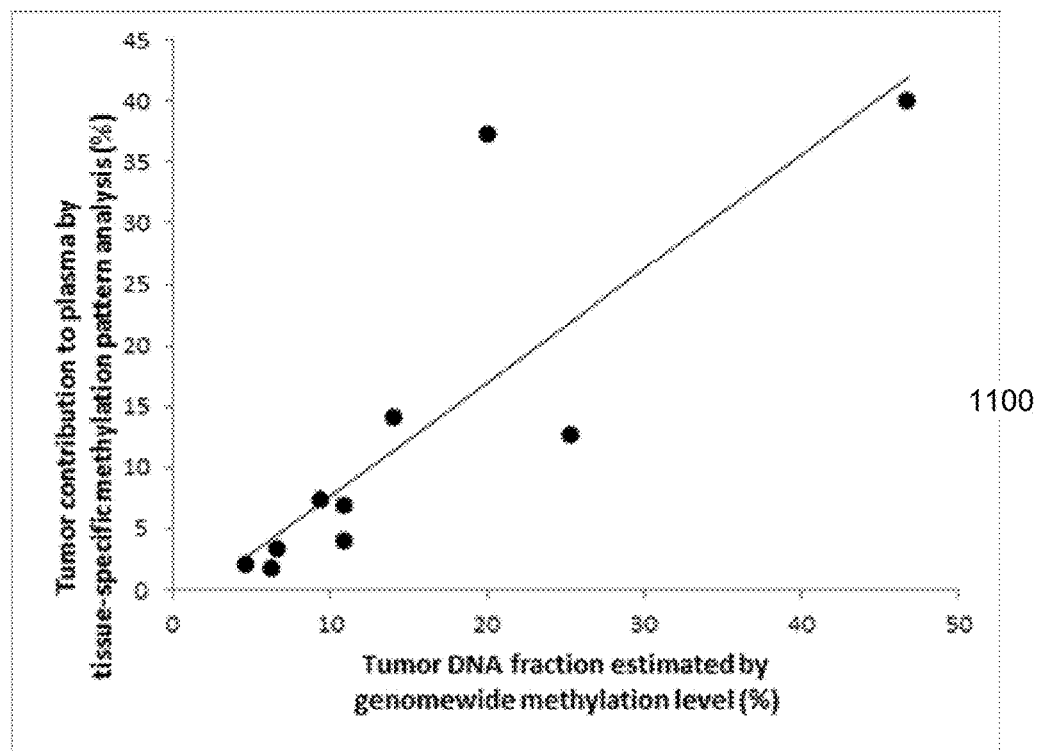
FIG. 11A is a plot 1100 showing the values of tumor DNA fraction determined by organ-specific methylation pattern analysis and determined by the genome-wide methylation level according to embodiments of the present invention.

FIG. 11A is a plot 1100 showing the values of tumor DNA fraction determined by organ-specific methylation pattern analysis and determined by the genome-wide methylation level according to embodiments of the present invention. Plot 1100 shows that the tumor DNA fractions determined by organ-specific methylation pattern analysis and tumor DNA fractions determined by the genome-wide methylation level analysis correlate well in the 10 HCC patients.

We also measured the fractional concentrations of HCC tumor DNA in the plasma by studying the genomic regions with loss of heterozygosity, which is a technique that we have previously named genome-wide aggregated allelic loss (GAAL) (Chan K C A, et al. (2013) *Clin Chem* 59(1):211-224).

Figure 11B:
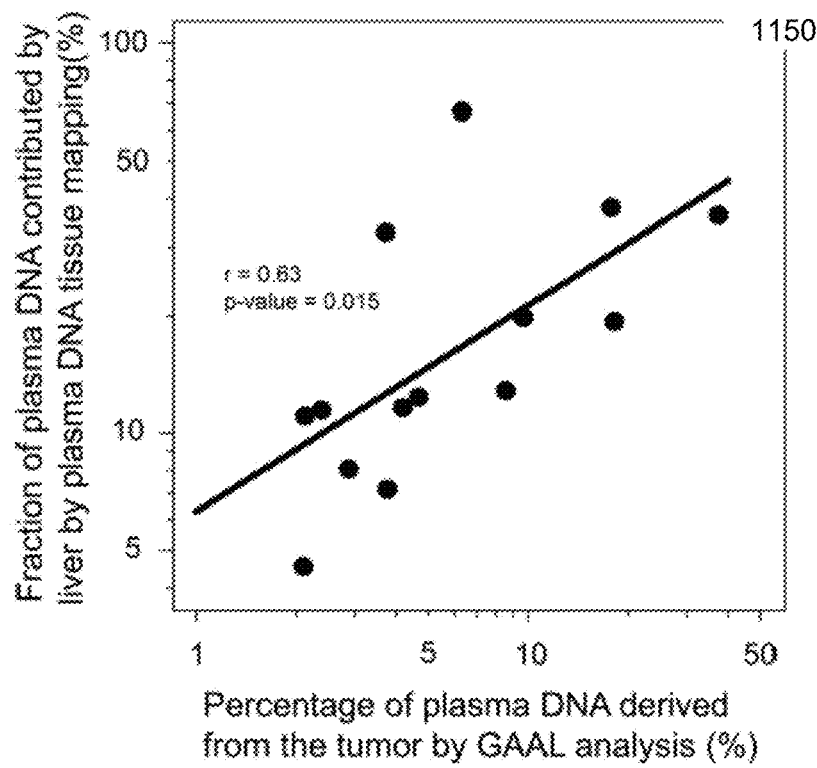
FIG. 11B is a plot showing a correlation between the fractions of plasma DNA contributed by the liver based on plasma DNA tissue mapping analysis and tumor-derived plasma DNA fractions determined by GAAL analysis.

FIG. 11B is a plot 1150 showing a correlation between the fractions of plasma DNA contributed by the liver based on plasma DNA tissue mapping analysis and tumor-derived plasma DNA fractions determined by GAAL analysis. Plot 1150 shows that there is a good correlation between the contributions of liver-derived DNA into plasma deduced by methylation deconvolution and the tumor DNA concentration measured by GAAL (r=0.63, p=0.015, Pearson correlation).

In another embodiment, genome-wide aggregated allelic loss (GAAL) analysis may be performed in the following manner. The tumor samples of the HCC cases may be analyzed using the Affymetrix Genome-Wide Human SNP Array 6.0 system. Regions exhibiting loss of heterozygosity (LOH) may be identified as previously described (Chan et al. Clin Chem. 2013; 59: 211-24). The fractional concentrations of tumor-derived DNA in plasma can be determined by analyzing, in a genome-wide manner, the allelic counts for SNPs exhibiting LOH in the plasma sequencing data using the following equation:

$$C = \frac{N_{non-del} - N_{del}}{N_{non-del}},$$

where $N_{non-del}$ represents the number of sequenced reads carrying the non-deleted alleles in the tumor tissues, and $N_{del}$ represents the number of sequenced reads carrying the deleted alleles in the tumor tissues.

Figure 12A:
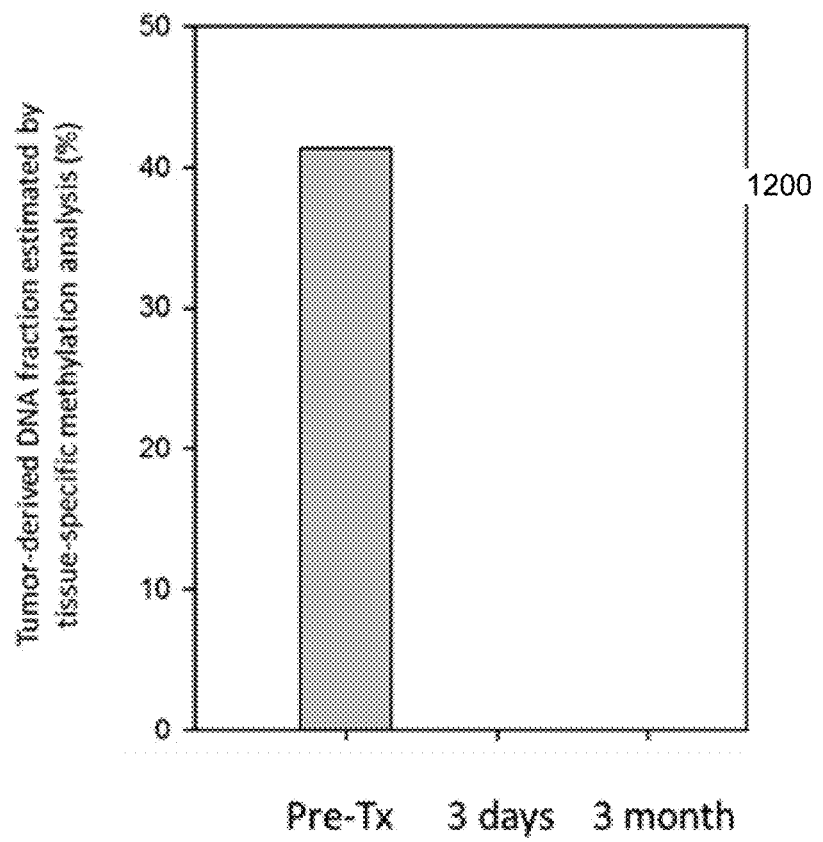
FIG. 12A is a graph showing the estimated tumor-derived DNA in the plasma of patient HCC 10 at various times.

FIG. 12A is a graph 1200 showing the estimated tumor-derived DNA in the plasma of patient HCC 10 at various times. The samples were taken before surgery (Pre-Tx) and at 3 days and 3 months after the surgical resection of the patient. This patient was in clinical remission at 2 years after tumor resection. At 3 days and 3 months after the surgical resection of the tumor, the tumor-specific methylation pattern was not detectable in the plasma. This finding was compatible with the finding of the absence of any detectable cancer at 2 years after the operation.

Figure 12B:
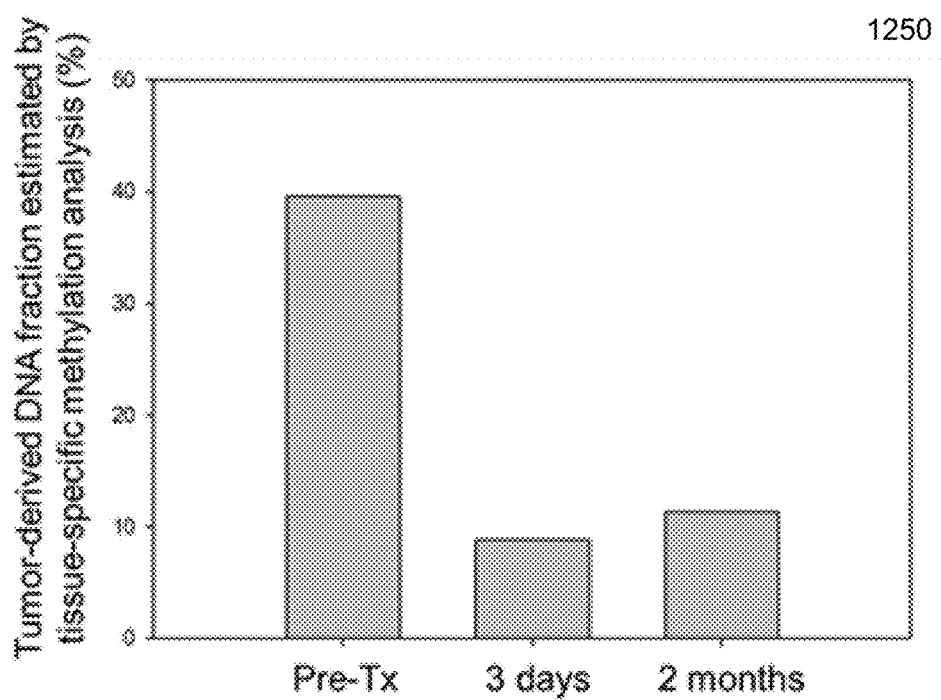
FIG. 12B is a graph showing the estimated tumor-derived DNA in the plasma of patient HCC 9.

FIG. 12B is a graph 1250 showing the estimated tumor-derived DNA in the plasma of patient HCC 9. The samples were taken before treatment (Pre-Tx) and at 3 days and 2 months after the surgical resection of the patient. This patient was later diagnosed as having multifocal tumor deposits (previously unknown at the time of surgery) in the remaining non-resected liver at 3 months and was noted to have multiple lung metastases at 4 months after the operation. The patient died of metastatic disease at 8 months after the operation. Using tissue-specific methylation pattern analysis, it was estimated that the tumor tissue contribute 8% and 12% of the total plasma DNA at 3 days and 2 months after the operation.

D. Organ Transplantation and Deconvolution

The quantification of the contribution of an organ to the plasma DNA can be usefully applied for the monitoring of patients receiving organ transplantation. It has been shown that the level of DNA released by a transplanted organ would increase in situations associated with the damage of the transplanted organ, for example, in tissue rejection (De Vlaminck et al. Sci Transl Med. 2014; 6:241ra77). However, existing methods only based the detection of polymorphic markers that are different between the donor and the recipient, e.g. SNP alleles that are present in the donor but are absent in the recipient (De Vlaminck et al. Circulating cell-free DNA enables noninvasive diagnosis of heart transplant rejection. Sci Transl Med. 2014; 6:241ra77) or chromosome Y sequences for sex-mismatch transplant cases (Garcia Moreira et al. Cell-free DNA as a noninvasive acute rejection marker in renal transplantation. Clin Chem. 2009; 55:1958-66). For the analysis of polymorphic markers, tissues of both the organ donor and the recipient are required for genotyping. The genotyping of the donor and recipient tissues would add additional costs to the analysis and the tissue of the organ donor may not be available in practice. And, the sequences on chromosomes X and Y are only useful in situations where the donor and the recipient have different sexes. Accordingly, the methylation deconvolution techniques can be less time and cost intensive than some previous techniques, and more applicable other previous techniques.

1. Correlation of Fractions

This section shows the accuracy of determining the proportion of the plasma DNA contributed from the donor organ, as determined by plasma DNA methylation deconvolution analysis. In this method, genotyping of the tissues from the donor and recipient is not required.

Subjects who had received transplantation provided a valuable opportunity for validating the plasma DNA tissue mapping approach. By using SNP alleles that were present in an organ donor and which were absent in a transplant recipient, one could measure the fractional concentration of the transplant organ in plasma as previously described (Zheng Y W, et al. 2012). This result could then be compared with that deduced using methylation deconvolution.

FIG. 13 is a table 1300 showing plasma DNA tissue mapping analysis among organ transplantation patients according to embodiments of the present invention. We performed plasma DNA tissue mapping for 4 liver transplant recipients and 3 bone marrow transplant recipients. For each case, tissues from the donor and the recipient were obtained and genotyped using massively parallel sequencing. Donor-specific SNP alleles were identified and were used for the calculation of the fraction of plasma DNA contributed from the donor organ. The donor DNA fractions estimated using the donor-specific SNP alleles were compared with the liver contributions among the liver transplant recipients, whilst those amongst the bone marrow transplant recipients were compared with the white blood cell contributions (i.e. neutrophils plus lymphocytes). Then, plasma methylation deconvolution was carried out to determine the contribution of the liver and blood cells in the liver transplant and bone marrow transplant cases, respectively.

Figure 14:
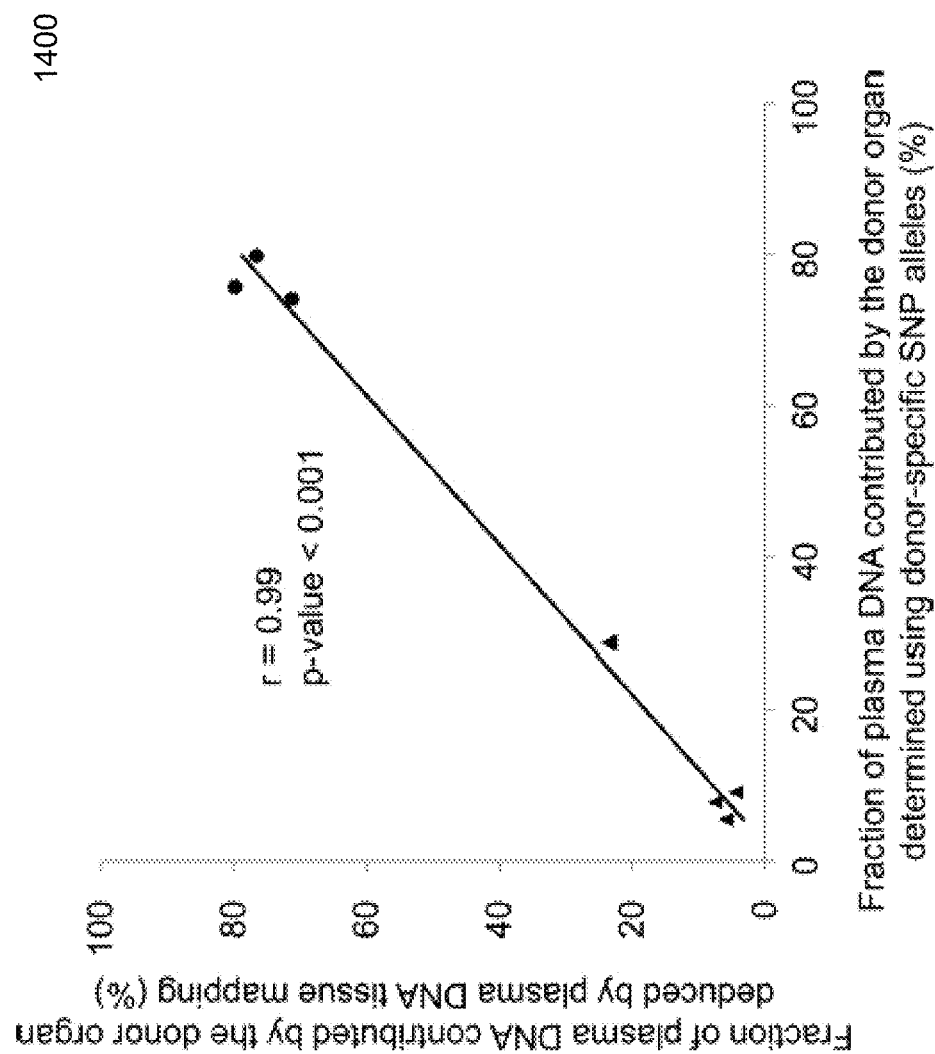
FIG. 14 is a plot showing a correlation between the fractions of plasma DNA contributed by the transplanted graft deduced by plasma DNA tissue mapping and the donor DNA fractions determined using donor-specific SNP alleles.

FIG. 14 is a plot 1400 showing a correlation between the fractions of plasma DNA contributed by the transplanted graft deduced by plasma DNA tissue mapping and the donor DNA fractions determined using donor-specific SNP alleles. The triangles represent the results of liver transplant recipients and the dots represent the results of bone marrow transplant recipients. Plot 1400 shows a strong correlation between the methylation deconvolution and SNP-based results (r=0.99, p<0.001, Pearson correlation).

2. Comparison of Different Marker Types

The relative contributions of the type I and type II markers in the methylation deconvolution analysis were compared. To fairly compare their contributions, 1013 type II markers were first randomly selected so that the number of type I and type II markers used for the subsequent analysis were the same. The 1013 type I markers and 1013 type II markers formed a pool.

Methylation deconvolution using different numbers of randomly selected methylation markers was performed to determine the contributions of the transplanted organ (i.e. liver for liver transplant recipients and blood cells for bone marrow transplant recipients). After the markers had been randomly selected, deconvolution analyses based on the actual sequencing data were performed. In each analysis, the same number of type I and type II markers was used. However, the total number of markers was varied in different sets of deconvolution analysis so as to determine the effect of the number of markers on the accuracy of methylation deconvolution analysis. For each analysis, the difference between the percentage contribution of the transplanted organ to plasma DNA by methylation deconvolution and the value derived from the donor-specific SNP alleles were plotted.

Figure 15A:
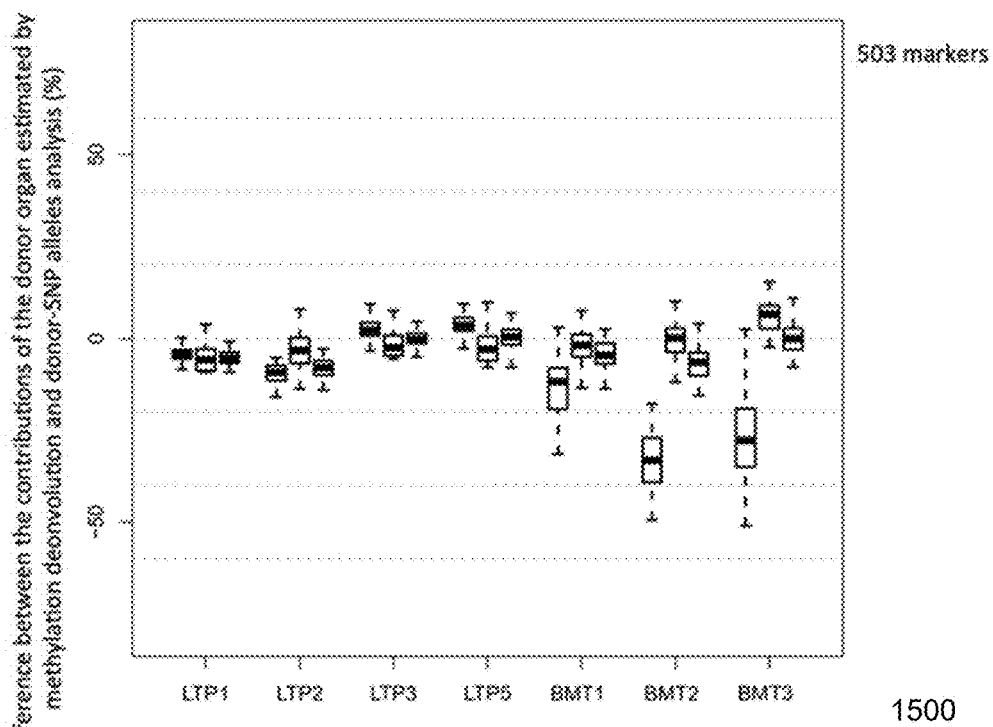
FIG. 15A is a graph shows an analysis comparing the accuracies of using 503 type I, 503 type II and both types (503 each) of markers for methylation deconvolution.

FIG. 15A is a graph 1500 showing an analysis comparing the accuracies of using 503 type I, 503 type II and both types (503 each) of markers for methylation deconvolution. The difference between the percentage contribution of the transplanted organ to plasma DNA by methylation deconvolution and the value derived from the donor-specific SNP alleles are shown for the patients who had received liver transplantation (LTP1 to LTP5) and for the patients who had received bone marrow transplantation (BMT1 to BMT3). For each patient, the methylation deconvolution results using type I markers only, type II markers only, and both types of markers are shown by the boxes on the left, in the middle and on the right, respectively. The analysis using type I markers alone had larger bias compared with using type II markers only, or both types of markers. On the other hand, no significant difference was observed between the results using type II markers only, and using both types of markers.

Figure 15B:
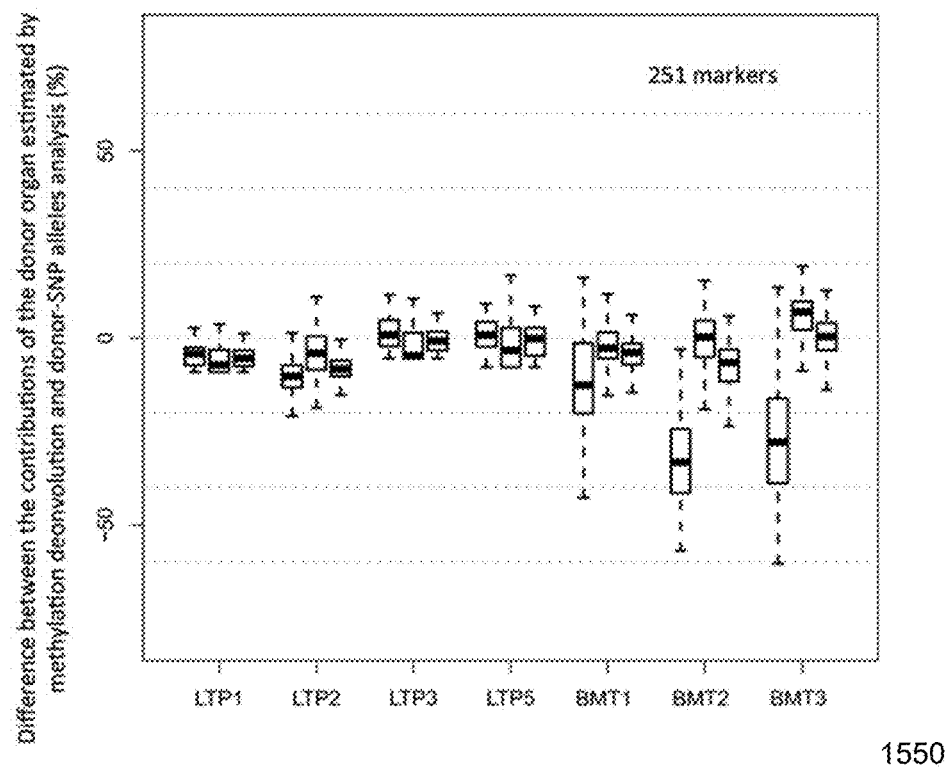
FIG. 15B is a graph showing an analysis comparing the accuracies of using 251 type I, 251 type II and both types (251 each) of markers for methylation deconvolution.

FIG. 15B is a graph 1550 showing an analysis comparing the accuracies of using 251 type I, 251 type II and both types (251 each) of markers for methylation deconvolution. The difference between the percentage contribution of the transplanted organ to plasma DNA by methylation deconvolution and the value derived from the donor-specific SNP alleles are shown for the patients who had received liver transplantation (LTP1 to LTP5) and those who had received bone marrow transplantation (BMT1 to BMT3). For each patient, the methylation deconvolution results using type I markers only, type II markers only and both types of markers are shown by the boxes on the left, in the middle and on the right, respectively. The analysis using type I markers alone had larger bias compared with using type II markers only, or both types of markers. On the other hand, no significant difference was observed between the results using type II markers only, and using both types of markers.

Figure 16A:
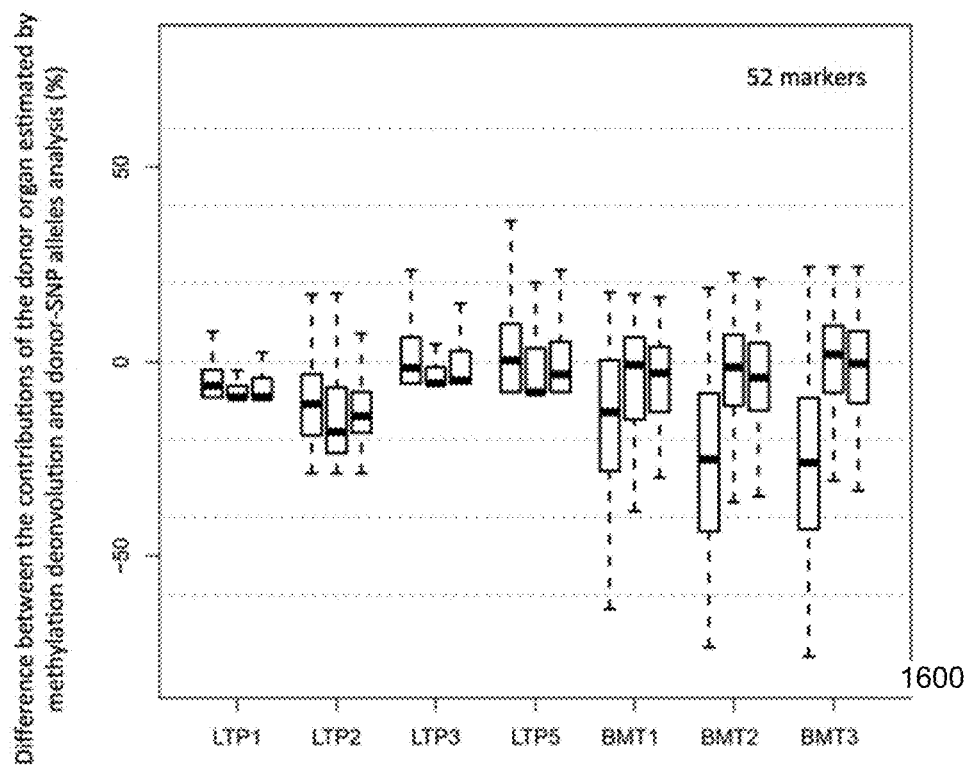
FIG. 16A is a graph showing an analysis comparing the accuracies of using 52 type I, 52 type II and both types (52 each) of markers for methylation deconvolution.

FIG. 16A is a graph 1600 showing an analysis comparing the accuracies of using 52 type I, 52 type II and both types (52 each) of markers for methylation deconvolution. The difference between the percentage contribution of the transplanted organ to plasma DNA by methylation deconvolution and the value derived from the donor-specific SNP alleles are shown for the patients who had received liver transplantation (LTP1 to LTP5) and those who had received bone marrow transplantation (BMT1 to BMT3). For each patient, the methylation deconvolution results using type I markers only, type II markers only and both types of markers are shown by the boxes on the left, in the middle and on the right, respectively. The analysis using type I markers only had larger bias compared with using type II markers only, or both types of markers. On the other hand, no significant difference was observed between the results using type II markers only, and using both types of markers.

Figure 16B:
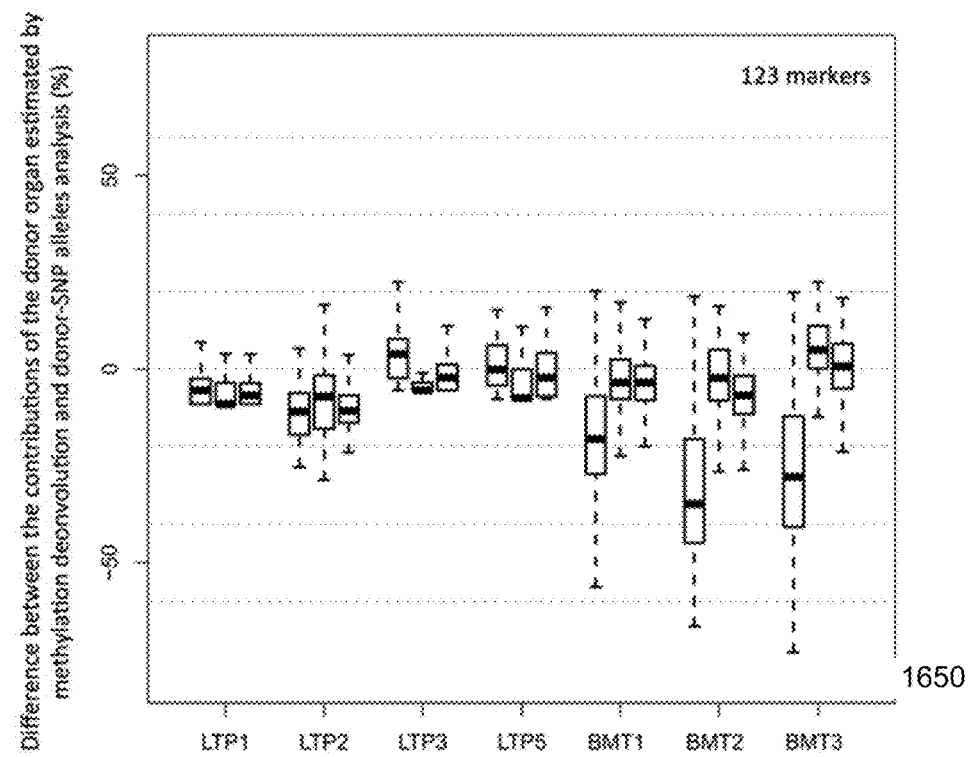
FIG. 16B is a graph showing an analysis comparing the accuracies of using 123 type I, 123 type II and both types (123 each) of markers for methylation deconvolution.

FIG. 16B is a graph 1650 showing an analysis comparing the accuracies of using 123 type I, 123 type II and both types (123 each) of markers for methylation deconvolution. The difference between the percentage contribution of the transplanted organ to plasma DNA by methylation deconvolution and the value derived from the donor-specific SNP alleles are shown for the patients who had received liver transplantation (LTP1 to LTP5) and those who had received bone marrow transplantation (BMT1 to BMT3). For each patient, the methylation deconvolution results using type I markers only, type II markers only and both types of markers are shown by the boxes on the left, in the middle and on the right, respectively. The analysis using type I markers alone had larger bias compared with using type II markers only, or both types of markers. On the other hand, no significant difference was observed between the results using type II markers only, and using both types of markers.

Figure 17A:
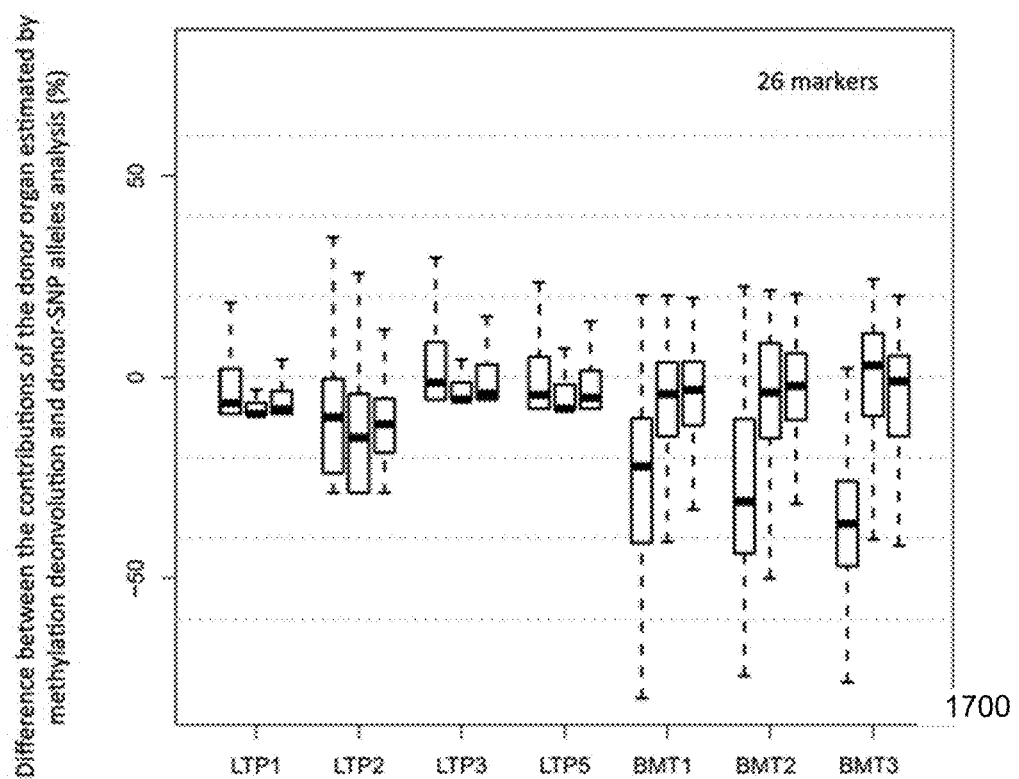
FIG. 17A is a graph showing an analysis comparing the accuracies of using 26 type I, 26 type II and both types (26 each) of markers for methylation deconvolution.

FIG. 17A is a graph 1700 showing an analysis comparing the accuracies of using 26 type I, 26 type II and both types (26 each) of markers for methylation deconvolution. The difference between the percentage contribution of the transplanted organ to plasma DNA by methylation deconvolution and the value derived from the donor-specific SNP alleles are shown for the patients who had received liver transplantation (LTP1 to LTP5) and those who had received bone marrow transplantation (BMT1 to BMT3). For each patient, the methylation deconvolution results using type I markers only, type II markers only and both types of markers are shown by the boxes on the left, in the middle and on the right, respectively. The analysis using type I markers only had larger bias compared with using type II markers only, or both types of markers. On the other hand, no significant difference was observed between the results using type II markers only, and using both types of markers.

Figure 17B:
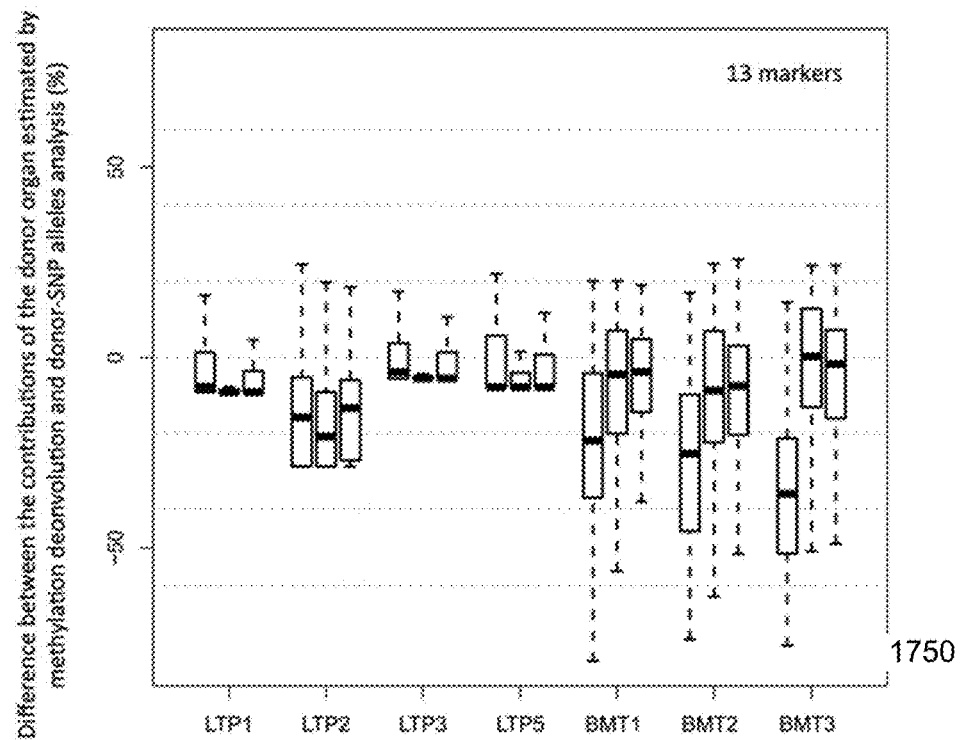
FIG. 17B is a graph showing an analysis comparing the accuracies of using 13 type I, 13 type II and both types (13 each) of markers for methylation deconvolution.

FIG. 17B is a graph 1750 showing an analysis comparing the accuracies of using 13 type I, 13 type II and both types (13 each) of markers for methylation deconvolution. The difference between the percentage contribution of the transplanted organ to plasma DNA by methylation deconvolution and the value derived from the donor-specific SNP alleles are shown for the patients who had received liver transplantation (LTP1 to LTP5) and those who had received bone marrow transplantation (BMT1 to BMT3). For each patient, the methylation deconvolution results using type I markers only, type II markers only and both types of markers are shown by the boxes on the left, in the middle and on the right, respectively. The analysis using type I markers only had obviously larger bias compared with using type II markers only, or both types of markers. On the other hand, no significant difference was observed between the results using type II markers only, and using both types of markers.

Overall, type II markers provided better results that type I markers, which is surprising, especially given the focus on type I markers in previous studies. Our results also show that more markers provide greater accuracy.

E. Effect of Different Criteria

As described above, various criteria can be used to identify markers of different types. For example, a type I marker can be identified by a methylation level in a particular tissue that is different from the mean methylation level for all tissues, e.g., at least by a specific threshold, such as 3 SD. And, for type II markers, criteria of a certain variation and maximum difference are used. Sections below show accuracy of different criteria for identifying markers.

1. Performance of Markers with Less Stringent Criteria

We compared the performance of methylation deconvolution analysis using markers with different variability across different tissues. The placental contributions to plasma DNA were determined for 15 pregnant women based on two sets of markers with different selection criteria. Both sets of markers include all the type I markers as described in previous sections. However, the selection criteria of type II markers are different for the two sets of markers.

Set I markers include all the 5820 type II markers fulfilling the criteria of having methylation density CV>0.25 and the difference between the maximum and minimum methylation densities for the groups of tissues exceeding 0.2. For Set II markers, the CV requirement was >0.15 and the difference between the maximum and minimum methylation densities for the groups of tissues exceeded 0.1. There were 8,511 type II markers in this set of markers.

Figure 18A:
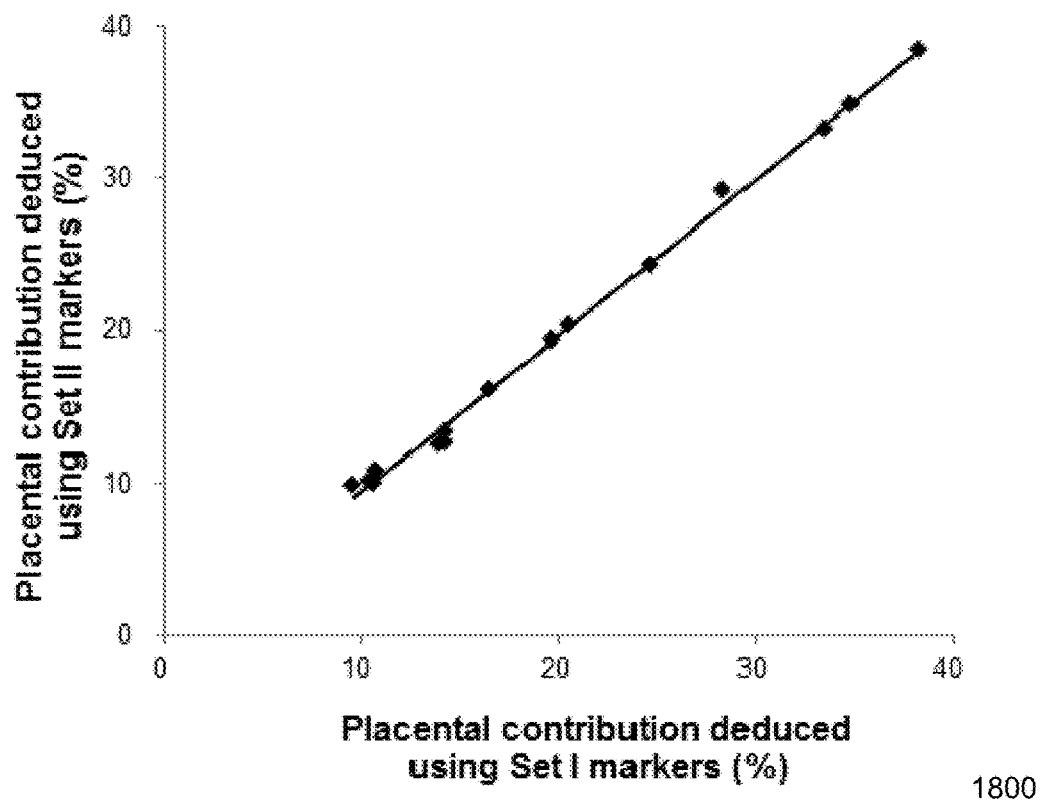
FIG. 18A is a graph showing placental contribution to plasma DNA deduced using markers with different selection criteria according to embodiments of the present invention.

FIG. 18A is a graph 1800 showing placental contribution to plasma DNA deduced using markers with different selection criteria according to embodiments of the present invention. The vertical axis corresponds to placental contribution deduced using the set II markers. The horizontal axis corresponds to placental contribution deduced using the set I markers. There was a good correlation between the placental contribution results based on the two sets of markers with different selection criteria (r=0.99, Pearson correlation). Accordingly, good accuracy can be obtained using the requirements of CV>0.15 and of the difference between the maximum and minimum methylation densities for the groups of tissues exceeding 0.1.

2. Effect of Methylation Level Variation within Same Type of Tissue

To investigate if the variation in methylation level of markers between the same type of tissues (e.g. from different individuals) would affect the performance of deconvolution analysis, we analyzed placental tissues from two pregnant cases. Two categories of methylation markers were identified. Specifically, the two categories were identified based on their similarity in methylation levels in two placental tissues. Markers of category i have a methylation density of 10% or lower. Markers of category ii have high variability between the two placental tissues (difference in methylation density of more than 10%).

Figure 18B:
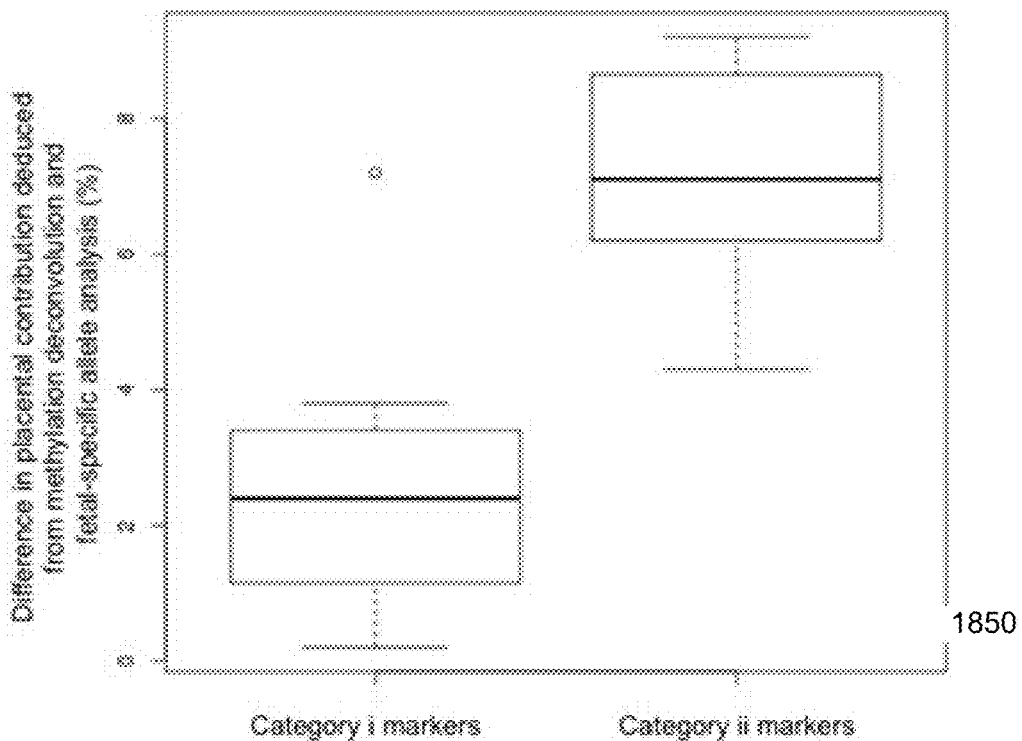
FIG. 18B is a graph showing the accuracy of plasma DNA deconvolution using markers with low variability (category i) and high variability (category ii) in the same type of tissue.

FIG. 18B is a graph 1850 showing the accuracy of plasma DNA deconvolution using markers with low variability (category i) and high variability (category ii) in the same type of tissue. Plasma DNA deconvolution was performed to determine the placental contribution to the plasma DNA for 15 pregnant women. For each marker, the mean of the methylation densities of the two placental tissues were used to represent the methylation level of the placenta in the analysis. For each of the deconvolution analysis using the category i and category ii markers, a total of 1024 markers were used.

The amount of placentally-derived DNA in plasma was further determined based on the proportion of the fetal-specific SNP alleles. The percentage contribution deduced by the methylation deconvolution analysis based on category i and category ii markers were then compared with the results based on fetal-specific SNP alleles. The median deviation of the derived placental contribution from the value estimated based on fetal-specific alleles was 2.7% and 7.1% using category i and category ii markers, respectively. Thus, the use of category i markers which had lower inter-individual variation in the tissue methylation level gave better accuracy in the methylation deconvolution analysis.

Significantly higher difference between the results from methylation deconvolution and fetal-specific allele analysis was observed when markers with high variability within the same type of tissue (category ii) were used (P<0.0001, Wilcoxon sign-rank test). In other words, the use of markers with low variability within the same type of tissue would increase the accuracy of methylation deconvolution analysis. Accordingly, markers can be selected based on the variability within the same type of tissues, for example, but not limited to the value of CV and the difference between the maximum and minimum methylation density for the same type of tissues.

IV. Identifying Disease in Tissue from Increased Contribution

In one application for using the determined fractional contributions, embodiments can detect abnormal fractional contributions from a particular tissue type relative to reference levels. In one embodiment, the reference levels can correspond to the values established in organisms that are healthy for the tissue type. In another embodiment, the reference level can correspond to a fractional contribution determined using cell-free DNA molecules of a different size range.

A. Increased Percentage Relative to Healthy Percentages

Embodiments can detect that the determined fractional contribution from a particular tissue type is higher than is normally expected for a healthy organism. The increased fractional contribution for the particular tissue type would result from that tissue being diseased, and therefore releasing more cell-free DNA molecules. For example, a diseased organ would release more cell-free DNA molecules as a result of apoptosis or other cellular mechanisms.

1. Determining Tissue Origin for Cancers of Unknown Primary

In previous studies, it has been demonstrated that tumor-associated DNA changes can be detected in the cell-free plasma of cancer patients. For example, cancer-associated chromosomal copy number changes and cancer-associated global hypomethylation can be detected in the plasma DNA of cancer patients. Therefore, the analysis of plasma DNA would be potentially useful for the screening of cancers in apparently healthy individuals (Chan et al. Proc Natl Acad Sci USA. 2013; 110:18761-8 and Chan et al. Clin Chem. 2013; 59:211-24). After the detection of cancer-associated features in the plasma, it is also important to determine where the primary tumor is.

Here, we propose that the tumor cells would exhibit some of the DNA methylation features of the primary tissue that they have originated from. We reasoned that the tumor-derived DNA would have a methylation profile more similar to the original tissue of origin than to other tissues. Therefore, in the presence of tumor-derived DNA in plasma, there would be an apparent increase in contribution of the tissue that the tumor had originated from to the plasma DNA. Thus, the analysis of tissue-specific DNA methylation patterns in the plasma DNA of patients with cancers would be useful for indicating the site of the primary tumor.

In this example, we analyzed the plasma DNA of the 10 HCC patients discussed above, two patients with lung cancers and one patient with colorectal cancer. The methylation patterns of different organs were used for analysis. However, the methylation patterns of the tumor tissues were not included in the analysis because in a cancer screening scenario, the tumor tissue is usually not available for methylation analysis.

FIG. 19 is a table 1900 showing contributions of different tissues to the plasma DNA of patients with various cancers and healthy subjects based on organ-specific methylation pattern analysis according to embodiments of the present invention. The liver contribution is increased in 9 of the 10 HCC patient's plasma compared with the mean of the healthy subjects. The contributions from lung and colon are increased in the patients with lung cancers and colorectal cancers, respectively. Accordingly, the diseased tissue does correspond to the abnormal fraction contribution.

FIG. 20 shows a table 2000 shows the contributions of the different organs for each cancer patient compared with the mean of the four control subjects according to embodiments of the present invention. The contributions are shown as differences in the fractional contribution from the mean of the four control subjects.

Positive and negative values indicate increase and decrease, respectively, in the contribution from the particular organ. In each patient, the number in bold represent the greatest increment compared with the control subjects. For 8 of the 10 HCC patients, the contribution from liver had the greatest increase compared with the four control subjects. For both of the lung cancer patients, the contribution from the lung showed the greatest increase. For the colorectal cancer patient, the greatest increase was from the colon. These results show that tissue-specific methylation pattern analysis in plasma can be useful for determining the origin of cancers in which primary cancer is concealed.

Figure 21A:
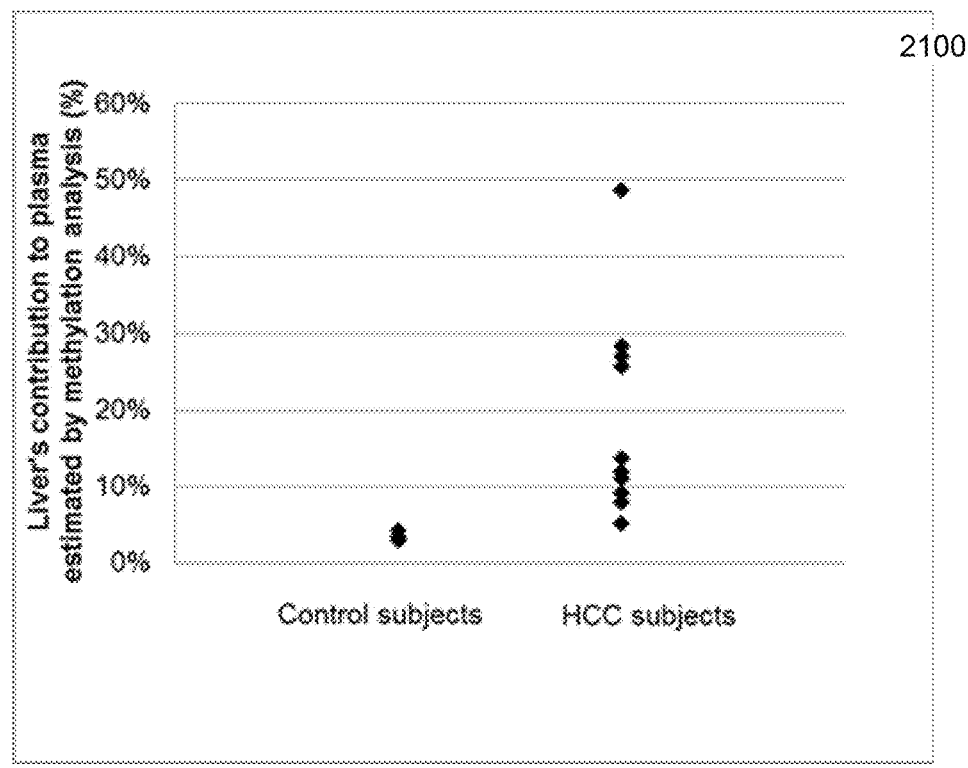
FIG. 21A is a plot showing contributions of the liver to plasma DNA estimated from methylation markers for HCC and healthy control subjects according to embodiments of the present invention.

FIG. 21A is a plot 2100 showing contributions of the liver to plasma DNA estimated from methylation markers for HCC and healthy control subjects according to embodiments of the present invention. The liver's contribution to plasma is significantly elevated in HCC subjects compared with healthy control subjects. Accordingly, the fractional contribution can be used as a measurement of a sample, where the measurement can be compared to a threshold (e.g., about 8%) to identify an elevated risk of disease. The comparison to the threshold can provide a classification of whether the tissue type is diseased, where the classification can be varying levels of probability for the tissue being diseased.

Further examples are provided for the analysis of plasma DNA using methylation deconvolution being applied for cancer detection. To demonstrate this phenomenon, the plasma DNA from 29 patients with hepatocellular carcinoma (HCC), four patients with lung cancer and one patient with colorectal cancer were analyzed. Thirty-two healthy subjects were recruited as controls, as shown in table 600 of FIG. 6. Among them, the plasma DNA genome-wide bisulfite sequencing results have been reported in a previous study (Chan et al. Proc Natl Acad Sci USA. 2013; 110:18761-8) for 26 HCC patients, 4 lung cancer patients and 32 controls. In these examples, the methylation profiles of the plasma DNA were determined using bisulfite sequencing. Other methylation detection methods, for example, but not limited to those mentioned in the last section can also be used.

Figure 21B:
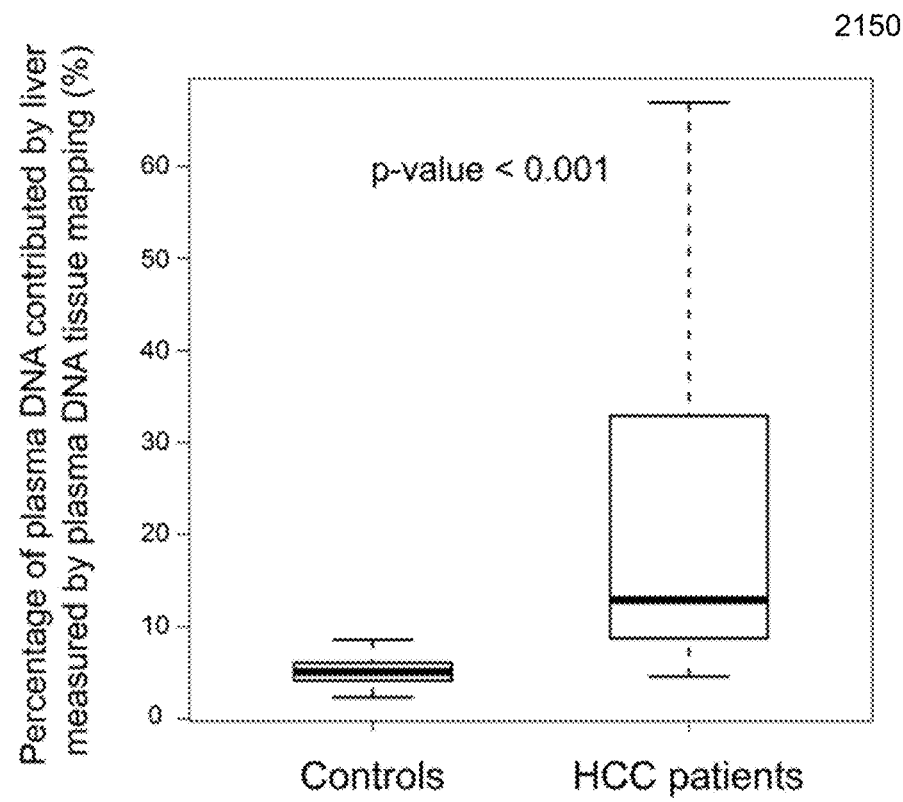
FIG. 21B is a plot showing percentage of plasma DNA contributed by the liver among healthy controls and patients with HCC as deduced by embodiments of the present invention.

FIG. 21B is a plot 2150 showing percentage of plasma DNA contributed by the liver among healthy controls and patients with HCC as deduced by embodiments of the present invention. The percentage of plasma DNA contributed by the liver was significantly higher (P<0.001, Mann-Whitney rank-sum test) in the HCC patients compared with the control subjects. Plot 2150 provides further evidence of the ability to compare a fractional contribution for a tissue to a reference value to identify a diseased state of the tissue.

Figure 22A:
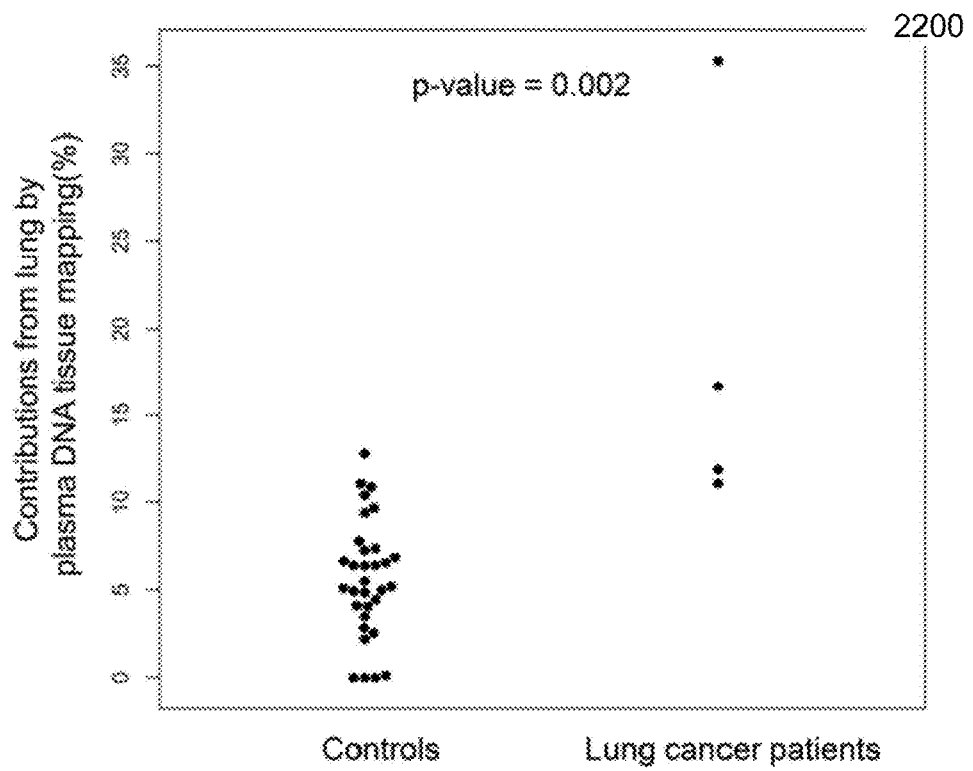
FIGS. 22A and 22B show percentage contributions of (A) the lungs and (B) the colon deduced from embodiments of the present invention with comparisons between non-pregnant healthy controls and patients with lung cancer or colorectal cancer.
Figure 22B:
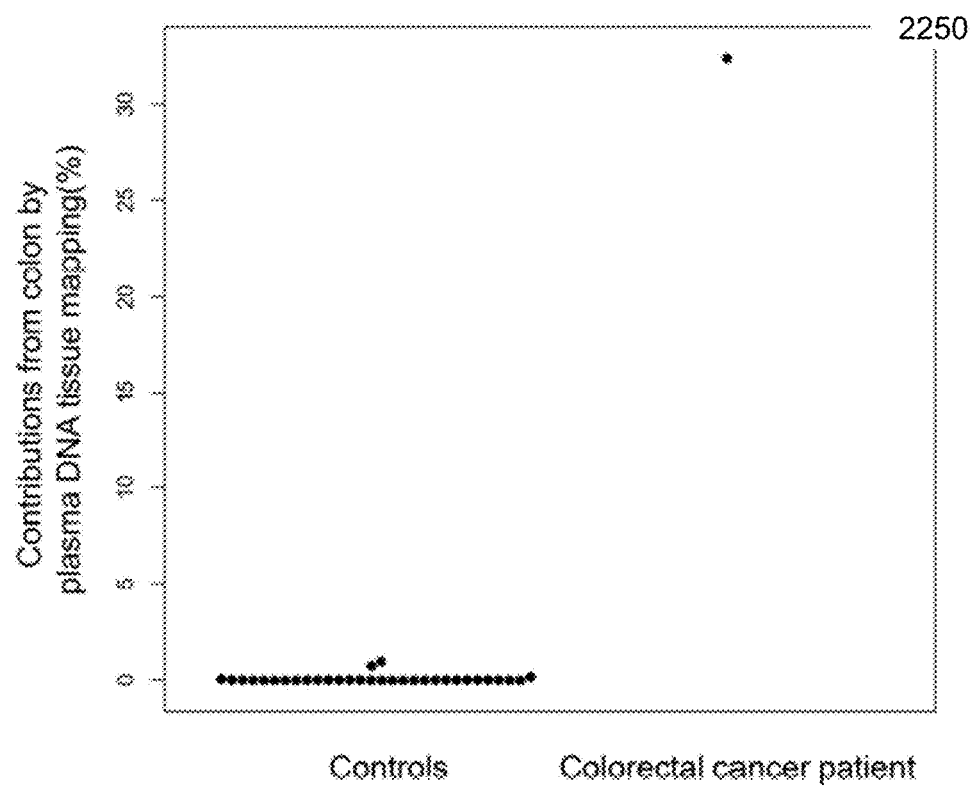

FIGS. 22A and 22B show percentage contributions of (A) the lungs and (B) the colon deduced from embodiments of the present invention with comparisons between non-pregnant healthy controls and patients with lung cancer or colorectal cancer. FIG. 22A is a plot 2200 showing the percentage of plasma DNA contributed by the lung was significantly higher (P=0.002, Mann-Whitney rank-sum test) in the lung cancer patients compared with the control subjects. FIG. 22B is a plot 2250 showing the percentage of plasma DNA contributed by the colon of the lung cancer patients was higher than all the control subjects. These data show that the analysis of plasma DNA using methylation deconvolution analysis is useful for identifying the tissue of origin of a cancer (e.g., after the patient has been identified as likely having cancer) and for screening a patient to identify disease states of tissue in the first place.

FIG. 23 is a table 2300 showing plasma DNA tissue mapping analysis among the cancer patients according to embodiments of the present invention. The methylation deconvolution indicated that the median percentage contributions by the liver to the plasma for HCC and control subjects were 12.9% (interquartile range: 8.7%-32.9%) and 5.5% (interquartile range: 4.6%-7.1%), respectively.

2. Method for Detecting Disease State Based on Increased Contribution

Figure 24:
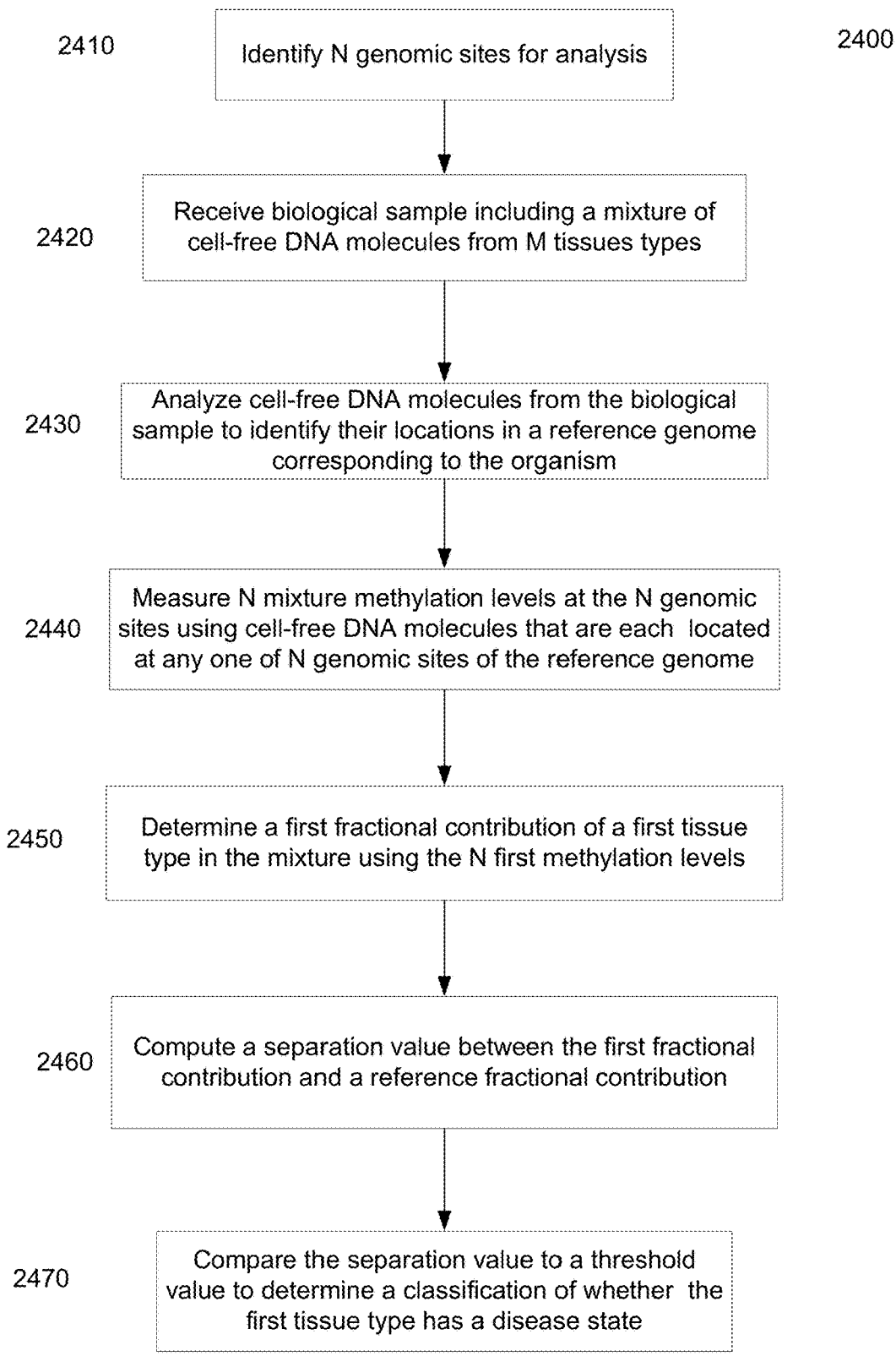
FIG. 24 is a flowchart illustrating a method of analyzing a DNA mixture of cell-free DNA molecules to identify a disease state in a tissue based on elevated fractional contribution of the tissue to the DNA mixture according to embodiments of the present invention.

FIG. 24 is a flowchart illustrating a method 2400 of analyzing a DNA mixture of cell-free DNA molecules to identify a disease state in a tissue based on elevated fractional contribution of the tissue to the DNA mixture according to embodiments of the present invention. The biological sample includes a mixture of cell-free DNA molecules from a plurality of tissues types, including a first tissue type.

At block 2410, N genomic sites are identified for analysis. The N genomic sites can have various attributes, e.g., as described above. As examples, the N genomic sites can include type I or type II sites only, or a combination of both. Block 2410 can be performed in a similar manner as block 110 of FIG. 1.

At block 2420, the biological sample including a mixture of cell-free DNA molecules from M tissues types is received. Block 2420 can be performed in a similar manner as block 130 of FIG. 1.

At block 2430, cell-free DNA molecules from the biological sample are analyzed to identify their locations in a reference genome corresponding to the organism. Block 2430 can be performed in a similar manner as block 140 of FIG. 1. The cell-free DNA molecules analyzed can be short DNA fragments, which can provide sufficient accuracy with a smaller number of DNA fragments, as explained in section IV.B below.

At block 2440, N mixture methylation levels are measured at the N genomic sites using cell-free DNA molecules that are each located at any one of N genomic sites of the reference genome. One mixture methylation level can be measured for each of the N genomic sites. Block 2440 can be performed in a similar manner as block 150 of method 100 of FIG. 1. Thus, any technique for measuring a methylation level of a DNA molecule may be used. In some embodiments, the measurement of the methylation level of a DNA molecule can use methylation-aware sequencing results, which may also be used to determine the location of the DNA molecule.

At block 2450, a first fractional contribution of the first tissue type in the mixture is determined using the N first methylation levels. In some embodiments, block 2450 can be performed via blocks 160 and 170 of method 100 of FIG. 1. Thus, a fractional contribution can be determined simultaneously for a panel of M tissue types. Block 2450 may use N issue-specific methylation levels at N genomic sites, determined for each of M tissue types, e.g., as in block 120 of method 100 of FIG. 1.

At block 2460, a separation value between the first fractional contribution and a reference fractional contribution is computed. As examples, the separation value can include a difference or a ratio of the first fractional contribution and the reference fractional contribution. The separation value can include other factors, and a difference of functions of the fractional contributions can be used. The reference fractional contribution can be determined using samples from organisms that are healthy for the first tissue type.

At block 2470, the separation value can be compared to a threshold value to determine a classification of whether the first tissue type has a disease state. As shown in results herein, a statistically significant increase in the amount of a particular tissue type to the mixture indicates a disease state. If the total of the contributions is constrained to be 1 (i.e., 100%), then an increase in the particular tissue type would be accompanied by corresponding decreases in one or more other tissues in the mixture. Accordingly, a first amount (e.g., a fractional contribution) of the first tissue type in the mixture can be compared to a threshold amount to determine a classification of whether the first tissue type has a disease state.

In one embodiment, the threshold value is determined based on amounts of the first tissue type in mixtures of a first set of organisms that are healthy for the first tissue type and of a second set of organisms that are diseased for the first tissue type. The diseased organisms can have a disease that is being tested for, e.g., cancer. For example, the second set of organisms may have cancer in the first tissue type. As another example, the second set of organisms can have a transplant of the first tissue type that has been rejected. For a transplant organ, the identification of a disease state can correspond to a classification of whether the first tissue type is being rejected by the organism, where the rejection is a disease state.

3. Systemic Lupus Erythematosus (SLE)

To further illustrate the potential utility of the plasma DNA methylation deconvolution analysis, we analyzed the plasma DNA of nine patients with SLE. These patients had SLE disease activity index (SLEDAI) of less than 8 indicating that their disease is relatively inactive. Plasma DNA methylation deconvolution was performed for these eight patients.

FIG. 25 is a table 2500 showing the percentage contribution of different organs to the plasma DNA by methylation deconvolution in nine SLE patients according to embodiments of the present invention. The contribution of the liver was increased in patients 8 and 9 compared with other SLE patients. Patient 8 had drug-induced hepatitis with an elevated alanine transaminase (ALT) activity of 235 U/L. Patient 9 had a disseminated tuberculosis involving the liver. These results suggest that the plasma DNA methylation deconvolution analysis was able to identify the pathology of the affected organ.

4. Identifying Tissue Type Associated with Detected Disease

The previous sections automatically determined the tissue type as part of identifying the disease when a large percentage of increase is seen. If a disease is identified by other means, then a smaller increase for a particular tissue type can allow the tissue type to be identified, even if the increase is not large enough to signify a disease state by itself. For example, if cancer was identified for above, the analysis above can identify the tissue involved. A further description of embodiments that identify the tissue type for a detected cancer is provided in section V.

B. Size Selection with Methylation Deconvolution

As an alternative or in addition to identifying elevated fractional contributions relative to the values from healthy tissues, embodiments can analyze fractional contributions for different sizes of cell-free DNA molecules. When performed in addition, certain tissue types can be identified as having elevated fractional contributions, and the size analysis can confirm whether the tissue type is diseased.

Regarding the size of cell free DNA molecules, it has been demonstrated that the size distribution of fetal-derived DNA is shorter than that of maternally derived DNA in the plasma of pregnant women. Furthermore, the size distribution of tumor-derived DNA is shorter than that of DNA derived from non-malignant tissues in cancer patients (Jiang et al. Proc Natl Acad Sci USA. 2015; 112:E1317-25). In this regard, the selective analysis of long and short DNA fragments would be able to identify enrichment for short cell-free DNA molecules from a particular tissue.

Accordingly, increased accuracy can be obtained by analyzing DNA fragments of a specific size. For example, an increased contribution of the liver to the plasma DNA would be observed in patients suffering from liver cancer. It has been demonstrated that plasma DNA molecules derived from the liver cancer are shorter than the plasma DNA derived from non-malignant tissues (Jiang et al. Proc Natl Acad Sci USA. 2015; 112:E1317-25). Therefore, an observation that the contribution from the liver is higher when short DNA molecules are analyzed compared with when long DNA molecules are analyzed would further support that the elevation of the liver contribution is compatible with the presence of liver cancer in the patient.

1. Results

Three maternal plasma samples and two plasma samples from cancer patients were sequenced using a paired-end sequencing protocol so that the coordinates of the outermost nucleotides on both ends of each plasma DNA molecule in the reference human genome could be determined. Then the size of each plasma DNA molecule was deduced from the coordinates of the nucleotides at the two ends.

To illustrate if the composition of plasma DNA would be different when short or long DNA molecules are selectively analyzed, we have arbitrarily used a cutoff of 150 bp to define long and short DNA molecules. Other examples of size cutoffs include 70 bp, 75 bp, 80 bp, 90 bp, 100 bp, 110 bp, 120 bp, 130 bp, 140 bp, 160 bp, 170 bp, 180 bp, 190 bp and 200 bp. Besides length, mass could also be used as a measure of size. As an example for mass spectrometry, a longer molecule would have a larger mass (an example of a size value). Length is another example of size, e.g., as measured in base pairs. The size selection can also be performed using a physical method, such as by gel electrophoresis or by filtration or by size-selective precipitation or by hybridization.

The results below show that size analysis can be used in combination with the analysis of tissue contribution of plasma DNA via methylation deconvolution. In some embodiments, the methylation deconvolution of plasma DNA can be focused on a specific size range of plasma DNA. As DNA molecules from non-hematopoietic tissues have a shorter size distribution, the selective analysis of short DNA fragments can give a more cost-effective analysis for the DNA released from the target organ. For example, to determine if the significant damage to a transplanted liver in a patient receiving liver transplantation, methylation deconvolution can be performed on short DNA fragments only. As non-hematopoietic tissues would have a higher fractional contribution to the plasma DNA when short DNA fragments are selectively analyzed, a statistical difference from reference values can be obtained with analyzing fewer cell-free DNA molecules. For example, the higher fractional contribution results in detectable changes (i.e., changes above a threshold) in the fractional contribution with fewer cell-free DNA molecules due to the higher concentration of cell-free DNA molecules from non-hematopoietic tissue. Accordingly, the cell-free DNA molecules analyzed in method 2400 can be below a size cutoff, which can provide a desired accuracy with fewer cell-free DNA molecules. The increase in liver contribution in this case can indicate increased cell death in the transplanted liver.

Figure 26A:
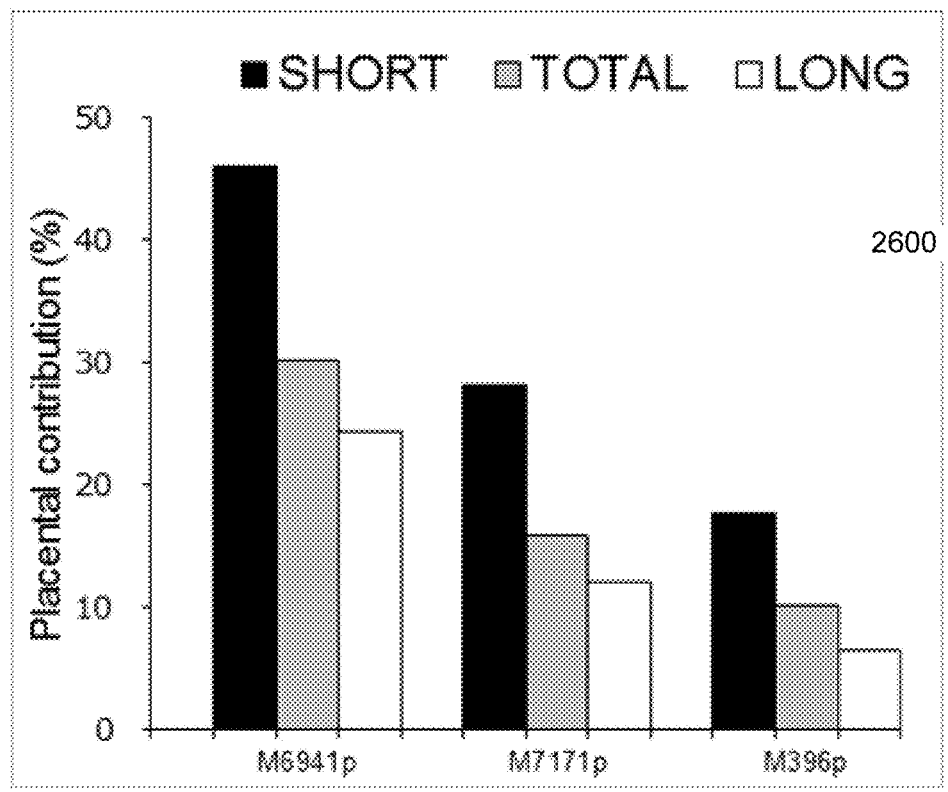
FIG. 26A is a graph showing the placental contributions determined from cell-free DNA molecules of different lengths for three pregnant women (M6941p, M7171p and M396p) according to embodiments of the present invention.

FIG. 26A is a graph 2600 showing the placental contributions determined from cell-free DNA molecules of different lengths for three pregnant women (M6941p, M7171p and M396p) according to embodiments of the present invention. The contributions from the placenta to plasma DNA were higher when only the short plasma DNA fragments of <150 bp were analyzed compared with the analysis involving all plasma DNA without size selection. In contrast, the contributions from the placenta to plasma DNA was lower when only the long plasma DNA fragments of ≥150 bp were analyzed compared with the analysis involving all plasma DNA without size selection.

These results are consistent with the size distribution of placentally-derived DNA (with the same genotype of the fetus) being shorter than that of maternally-derived DNA. Such results indicate that embodiments can be used to detect a condition in a specific tissue type.

Figure 26B:
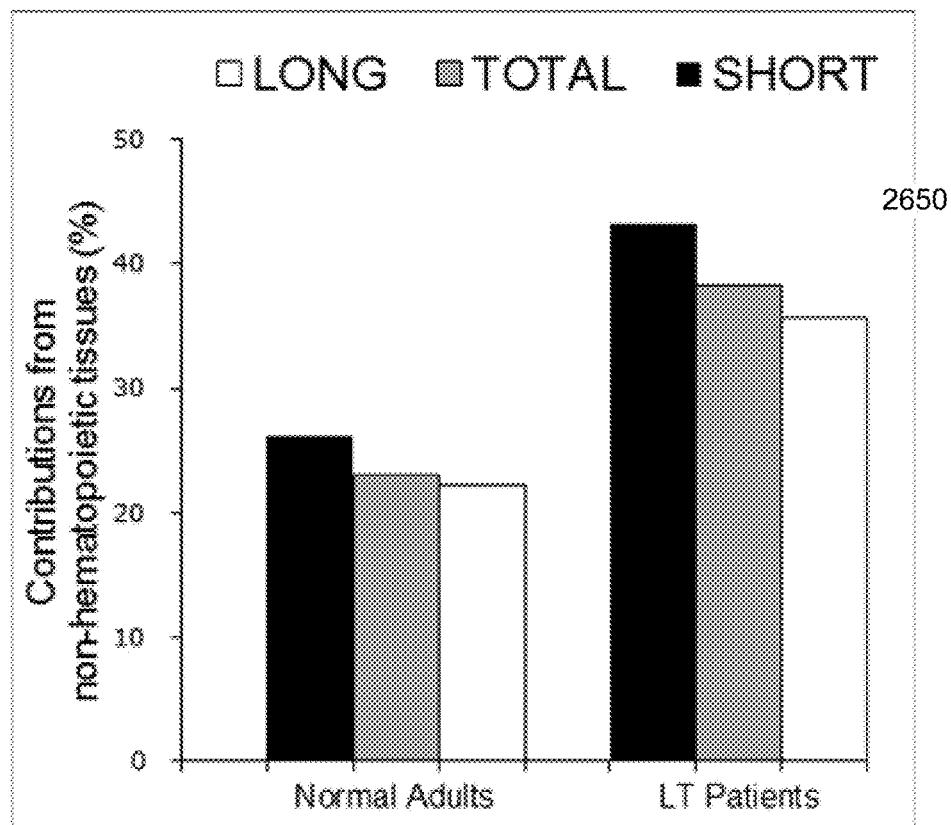
FIG. 26B is a graph showing contributions of non-hematopoietic tissues determined from cell-free DNA molecules of different lengths for transplant patients according to embodiments of the present invention.

FIG. 26B is a graph 2650 showing contributions of non-hematopoietic tissues determined from cell-free DNA molecules of different lengths for transplant patients according to embodiments of the present invention. The sequenced reads of the five patients who had received liver transplantation (LT patients) were pooled together for the analysis. As controls, the sequenced reads of four healthy controls were pooled together for this analysis. We observed that the proportional contribution of the non-hematopoietic tissues increased when only the short plasma DNA fragments of <150 bp were analyzed compared with the analysis involving all plasma DNA without size selection. The proportion contribution decreased when only the long plasma DNA fragments of ≥150 bp were analyzed compared with the analysis involving all plasma DNA without size selection.

Such results also indicate that embodiments can identify conditions in organs. Although embodiments would not typically be used to identify the transplanted organ, embodiments can monitor a separation value (e.g., difference or ratio) between the fractional contributions for different sizes. Problems with the transplanted organ can be identified when the separation value increases.

Figure 27A:
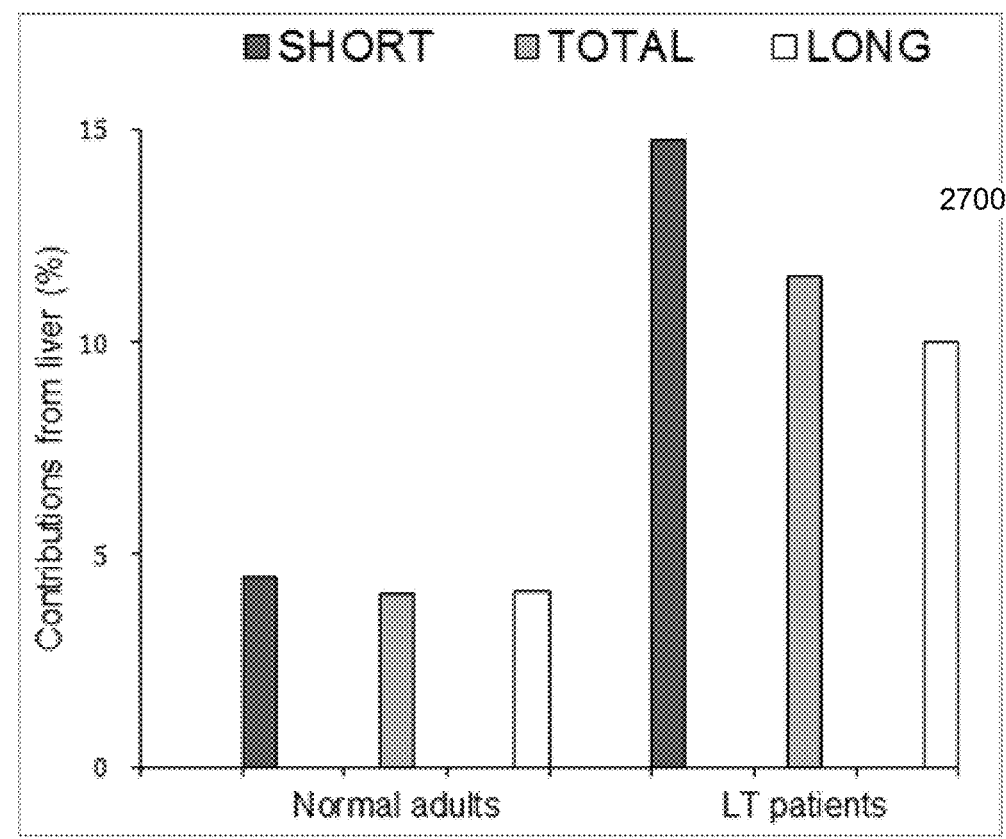
FIG. 27A is a graph showing contributions of the liver determined from cell-free DNA molecules of different lengths for transplant patients according to embodiments of the present invention.

FIG. 27A is a graph 2700 showing contributions of the liver determined from cell-free DNA molecules of different lengths for transplant patients according to embodiments of the present invention. The proportional contribution of the liver was also analyzed for the healthy control subjects and patients who had received liver transplantation. The proportional contribution of the liver increased when the short DNA fragments were analyzed and the proportional contribution of the liver decreased when the long DNA fragments were analyzed, relative to the analysis involving all plasma DNA without size selection.

The contribution from the liver was higher when short DNA fragments in plasma were analyzed, than when long DNA fragment were analyzed. Further, the amount of difference is greater than for non-hematopoietic tissue, which includes other tissues besides the liver. Such results further illustrate the ability to pinpoint the tissue having a condition associated with an increase in shorter cell-free DNA molecules.

Figure 27B:
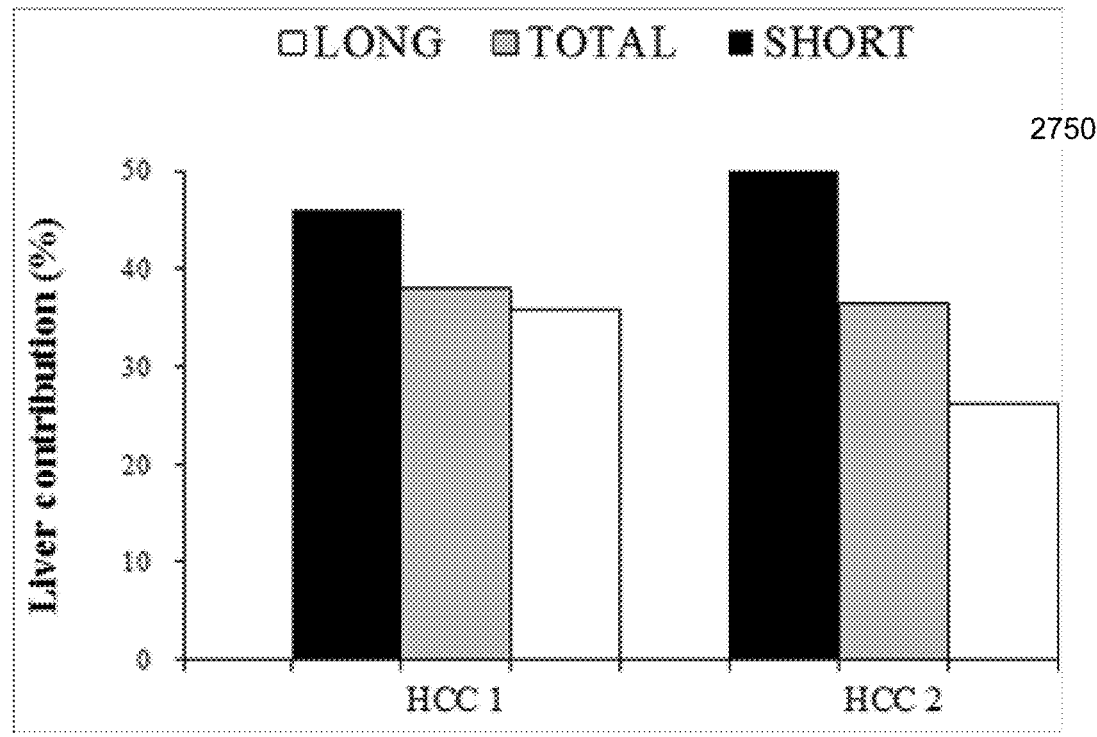
FIG. 27B is a graph showing contributions of the liver determined from cell-free DNA molecules of different lengths for HCC patients according to embodiments of the present invention.

FIG. 27B is a graph 2750 showing contributions of the liver determined from cell-free DNA molecules of different lengths for HCC patients according to embodiments of the present invention. The proportional contribution of the liver was analyzed for two HCC patients. The proportional contribution of the liver increased when the short DNA fragments were analyzed and the proportional contribution of the liver decreased when the long DNA fragments were analyzed, relative to the analysis involving all plasma DNA without size selection.

Accordingly, embodiments can analyze a separation between the fractional contributions for long and short cell-free DNA molecules to identify a tissue that is diseased. Such separation values can be determined for each of a panel of tissue types. When a particular separation value for a particular tissue type is above a threshold, then a tissue type can be classified as corresponding to a diseased state. As one can see, the differential for a normal organism is just a few percent, where the differential is near 8% or more for the HCC cases.

2. Method

Figure 28:
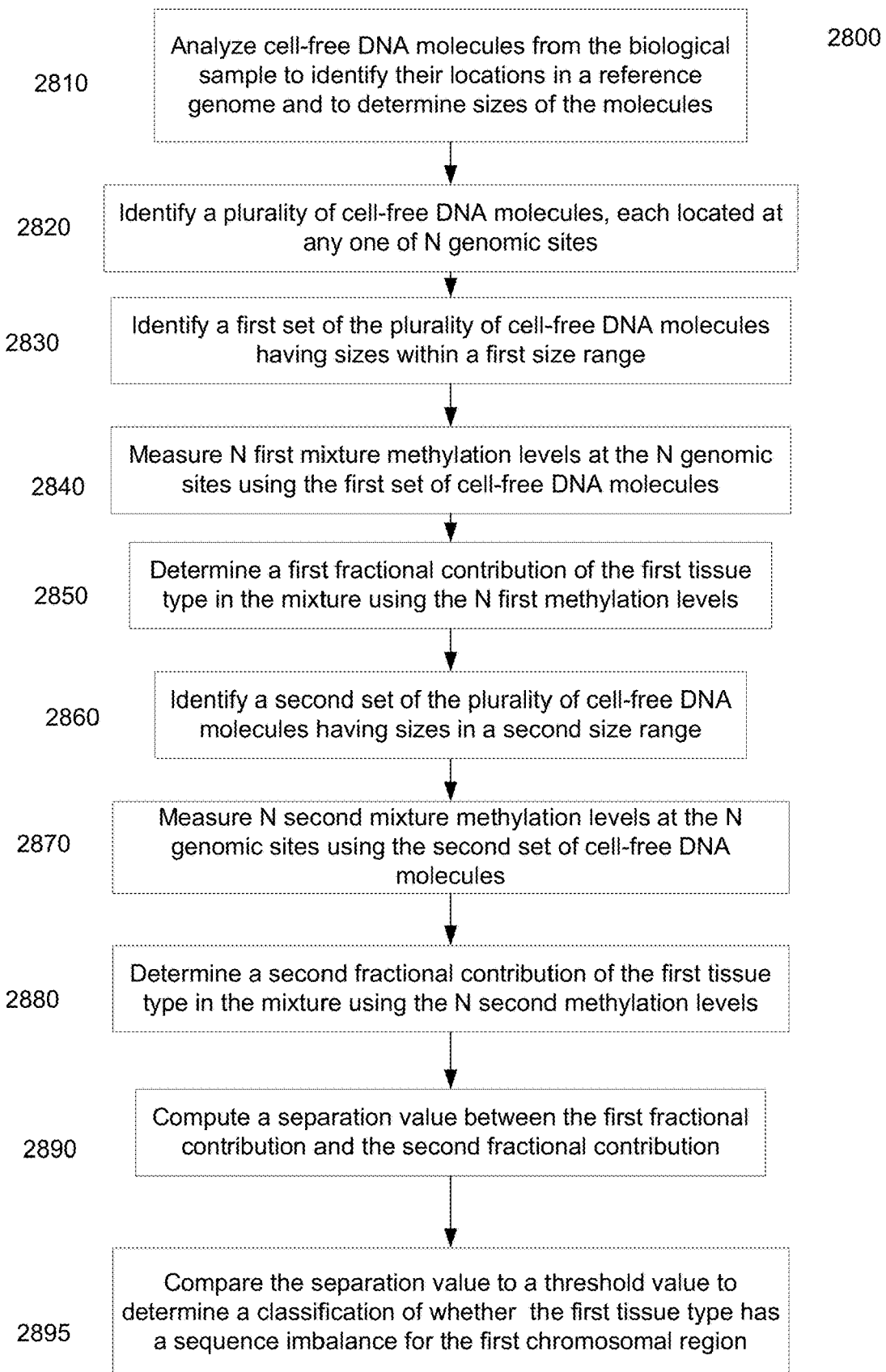
FIG. 28 is a flowchart illustrating a method of analyzing a DNA mixture of cell-free DNA molecules to identify a disease state in a tissue based on differential fractional contribution of the tissue to the DNA mixture from cell-free DNA molecules of different sizes according to embodiments of the present invention.

FIG. 28 is a flowchart illustrating a method 2800 of analyzing a DNA mixture of cell-free DNA molecules to identify a disease state in a tissue based on differential fractional contribution of the tissue to the DNA mixture from cell-free DNA molecules of different sizes according to embodiments of the present invention. A biological sample includes the mixture of cell-free DNA molecules from a plurality of tissues types, including a first tissue type.

At block 2810, a plurality of cell-free DNA molecules from the biological sample are analyzed. Block 2810 can be performed in a similar manner as block 140 of method 100 of FIG. 1. For example, at least 1,000 cell-free DNA molecules can be analyzed to determine where the cell-free DNA molecules are located, and methylation levels can be measured as described below.

Further, a size of each of the plurality of cell-free DNA molecules can be measured. The sizes can be measured in a variety of ways. For instance, the cell-free DNA molecules can be sequenced (e.g., using methylation-aware sequencing) to obtain sequence reads, and a size can correspond to a length of a sequence read. The sequence reads can be aligned to a reference genome to determine where a cell-free DNA molecule is located. In one implementation, the sequencing includes sequencing two ends of each of the cell-free DNA molecules, and the aligning includes aligning the two ends. The sizes of the plurality of cell-free DNA molecules can be determined based on the alignment of the two ends to the reference genome.

The determination of the location and the size may be performed in different procedures, e.g., a physical separation can be performed, and then a location can be determined (e.g., using sequencing or hybridization probes). Examples of the physical separation process include gel electrophoresis, filtration, size-selective precipitation, or hybridization. The physical separation process can be performed before the analyzing the cell-free DNA molecules to determined their location. In one implementation, the locations can be determined using hybridization probes. In other embodiments (e.g., sequencing), the size of each of the plurality of cell-free DNA molecules can be determined.

At block 2820, a plurality of cell-free DNA molecules are identified that are each located at any one of N genomic sites of the reference genome corresponding to the organism. As long as a cell-free DNA molecule includes one of the N genomic sites, it can be included. The N genomic sites can be identified in various ways and using various criteria, as described herein. Techniques described in section II may be used. N is an integer, which may be greater than or equal to 10.

At block 2830, a first set of the plurality of cell-free DNA molecules is identified that have sizes within a first size range. The first size range can correspond to any size range, e.g., less than a specified length, greater than a specified length, or between two sizes. The first set may be identified by physical process (e.g., as described herein) or by knowing the size of each DNA molecules and identifying them on a computer.

At block 2840, N first mixture methylation levels are measured at the N genomic sites using the first set of the plurality of cell-free DNA molecules. One first mixture methylation level can be measured for each of the N genomic sites. Block 2840 can be performed in a similar manner as block 150 of method 100 of FIG. 1.

At block 2850, a first fractional contribution of the first tissue type in the mixture is determined using the N first methylation levels. In some embodiments, block 2850 can be performed via blocks 160 and 170 of method 100 of FIG. 1. Thus, a fractional contribution can be determined simultaneously for a panel of M tissue types.

At block 2860, a second set of the plurality of cell-free DNA molecules is identified that have sizes within a second size range. The second size range is different than the first size range. The second size range can correspond to any size range, e.g., less than a specified length, greater than a specified length, or no size selection (i.e., all sizes), as long as it is difference from the first size range. When the second size range has no size selection, the first size range would a subset of the second size range.

In some embodiments, the two size ranges do not overlap, whereas in other embodiments an overlap can exist. The size ranges would not be centered at a same size, but would be offset, potentially with no overlap. In one embodiment, the first size range is less than 150 bases and the second size range is 150 bases and higher.

At block 2870, N second mixture methylation levels are measured at the N genomic sites using the second set of the plurality of cell-free DNA molecules. One second mixture methylation level can be measured for each of the N genomic sites. Block 2870 can be performed in a similar manner as block 2840.

At block 2880, a second fractional contribution of the first tissue type in the mixture is determined using the N second methylation levels. Block 2880 can be performed in a similar manner as block 2850.

At block 2890, a separation value between the first fractional contribution and the second fractional contribution is computed. Examples of a separation value are described herein, and include a difference or a ratio. If a tissue type contributes relatively more short DNA molecules to the mixture, the fractional contribution will be higher for the size range that is shorter.

At block 2895, the separation value is compared to a threshold value to determine a classification of whether the first tissue type has a disease state. A classification can be that the first tissue type has the disease state when the separation value exceeds the threshold value. The disease state can identify something wrong (e.g., cancer) with the tissue as a result of releasing a disproportionate amount of shorter cell-free DNA molecules. The threshold could be defined as a negative number or absolute values can be determined.

In some embodiments, the threshold value can determined based on separation values determined for mixtures of a first set of organisms that are healthy for the first tissue type and of a second set of organisms that are diseased for the first tissue type. Various classifications can account for how much the separation value exceeds the threshold value. Accordingly, multiple thresholds can be used, as can be done for any method described herein.

V. Identifying Tissue Corresponding to Copy Number Aberration

Copy number aberrations correspond to amplifications and deletions in chromosomal regions, e.g., an entire chromosome or part of a chromosome. A copy number aberration (CNA) exists in many tumors and can thus indicate the existence of cancer or other disease. Further details of identifying cancer by detecting regions exhibiting CNA can be found in U.S. Pat. No. 8,741,811, which is incorporated by reference. But, one may not know the origin of the tumor strictly from the CNA analysis. Embodiments can use methylation deconvolution to identify an origin of the cell-free DNA molecules that corresponds to the copy number aberrations. Embodiments can also use methylation deconvolution to test a particular chromosomal region.

For example, plasma consists of DNA released from multiple tissues within the body. Using genome-wide bisulfite sequencing of plasma DNA, we have obtained the contributions of these tissues to the circulating DNA pool. The tissue contributors and their relative proportions are identified by a bioinformatics deconvolution process that draws reference from DNA methylation signatures representative of each tissue type, as described above. We validated this approach in pregnant women, cancer patients and transplant recipients. Embodiments allow one to identify the tissue of origin of genomic aberrations observed in plasma DNA. This approach has numerous research and diagnostic applications in prenatal testing, oncology, transplantation monitoring and other fields.

A. Tissue Mapping of Copy Number Aberrations (CNAs)

The detection of copy number aberrations in plasma has been used in the contexts of noninvasive prenatal testing (Chiu R W K, et al. (2008) *Proc Natl Acad Sci USA* 105:20458-20463; Chiu R W K, et al. (2011) *BMJ* 342: c7401; Bayindir B, et al. (2015) *Eur J Hum Genet* doi: 10.1038/ejhg.2014.282; and Norton M E, et al. (2015) *N Engl J Med* 372:1589-1597) and cancer detection (Leary R J, et al. (2012) *Sci Transl Med* 4(162):162ra154; Chan et al. Proc Natl Acad Sci USA. 2013; 110:18761-8; Heitzer E, et al. (2013) *Int J Cancer* 133(2):346-356). It would be highly advantageous if one could identify the tissue of origin of the copy number aberrations.

For the noninvasive prenatal detection of subchromosomal copy number aberrations (Yu S C Y, et al. (2013) *PLoS One* 8(4):e60968), it would be useful to identify if the plasma aberrations have originated from (i) the placenta alone, (ii) the mother alone, or (iii) both the placenta and the mother. For cancer screening, it would be clinically very informative to be able to identify the tissue of origin of the cancer for subsequent diagnostic or therapeutic procedures.

Copy number aberrations are commonly observed in different types of cancer. Cancer-associated copy number aberrations can be detected in the plasma of cancer patients (Chan et al. Clin Chem. 2013; 59: 211-24). In the context of cancer screening, the tissue of origin for the CNA may not be apparent. Therefore, it is useful if the tissue of origin of the CNA can be identified. Plasma DNA methylation deconvolution can be used to identify the tissue of origin of the plasma CNA.

Figure 29:
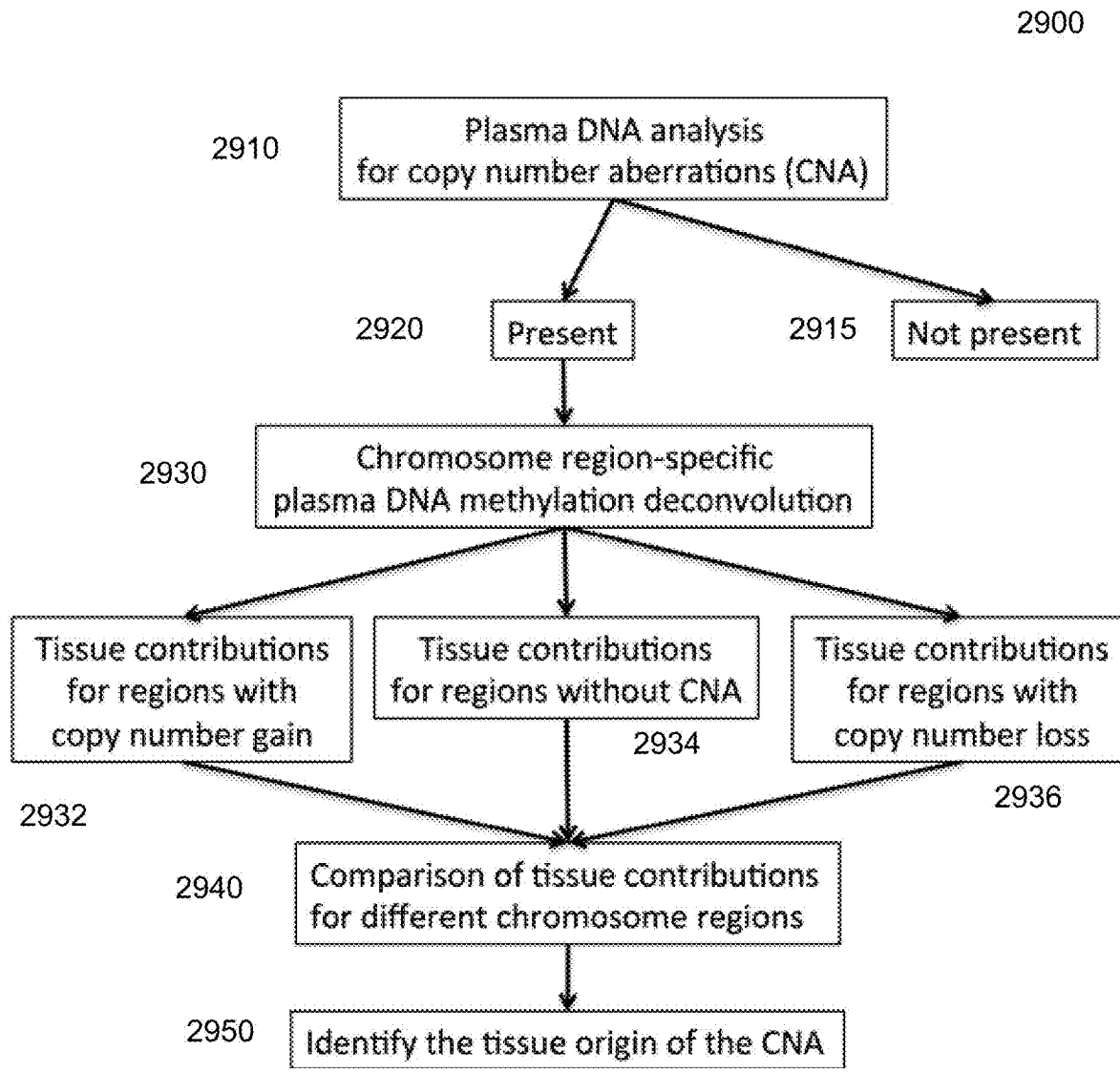
FIG. 29 is a flow chart illustrating a method 2900 for determining the tissue of origin for copy number aberrations according to embodiments of the present invention.

FIG. 29 is a flow chart illustrating a method 2900 for determining the tissue of origin for copy number aberrations according to embodiments of the present invention. Method 2900 may be performed using plasma of a patient and is performed at least partially using a computer system.

At block 2910, plasma DNA analysis is performed to identify regions that exhibit copy number aberrations. The aberration can correspond to over or under-representation. In some embodiments, the genome can be separated into bins (e.g., 1-Mb bins), and the amount of cell-free DNA molecules from a particular bin can be determined (e.g., by mapping sequence reads to that part of a reference genome). The amount for a particular bin can be normalized (e.g., with respect to an average amount for a bin) can an over or under-representation can be identified.

Besides identifying regions based on CNA analysis, a region can simply be selected for testing in various embodiments. For instance, a region can be suspected for having CNA, e.g., as certain regions may commonly have aberrations in tumors. Or, for fetal application (described below), certain chromosomal regions may commonly have aberrations.

At block 2915, no CNA regions are identified. Method 2900 can stop at this point, in some embodiments.

At block 2920, methylation deconvolution can be performed, e.g., as described in FIG. 1. At block 2930, a methylation deconvolution can be performed for each of the CNA regions. Accordingly, a chromosome region-specific plasma DNA methylation deconvolution can be performed.

At block 2932, tissue contributions for regions with copy number gain are obtained, as a result of the methylation deconvolution. At block 2934, tissue contributions for regions without CNA are obtained, as a result of the methylation deconvolution. At block 2936, tissue contributions for regions with copy number loss are obtained, as a result of the methylation deconvolution.

At block 2940, the tissue contributions for different chromosomal regions can be compared. For example, separation values for these various tissue contributions can be determined. For any two regions, a separation value for a particular tissue can be determined. The separation values would be between a region with a copy number gain and a region without CNA, between a region with a copy number gain and a region with a copy number loss, and between and a region without CNA and a region with a copy number loss.

At block 2950, the identity of the tissue of origin can be identified based on how large the separation values are for the tissues. A tissue with a large contribution would be releasing cell-free DNA molecules with the aberration tested.

For this application, it is advantageous to have methylation markers that are spread across the genome. In this regard, the type II methylation markers, due to their relatively larger numbers when compared with the type I markers, are especially useful. For certain embodiments, one can further adjust the selection criteria for the markers so as to further increase the number of markers that one can use. In yet other embodiments, one can combine both type I and type II markers to further increase the number of markers that one can use.

B. Identifying Aberrant Regions

The CNA analysis may be performed in a variety of ways, e.g., as described in U.S. Pat. No. 8,741,811. For example, the human genome (or genome for other type of organism) can be partitioned into approximately 3000 non-overlapping 1-Mb bins. The number of reads mapping to each 1-Mb bin can be determined. After correcting for GC bias (Chen E Z, et al. (2011) *PLoS One* 6(7):e21791), the sequence read density of each bin can be calculated. For each bin, the sequenced read density of the test case can be compared to the values of the reference control subjects. Copy number gains and losses may be defined as 3 standard deviations above and below, respectively, the mean of the controls. Accordingly, identifying a first chromosomal region as exhibiting a copy number aberration can be based on a first amount of cell-free DNA molecules that are located in the first chromosomal region.

To determine the tissue origin of copy number aberrations in plasma, plasma DNA tissue mapping can be performed using the methylation markers located within the genomic regions exhibiting such aberrations in plasma. In the examples below for the cancer patients, mapping of plasma DNA copy number aberrations was performed only in cases with aberrations affecting a contiguous chromosome region of at least 30 Mb so that a sufficient number of methylation markers could be used for mapping.

C. Examples for Detecting Origin of CNA

Methylation deconvolution to identify the tissue of origin of plasma copy number aberrations. For example, when a copy number gain is observed in plasma, methylation deconvolution of markers located within the affected genomic region should reveal increased contribution by the tissue of origin of the aberration when compared to the same analysis conducted on a genomic region without copy number aberration. Conversely, when a copy number loss is observed in plasma, methylation deconvolution of markers located within the affected genomic region should reveal decreased contribution by the tissue of origin of the aberration. In the following sections, we illustrate the use of this concept in pregnant women carrying fetuses affected by trisomy 21, in HCC patients and in a pregnant woman suffering from lymphoma. In these examples, it is not required that the identified regions be known to have a CNA; and in that case, the techniques can be used to determine whether a sequence imbalance does exist for the tested region.

1. Fetal Abnormalities

Figure 30A:
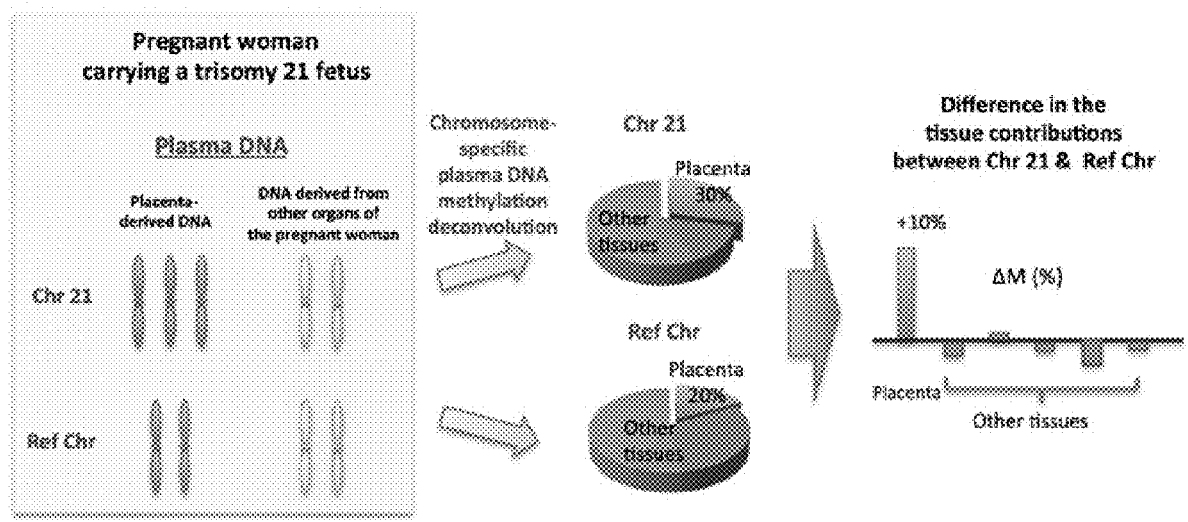
FIG. 30A shows an illustration of the analysis of chromosome-specific plasma DNA methylation deconvolution in a pregnant woman carrying a trisomy 21 according to embodiments of the present invention.

FIG. 30A shows an illustration of the analysis of chromosome-specific plasma DNA methylation deconvolution in a pregnant woman carrying a trisomy 21 according to embodiments of the present invention. A fetus with trisomy 21 would release an increased amount of chromosome 21 sequences carrying a placental methylation signature into the plasma of its pregnant mother. Hence, when one performs methylation deconvolution on the plasma bisulfite sequencing data using markers present on chromosome 21, the placental contribution (denoted as $M_{Placenta}^{Chr21}$) will be expected to be increased as compared to the placental contribution estimated using markers present on the other chromosomes (denoted as $M_{Placenta}^{Refchr}$).

In this illustration, it is assumed that the fetal DNA fraction in the maternal plasma is 20%. Because of the extra copy of chromosome 21 in the fetus, the contribution of the placentally-derived DNA would increase by 50% when the methylation deconvolution analysis was performed based on the markers on chromosome 21 compared with using markers on one or more reference chromosomes.

Accordingly, embodiments can determine a fractional contribution using cell-free DNA molecules from chromosome 21 in the methylation deconvolution process, resulting in a fractional contribution of 30% for the placental tissue. The methylation deconvolution is also performed using cell-free DNA molecules from one or more reference chromosomes, resulting in a fractional contribution of 20% for the placental tissue. The differences in the fractional contributions for the various tissues can then be determined to detect whether chromosome 21 has a sequence imbalance (e.g., a trisomy in this example).

Here, we denote ΔM as the difference in the contribution to plasma DNA by different organs between chromosome 21 and the one or more chromosomes (denoted as Ref Chr).

$$\Delta M = M^{Chr21} - M^{Ref\ Chr}$$

where $M^{Chr21}$ is the contribution of a tissue to plasma DNA based on markers on chromosome 21 and $M^{Ref\ Chr}$ is the contribution of a tissue to plasma DNA based on markers on the reference chromosomes. Thus, ΔM is an array of contribution differences, each corresponding to a different tissue. Hence, embodiments can compute:

$$\Delta M_{Placenta} = M_{Placenta}^{Chr21} - M_{Placenta}^{Refchr}.$$

The other ΔM values for each of the other tissue types involved in the methylation deconvolution would be computed in a similar manner. If the placenta is the origin of the increased copy number of chromosome 21 in the maternal plasma, then the ΔM value for the placenta will be expected to be the highest when compared with those from the other tissue types.

To further illustrate this technique, we analyzed the plasma from 5 pregnant women each carrying a trisomy 21 fetus. The gestational ages ranged between 13 to 14 weeks. Increased representation of chromosome 21 was observed in the plasma DNA of each case. We performed methylation deconvolution on the sequencing data and ΔM values were calculated for multiple tissue types.

Figure 30B:
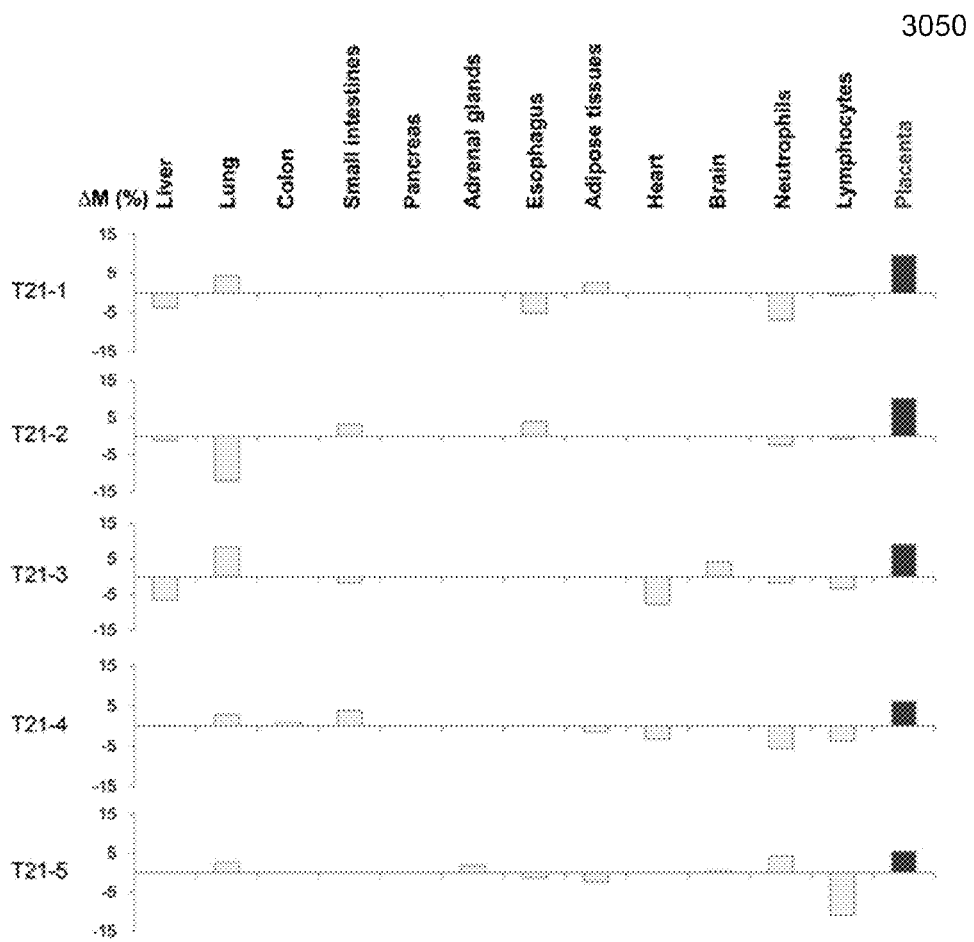
FIG. 30B is a diagram 3050 showing separation values ΔM of chromosome 21 across different tissues for pregnant women each carrying a fetus with trisomy 21 (T21) according to embodiments of the present invention

FIG. 30B is a diagram 3050 showing separation values ΔM of chromosome 21 across different tissues for pregnant women each carrying a fetus with trisomy 21 (T21) according to embodiments of the present invention. In each of the five cases, the value of ΔM was highest for the placenta suggesting that the copy number aberrations originated from the placenta. And, even if a CNA had not previously been identified for chromosome 21, the high value of ΔM for the placental tissue indicates that there was an aberration in chromosome 21 for the placental tissue.

Figure 31:
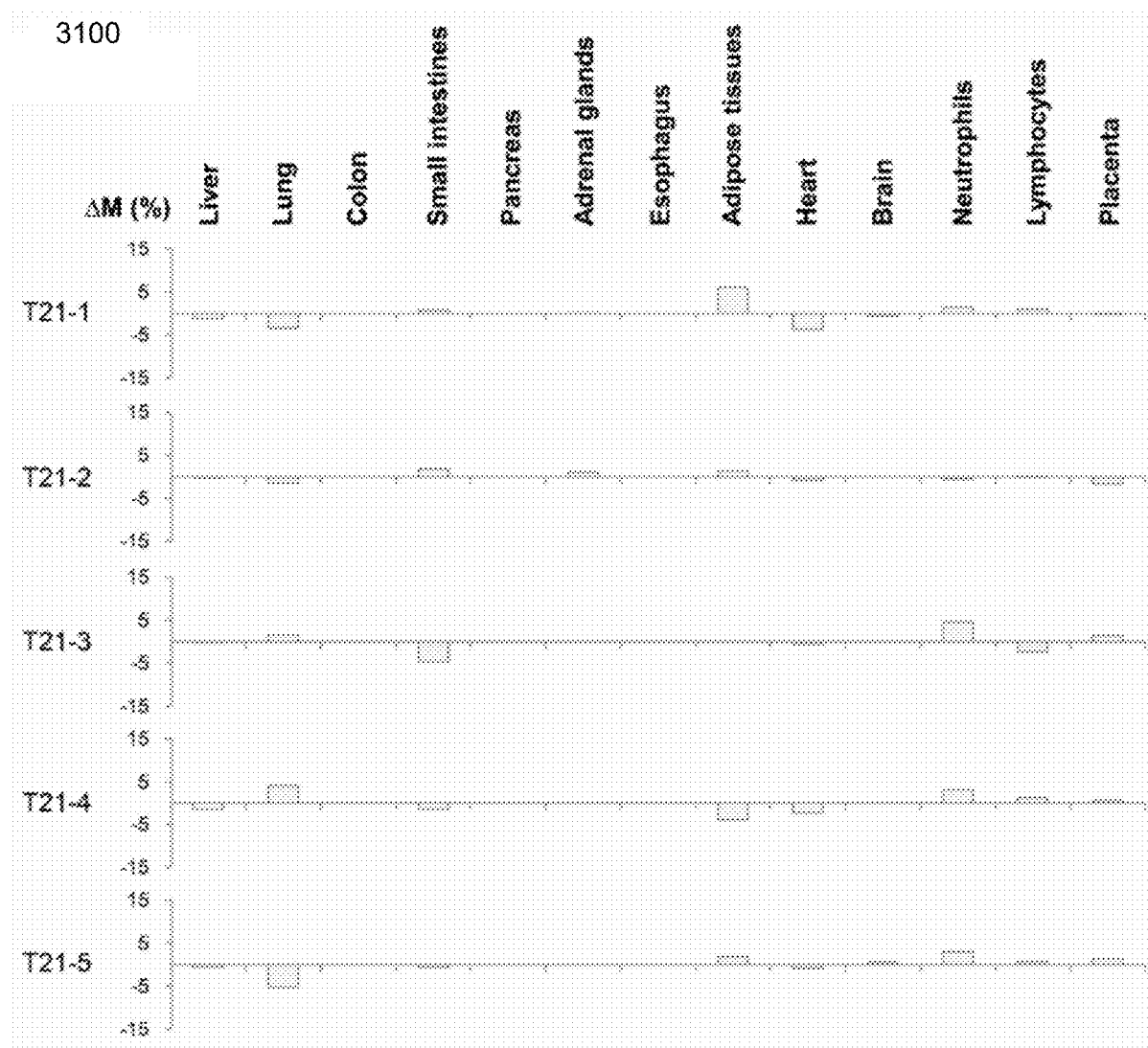
FIG. 31 is a diagram showing separation values ΔM of other chromosomes across different tissues for pregnant women each carrying a fetus with trisomy 21 (T21) according to embodiments of the present invention.

FIG. 31 is a diagram 3100 showing separation values ΔM of other chromosomes across different tissues for pregnant women each carrying a fetus with trisomy 21 (T21) according to embodiments of the present invention. The methylation markers on all the autosomes except chromosome 21 were randomly divided into two sets, namely, set A and set B. The randomization was implemented using a series of random numbers (ranged from 0 to 1) generated by a computer. A marker associated with a random number less than 0.5 was assigned to set A, otherwise it would be assigned to set B. In this analysis, set A included markers originating from chromosomes 1, 2, 4, 5, 6, 8, 12, 14, 15, 17, 22 and set B included markers originating from chromosomes 3, 7, 9, 10, 11, 13, 16, 18, 19, 20. Plasma DNA tissue mapping was conducted using each set of markers. The ΔM values shown represent the difference in contributions of a particular tissue to plasma DNA using markers in sets A and B. As can be seen, no single tissue consistently showed a raised ΔM value.

Plasma DNA methylation deconvolution analysis can also be useful to determine if a CNA has originated from the mother or the fetus, for example, in the noninvasive prenatal testing of microdeletion or microduplication using maternal plasma DNA analysis. Recently, it has been shown that microdeletion or microduplication of a fetus can be detected using maternal plasma DNA analysis (Yu et al. PLoS One 2013; 8: e60968). However, when a microdeletion or microduplication is detected in the maternal plasma DNA, the aberration can be arisen from the mother, the fetus or both of them. Methylation deconvolution analysis can be used to resolve this question.

Consider the scenario that a pregnant woman is normal and the fetus is carrying a microduplication. If we perform chromosome-specific methylation deconvolution on the duplicated region and other normal regions for the maternal plasma DNA, the value of ΔM would be most positive for the placenta indicating an additional dosage of placental DNA is released into the plasma at the duplicated region. On the other hand, for the scenario where the mother is a carrier of the microduplication and the fetus is normal, the contribution of the placental DNA to maternal plasma would be relatively reduced at the duplicated region because the maternal tissues would contribute more to the plasma DNA when compared with the fetus at the duplicated region. If both the mother and the fetus are carriers of the microduplication, then the proportional contribution of the mother and the fetus would not be different at the affected and unaffected chromosomal regions. The reverse would hold true for the scenarios involving microdeletion. The expected changes of ΔM in different scenarios are shown in the table below.

TABLE 3

Expected values of ΔM for scenarios with different copy number changes in a pregnant woman and her fetus.

| | Copy number change | | ΔM for placenta (Affected region minus unaffected |
| --- | --- | --- | --- |
| Scenarios | Mother | Fetus | region) |
| 1 | Normal | Increase | The largest positive value |
| 2 | Increase | Normal | The largest negative value |
| 3 | Increase | Increase | Close to zero |
| 4 | Normal | Decrease | The largest negative value |
| 5 | Decrease | Normal | The largest positive value |
| 6 | Decrease | Decrease | Close to zero |

In certain embodiments, the fetus or mother, or both can carry more than one copy number aberration for different regions. As an example, the fetus can carry both a microduplication, as well as a microdeletion for different regions.

2. Hepatocellular Carcinoma (HCC)

Some embodiments can also be used to determine an original of a CNA resulting from a tumor. In patients where the site of the tumor is unclear at the time of presentation, the methylation deconvolution analysis of the CNAs of plasma DNA would be useful for the identification of the origin of the cancer.

Figure 32A:
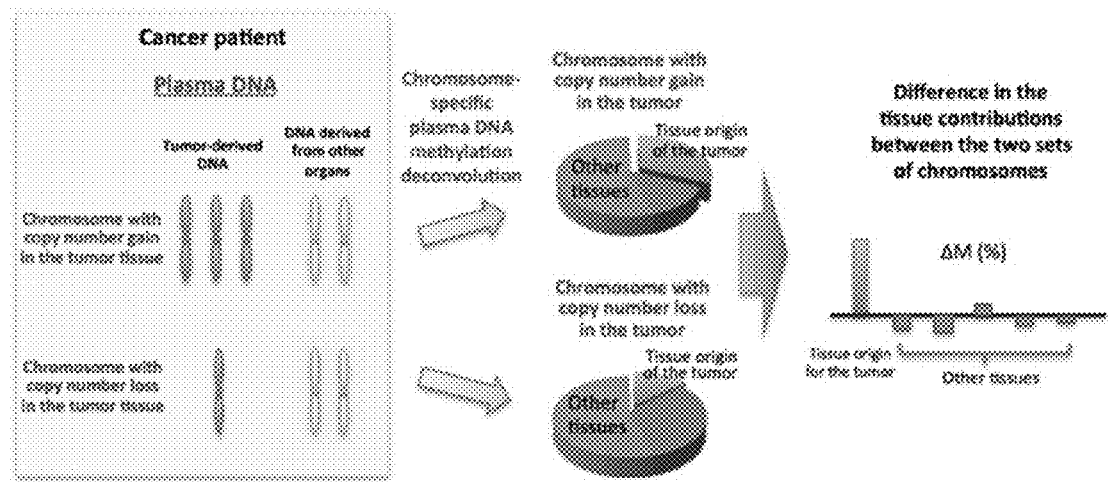
FIG. 32A is an illustration of the analysis of CNA regions in the plasma DNA of cancer patients according to embodiments of the present invention.

FIG. 32A is an illustration of the analysis of CNA regions in the plasma DNA of cancer patients according to embodiments of the present invention. In cancer patients, genomic regions in which there were increased copy numbers (i.e. amplifications) would be expected to be enriched in DNA released from the tissues of origin of the respective cancers. One would therefore observe an increase in the proportional contributions of the tissues of origin of the cancer in plasma (denoted as $M_{Tissue}^{Amp}$). In contrast, genomic regions in which there were decreased copy numbers (i.e. deletions) would be expected to be depleted in DNA released from the tissues of the respective cancers. One would then observe a decrease in the proportional contributions of the tissues of origin of the cancer in plasma (denoted as $M_{Tissue}^{Del}$).

Similar to the trisomy 21 example above, one can define a value ΔM using the following equation, where, $$\Delta M_{Tissue} = M_{Tissue}^{Amp} - M_{Tissue}^{Del}.$$

For tissues which were not the tissues of origin of the cancer, there would not be any systematic effect by the copy number aberrations (i.e. amplifications or deletions) on their proportional contributions to plasma. Hence, in such an analysis, the ΔM value would be the highest for the tissues of origin of the cancer, when compared with those from the other tissue types.

In other embodiments, the ΔM can be calculated by comparing the genomic regions showing amplification and regions showing normal copy number. In yet other embodiments, ΔM can be calculated by comparing the genomic regions showing deletion and regions showing normal copy number.

As examples, the plasma DNA of seven HCC patients, one lung cancer patient, and one colorectal cancer patient were analyzed. All of these nine patients had CNAs detected in the plasma. To determine the tissue of origin for these CNAs detected in plasma, methylation deconvolution for chromosomal regions exhibiting copy number gains and copy number losses was performed. Amongst the HCC, lung cancer and colorectal cancer samples studied above, copy number aberrations affecting at least a 30 Mb region (i.e. ~1% of the human genome) were observed in the plasma of 7 HCC, 1 lung cancer and 1 colorectal cancer patients.

The proportional contributions of each tissue type into plasma based on the genomic regions showing amplifications and deletions were separately determined. The differences in the contributions for each tissue type between the two sets of genomic regions were calculated and are denoted as ΔM, where ΔM is an array of the differences for the tissue types. Thus, $$\Delta M = M^{Amp} - M^{Del}$$

where $M^{Amp}$ is an array that represents the tissue contributions based on markers located in genomic regions exhibiting copy number gains; and $M^{Del}$ is an array that represents the tissue contributions based on markers located in genomic regions exhibiting copy number losses.

Figure 32B:
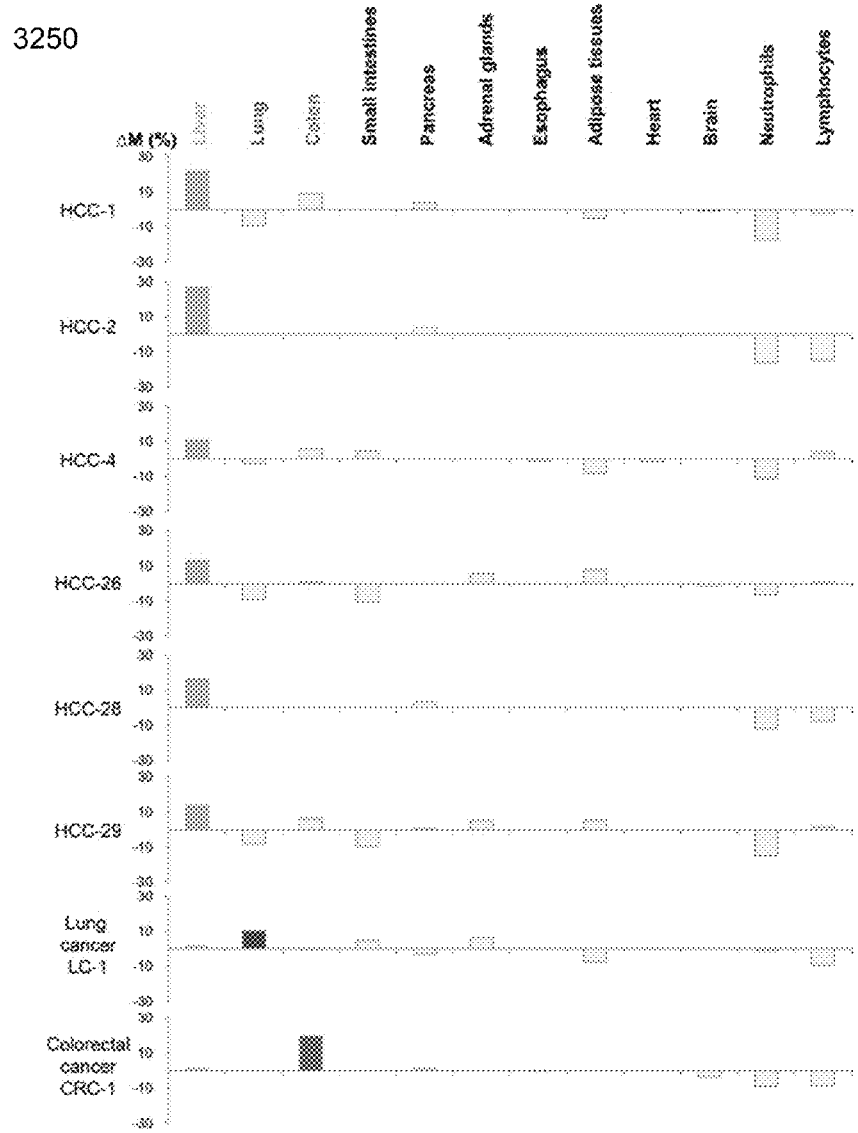
FIG. 32B is a diagram showing separation values ΔM between regions exhibiting copy number gains and copy number losses across different tissues for the cancer patients according to embodiments of the present invention.

FIG. 32B is a diagram 3250 showing separation values ΔM between regions exhibiting copy number gains and copy number losses across different tissues for the cancer patients according to embodiments of the present invention. In this example, the ΔM values across different tissues for the cancer patients. ΔM represents the difference in the contributions of a particular tissue to plasma DNA between regions exhibiting copy number gains and copy number losses.

For each case, the highest ΔM is shown in yellow, blue or green. Other ΔM values are shown in grey. The tissue with the highest ΔM is considered as the tissue of origin of the copy number aberration. The difference in contribution to plasma DNA between genomic regions with copy number gains and copy number losses (ΔM) was highest for the liver, lung and colon for the seven HCC patients, the lung cancer patient, and the colorectal cancer patient, respectively. Thus, the methylation deconvolution analysis correctly indicated the tissue of origin for the CNAs in the plasma samples.

Figure 33:
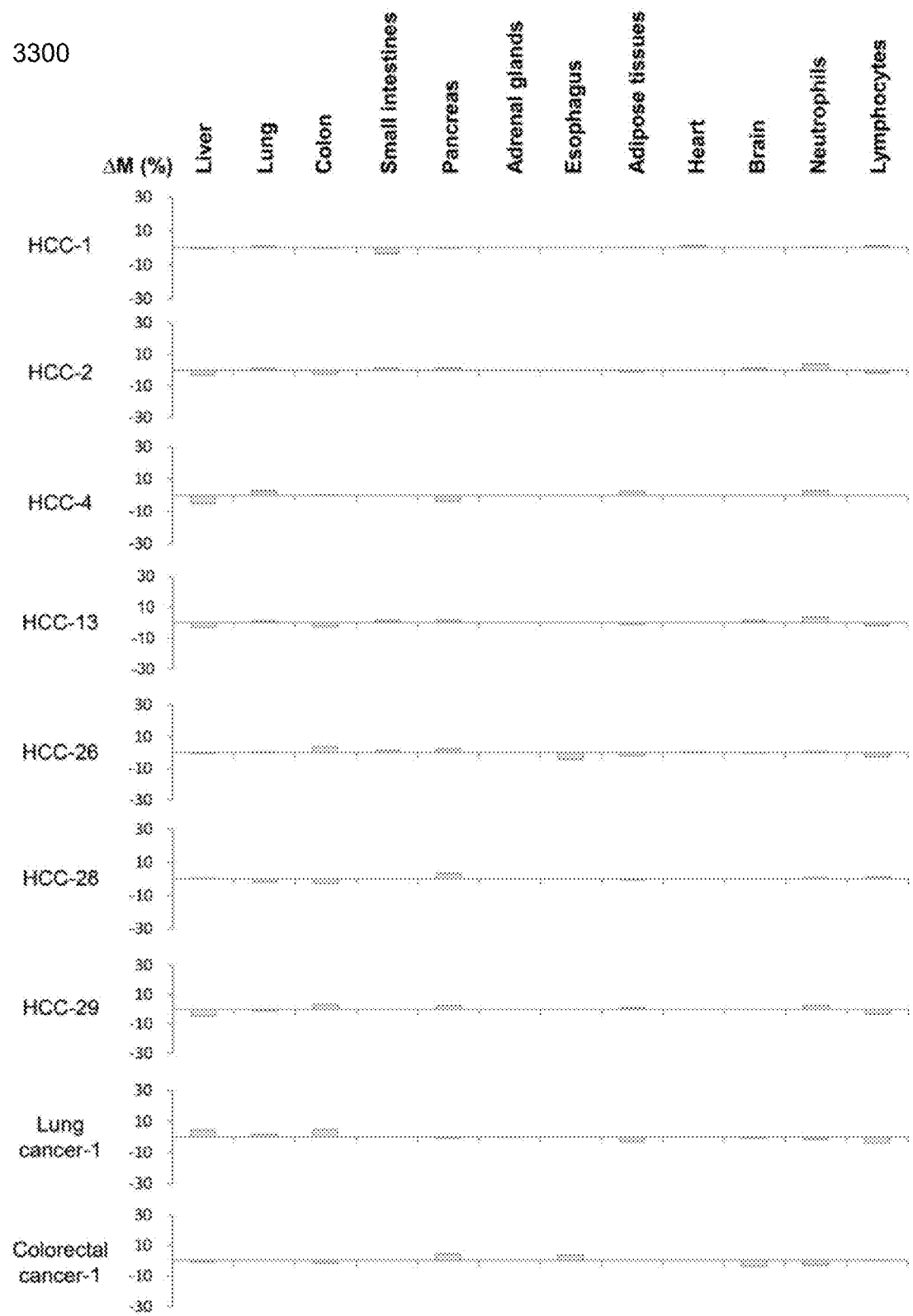
FIG. 33 is a diagram showing separation values ΔM between randomly chosen genomic regions across different tissues for the cancer patients according to embodiments of the present invention.

FIG. 33 is a diagram 3300 showing separation values ΔM between randomly chosen genomic regions across different tissues for the cancer patients according to embodiments of the present invention. As a control, we also performed the same analysis using two sets of randomly chosen genomic regions not exhibiting copy number aberrations in plasma. The ΔM values shown represent the difference in contributions of a particular tissue to plasma DNA between two sets of randomly selected regions without plasma DNA copy number aberrations. As can be seen in FIG. 33, for this control analysis, there is no systematic relationship between the ΔM values and the tissue of origin of the cancer.

3. Pregnant Woman with Lymphoma

In addition to the copy number aberrations, methylation deconvolution can also be applied for determining the tissue of origin of other types of genomic aberrations, for example, but not limited to single nucleotide mutations and translocations. The methylation status of the regions close to the genomic aberrations can be determined and compared with the methylation status of unaffected regions. The tissue of origin for the genomic aberrations is expected to show a higher contribution to plasma DNA at the affected region.

Figure 34A:
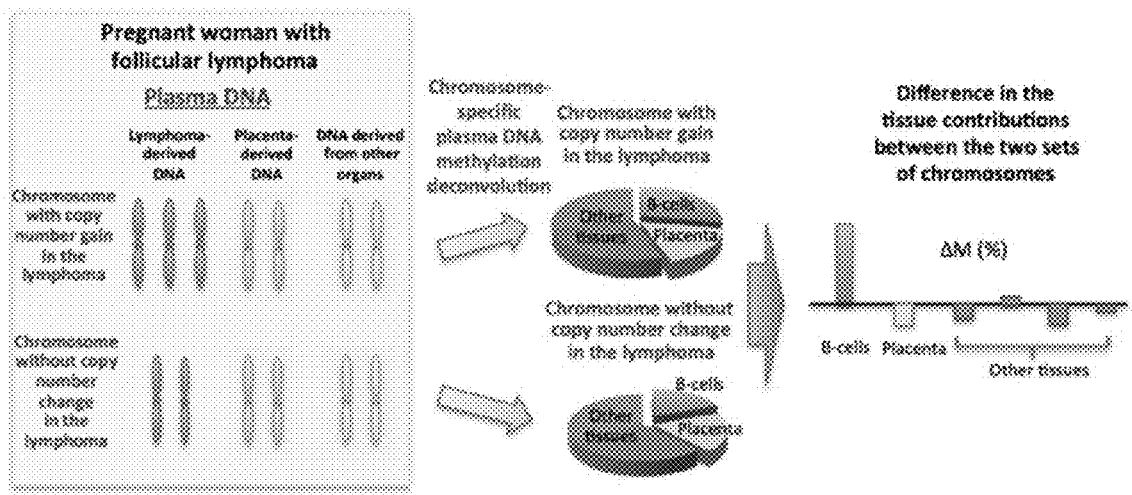
FIG. 34A shows an illustration of methylation deconvolution analysis for the pregnant woman with a concurrent lymphoma according to embodiments of the present invention.

FIG. 34A shows an illustration of methylation deconvolution analysis for the pregnant woman with a concurrent lymphoma according to embodiments of the present invention. FIG. 34A shows a region with copy number gain and a region without copy number gain. To confirm the tissue of origin of the observed copy number aberrations in plasma, plasma methylation deconvolution can be performed separately using markers present in the genomic regions showing amplifications in plasma (denoted as $M_{Tissue}^{Amp}$). and regions showing normal copy numbers (denoted as $M_{Tissue}^{Normal}$):

$$\Delta M_{Tissue} = M_{Tissue}^{Amp} - M_{Tissue}^{Normal}.$$

FIG. 34A shows a chart of fractional contributions for B-cells, placenta, and otherwise tissues. As the tissue of origin of the CNAs is the follicular lymphoma, the tissue type (B-cells) that the lymphoma arose from would give the highest value of ΔM.

To further illustrate the utility of embodiments, we analyzed the plasma DNA of a pregnant woman who was diagnosed as having a recurrent follicular lymphoma during early pregnancy. This woman had a history of follicular lymphoma and received curative-intent chemotherapy. She became pregnant subsequently while her lymphoma was in clinical remission. During the 11$^{th}$ week of gestation, a blood sample was collected from the pregnant woman for noninvasive prenatal testing of fetal chromosomal aneuploidies. The maternal plasma DNA sequencing results revealed gross abnormalities. Recurrence of the follicular lymphoma was confirmed by histological examination of lymph node and trephine biopsies.

Figure 34B:
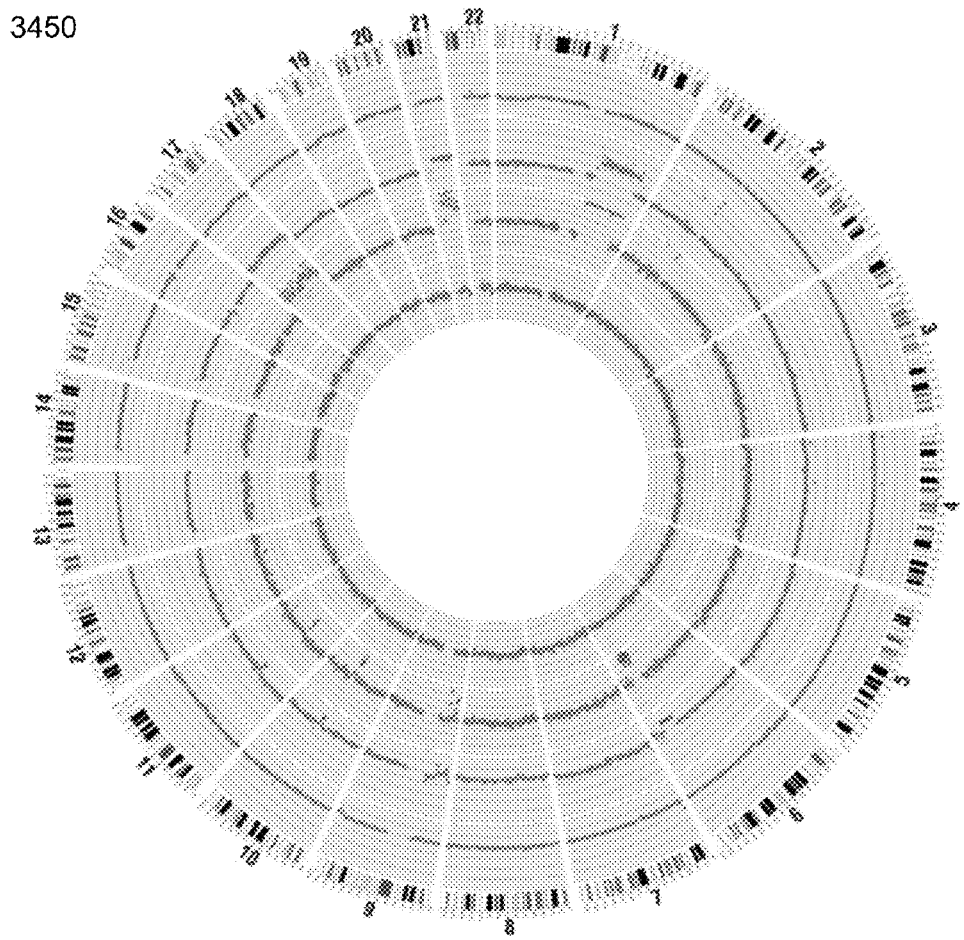
FIG. 34B is a plot showing genome-wide DNA sequencing analysis for copy number aberration detection among specimens collected from the pregnant woman who was diagnosed as having a recurrent follicular lymphoma during early pregnancy.

FIG. 34B is a plot 3450 showing genome-wide DNA sequencing analysis for copy number aberration detection among specimens collected from the pregnant woman who was diagnosed as having a recurrent follicular lymphoma during early pregnancy. Plot 3450 shows the genome-wide copy number analysis in the buffy coat, lymph node biopsy, pre-treatment plasma, as well as a plasma sample collected 10 weeks after the start of chemotherapy. From inside to outside: buffy coat of the pre-treatment plasma sample, lymph node biopsy, plasma sample collected before treatment and plasma sample collected after treatment. The chromosome ideogram is shown in clockwise manner at the outermost ring. Each dot represents a 1-Mb region. Green, red and grey dots represent regions with copy number gains, copy number losses and without copy number aberrations, respectively. The copy numbers are arranged in ascending order from the center to outside. Dots closer to the center compared with the other chromosomal regions indicate a copy number loss. Dots further deviated from the center compared with the other chromosomal regions indicate a copy number gain.

Copy number aberrations were detected in the lymph node biopsy and the pre-treatment plasma sample, but not in the post-treatment plasma sample and the buffy coat of the pre-treatment plasma sample. There was a high similarity between the profiles of copy number aberrations of the lymphoma and that in the pre-treatment plasma. The presence of copy number aberrations in the pre-treatment plasma portion, but absence of such aberrations in the blood cell portion of the same blood sample, suggest that the plasma DNA abnormalities were derived from the lymphoma-associated cell-free DNA rather than circulating tumor cells.

Genome-wide bisulfite sequencing followed by methylation deconvolution was performed on the pre-treatment plasma sample. In this patient, none of the contiguous regions exhibiting copy number losses in plasma were 30 Mb or above in size. As a result, the number of methylation markers located within the deleted regions was insufficient for tissue mapping analysis. Therefore, regions that did not exhibit any copy number aberrations were used as reference.

Figures 35A, 35B:
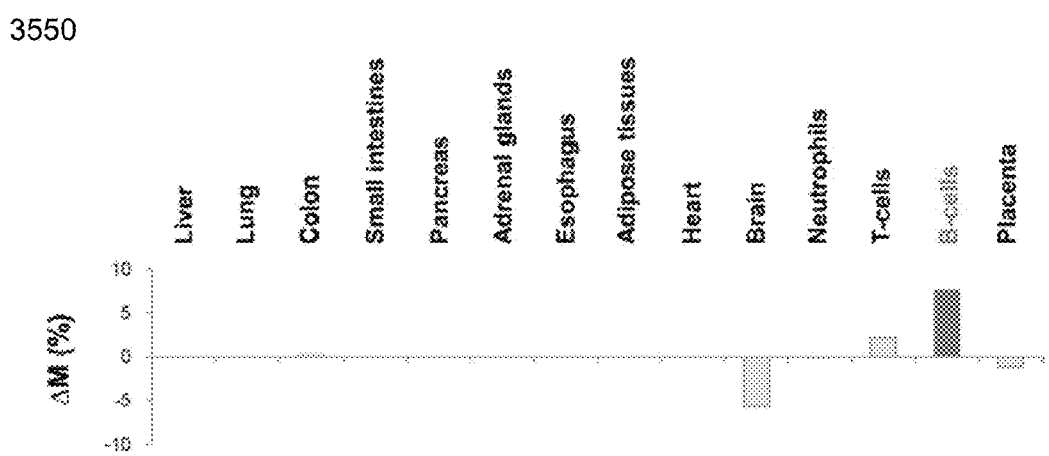
FIG. 35A is a table 3500 showing fractional contributions determined from plasma DNA tissue mapping on the pretreatment plasma sample for the pregnant woman with recurrent follicular lymphoma.
FIG. 35B is a diagram showing separation values of ΔM for different tissues for the pregnant woman with a concurrent follicular lymphoma.

FIG. 35A is a table 3500 showing fractional contributions determined from plasma DNA tissue mapping on the pre-treatment plasma sample for the pregnant woman with recurrent follicular lymphoma. The proportional contribution of plasma DNA from lymphocytes was 70.2%. Plasma DNA contribution of the B-lymphocytes was 62.2% and the T-lymphocytes contributed 8%.

FIG. 35B is a diagram 3550 showing separation values of ΔM for different tissues for the pregnant woman with a concurrent follicular lymphoma. ΔM values are shown across different tissues for the pre-treatment plasma sample of this patient. The B-cells show the highest ΔM value suggesting that the copy number aberrations were derived from B-cells. The follicular lymphoma cells are derived from the B-cells. As can be seen the B-lymphocytes show the highest ΔM value, thus confirming that they are the origin of the copy number aberrations in plasma.

4. Metastatic Lesions in Cancer Patients

Methylation deconvolution of these genomic aberrations can be particularly useful for the clinical scenarios where it is uncertain whether a tumor is a primary cancer of the affected organ or a metastatic lesion from a cancer of another organ. As illustrated above, the involvement of an organ by a tumor would lead to an alteration in the contribution of the affected organ to the plasma. In addition, the analysis of CNAs of plasma DNA by methylation deconvolution is useful to identify the tissue origin of the primary cancer. The combination of these two types of analyses can be useful for determining if a metastatic lesion is present.

To illustrate this, three hypothetical examples are discussed below:

i. a patient with HCC (a primary liver cancer);

ii. a patient with a primary colorectal cancer without liver metastasis; and iii. a patient with a primary colorectal cancer with liver metastasis.

TABLE 4

Expected results for plasma DNA methylation deconvolution analysis for the three hypothetical patients.

| | Contribution from the liver | Deconvolution of the CNAs in plasma |
|---|---|---|
| HCC patient | Increased | CNAs from the liver |
| Colorectal cancer patient without liver metastasis | Normal | CNAs from the colon |
| Colorectal cancer patient with liver metastasis | Increased | CNAs from the colon |

For the HCC patient, the presence of the tumor in the liver would lead to an increased contribution of the liver to the plasma DNA. In addition, as the cancer is derived from the liver cells, the tissue of origin of the CNAs associated with the cancer would be the liver. For the colorectal patient without liver metastasis, as the liver is not involved, the liver contribution to plasma DNA is expected to be normal; and the methylation deconvolution indicates that the tumor is derived from the colon. For the colorectal cancer patient with liver metastasis, the invasion of the liver by tumor cells would lead to an increase in the release of liver DNA into the plasma. As the cancer is derived from the colon, the CNA analysis would indicate the aberrations are originated from the colon.

As an example, a patient presented with a liver mass on ultrasonography study. On subsequent clinical investigation, the patient was found to have a colorectal cancer metastasizing to the liver. Methylation deconvolution was performed on the plasma. Table 5 shows this patient showed an increased contribution from the colon to the plasma DNA.

TABLE 5

Fractional contributions of patient with liver mass on ultrasonography study.

| Tissue | Contribution (%) |
|---|---|
| Liver | 2.5 |
| Lung | 6.2 |
| Colon | 20.0 |
| Small intestines | 0.0 |
| Pancreas | 0.0 |
| Adrenal glands | 0.0 |
| Esophagus | 0.4 |
| Adipose tissues | 4.7 |
| Heart | 0.0 |
| Brain | 0.0 |
| T-cells | 3.4 |
| B-cells | 14.2 |
| Neutrophils | 48.5 |

Figure 36A:
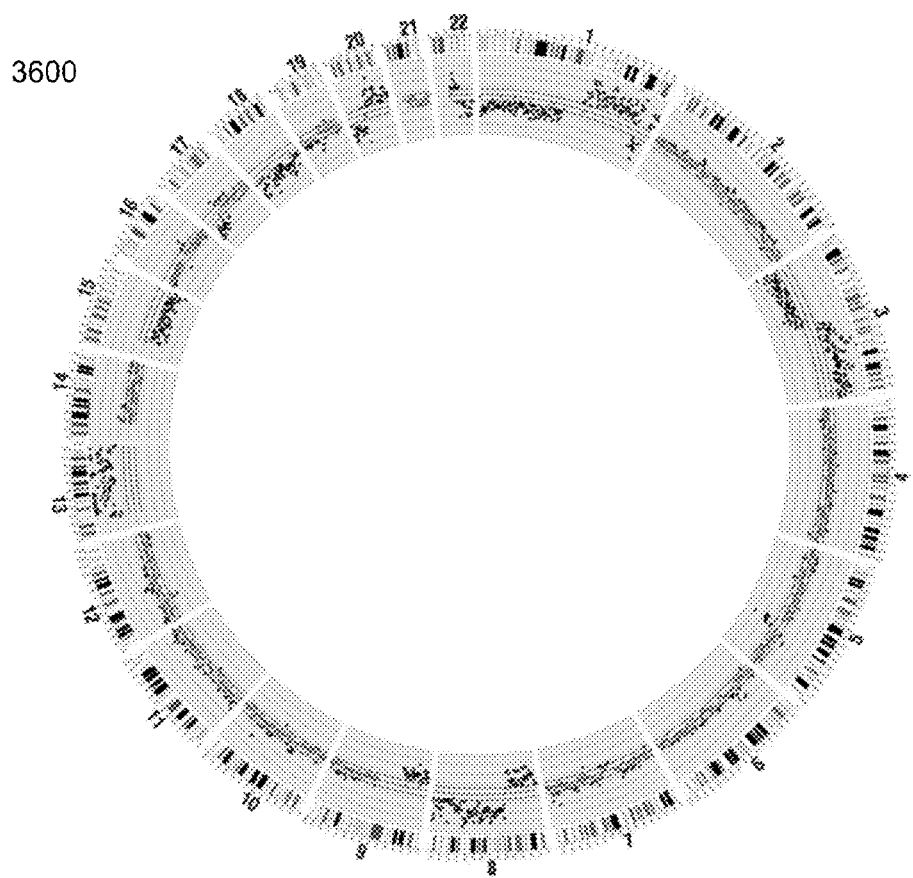
FIG. 36A is a plot showing copy number aberration analysis on plasma DNA for a patient with colorectal cancer metastasizing to the liver.

FIG. 36A is a plot 3600 showing copy number aberration analysis on plasma DNA for a patient with colorectal cancer metastasizing to the liver according to embodiments of the present invention. Each dot represents a 1-Mb region. The results are expressed as number of standard deviations from the mean genomic representation of plasma DNA for a group of 32 healthy control subjects. The grey dots lying between the two black lines indicate that there was no deviation in plasma DNA representation from the mean of the healthy subjects. The dark dots lying inside and outside of the regions between the two black lines indicate that those regions were under- and over-representation, respectively, in the patient's plasma DNA. The regions with over- and under-representation in plasma DNA were then analyzed using deconvolution analysis to determine the tissue of origin of the aberrations.

Figure 36B:
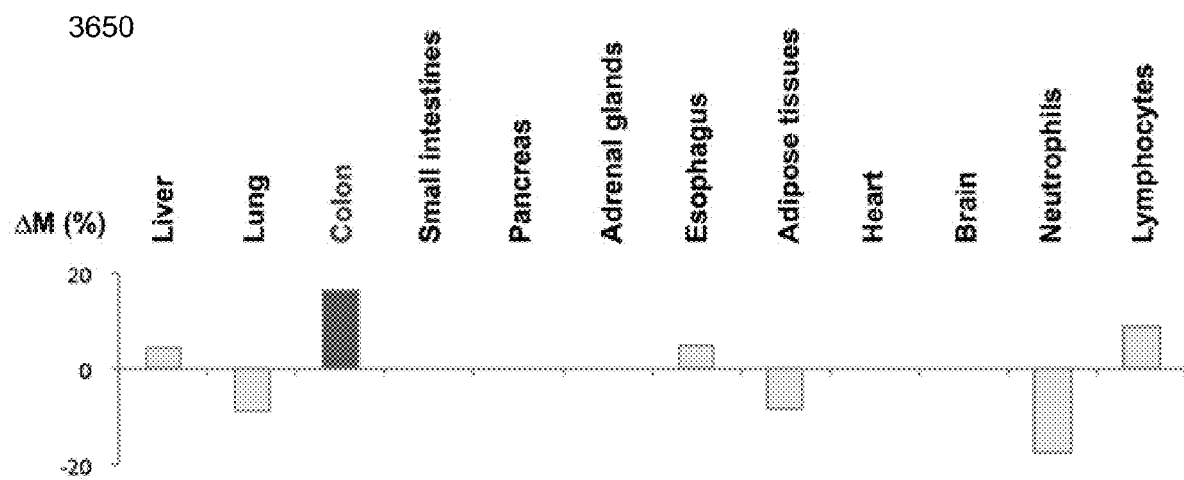
FIG. 36B is a diagram showing the methylation deconvolution analysis of the copy number aberrations of the plasma DNA for the patient with colorectal cancer and liver metastasis according to embodiments of the present invention.

FIG. 36B is a diagram 3650 showing the methylation deconvolution analysis of the copy number aberrations of the plasma DNA for the patient with colorectal cancer and liver metastasis according to embodiments of the present invention. The analysis indicates that the difference between amplified and deleted regions (ΔM) was biggest for the colon suggesting that the aberrations were most likely derived from the colon. Therefore, embodiments were able to identify the primary cancer that resulted in the liver mass.

5. Somatic Mosaicism

Somatic mosaicism describes the presence of cells with different genomic constitutions in certain tissues of the body. This arises from errors occurring during chromosome segregation or DNA replication, leading to a variety of genomic aberrations, such as chromosome aneuploidy, copy number variations (CNVs), genomic rearrangements, single-nucleotide variations, or repeat expansions and microsatellite instabilities (Lupski. Science 2013; 341: 358-9).

Embodiments of plasma DNA methylation deconvolution can be useful for identifying the tissue affected by somatic mosaicism. The plasma DNA would first be analyzed to characterize the genomic aberration, for example, a CNA. Then, methylation deconvolution can be performed using methylation markers within the affected region and another region not affected. By comparing the compositions of plasma DNA from these two sets of regions, the ΔM can be determined. The tissue affected by the somatic mosaicism can then be identified by tissue having significant separation values (e.g., ΔM values).

6. Detection and Monitoring of Various Pathological Conditions

Plasma DNA methylation convolution can be used for the detection and monitoring of various pathological conditions, for example but not limited to stroke, myocardial infarction, autoimmune disease and infections. For example, a patient is admitted for loss of consciousness and a clinical diagnosis of stroke is suspected. The elevation of the contribution of the brain can be useful for indicating the presence of significant damage to the brain. The elevation of the contribution of the brain to plasma DNA can be concluded by comparing the patient's results to those of healthy control subjects. The levels of the elevation of the contribution can also be used to indicate the prognosis of the patient.

Similarly, for patients suspected of having myocardial infarction or other heart diseases because of clinical symptoms, the contribution from the heart can be used to indicate the diagnosis or to predict the prognosis of the patient. The cutoffs can be determined using the values of the contribution of the heart to plasma DNA in a group of healthy control subjects.

In one embodiment, a cutoff can be a certain percentile of the brain contribution of the healthy control subjects, for example $90^{th}$, $95^{th}$ or $99^{th}$ percentile. In another embodiment, a cutoff can be set as 2 SD, 2.5 SD, 3 SD or 3.5 SD above the mean value of the control subjects.

Plasma DNA methylation deconvolution can also be applied for identifying the source of infection for patients presenting with sepsis of unknown origin. The infected tissue is expected to release more DNA into the plasma because of increased cellular damage.

7. Summary

As detailed above, embodiments have been validated for the detection of the plasma contribution of (i) the placenta using pregnant women, (ii) the liver using HCC patients and subjects following liver transplantation, (iii) white blood cells using bone marrow transplantation recipients and the lymphoma case diagnosed during pregnancy, (iv) the lungs from the lung cancer cases, and (v) the colon from the colorectal cancer case. As plasma DNA has generally been regarded as a marker of cell death, our approach can be used as a general method for assessing cell death phenomena in different tissue types. Hence, in addition to applications to prenatal testing, cancer detection/monitoring and transplantation monitoring, embodiments can also have applications in many branches of medicine for studying cell death or injury of various bodily tissues, e.g. stroke, myocardial infarction, trauma, autoimmune disorders, infectious diseases, etc.

Further, the data show that characteristic perturbations of the tissue composition of the plasma DNA pool would be observed in accordance with the physiological state or underlying pathology of the patient. The ability to identify the tissue of origin of copy number aberrations that can be observed in plasma has numerous potential clinical applications. For example, for the use of plasma DNA sequencing for screening for cancer, embodiment can identify the likely tissue of origin of the cancer, for planning further diagnostic investigations or therapeutic procedures. As another example, embodiments would be very useful for noninvasive prenatal testing. Using the detection of trisomy 21 as a model system, we have demonstrated that one can identify the placenta as the tissue of origin of the excess amount of chromosome 21 in the maternal plasma.

The applications for cancer detection and noninvasive prenatal testing converge in the case of the pregnant woman who suffered from follicular lymphoma. We observed copy number aberrations in the plasma of this pregnant woman (FIG. 34A). Plasma methylation deconvolution revealed a very high contribution from lymphocytes into plasma. The B-lymphocyte is the cell type involved in the pathology of follicular lymphoma. Thus, it was interesting that embodiments identified the B-cells (62.2%, FIG. 35A), rather than the T-cells, as the major contributor of plasma DNA in the patient.

The ΔM analysis comparing the methylation deconvolution results obtained using methylation markers originating from the genomic regions showing increased copy number aberrations versus those showing normal copy numbers further confirmed the B-cells as the source of the copy number aberrations (FIG. 35B). These results are thus entirely consistent with the diagnosis of follicular lymphoma. With the increase in the clinical utility of noninvasive prenatal testing and the trend of further advances in maternal age, it is likely that more and more cases of malignancy will be detected during the course of such testing (Osborne C M, et al. (2013) *Prenat Diagn* 33(6): 609-611; Vandenberghe P, et al. (2015) *Lancet Haematol* 2:e55-e65). Embodiments described herein would therefore be very useful in the further investigation of such cases.

In some embodiments, the selection of methylation markers that would be used for the deconvolution process can be further refined. In one variation, the marker set can be adjusted to focus more on the tissue types that are the less prominent contributors to the plasma DNA pool. This can uncover new pathophysiological status that one can monitor using embodiments.

In addition to the use of DNA methylation markers, embodiments can also investigate the tissue contribution towards the circulating nucleic acids pool through the study of mRNA (Ng E K O, et al. (2003) Proc Natl Acad Sci USA 100:4748-4753; Tsui N B Y, et al. (2014) Clin Chem 60(7):954-962; Koh W, et al. (2014) Proc Natl Acad Sci USA 111(20):7361-7366) and microRNA (Chim S S C, et al. (2008) Clin Chem 54(3):482-490; Wang K, et al. (2009)

Proc Natl Acad Sci USA 106(11):4402-4407). The DNA methylation and transcriptomic approaches can be synergistic to one another and would give different types of information.

In the examples above, DNA libraries were prepared following manufacturer's instructions (Illumina) and sequenced on a HiSeq or NextSeq system (Illumina). For HiSeq, 76 (single-end mode) or 76×2 (paired-end mode) cycles of sequencing were performed with the TruSeq SBS Kit v3 (Illumina). For NextSeq, 76×2 paired-end sequencing cycles were performed using the NextSeq 500 High Output v2 Kit (Illumina). After base calling, adapter sequences and low quality bases (i.e. quality score<5) were removed. The trimmed reads in FASTQ format were then processed by the methylation data analysis pipeline Methy-Pipe. The basic sequencing parameters, including the sequencing depth, of all the samples are summarized in table 3700 of FIGS. 37 and 38.

D. Method for Determining Sequence Imbalance

Figure 39:
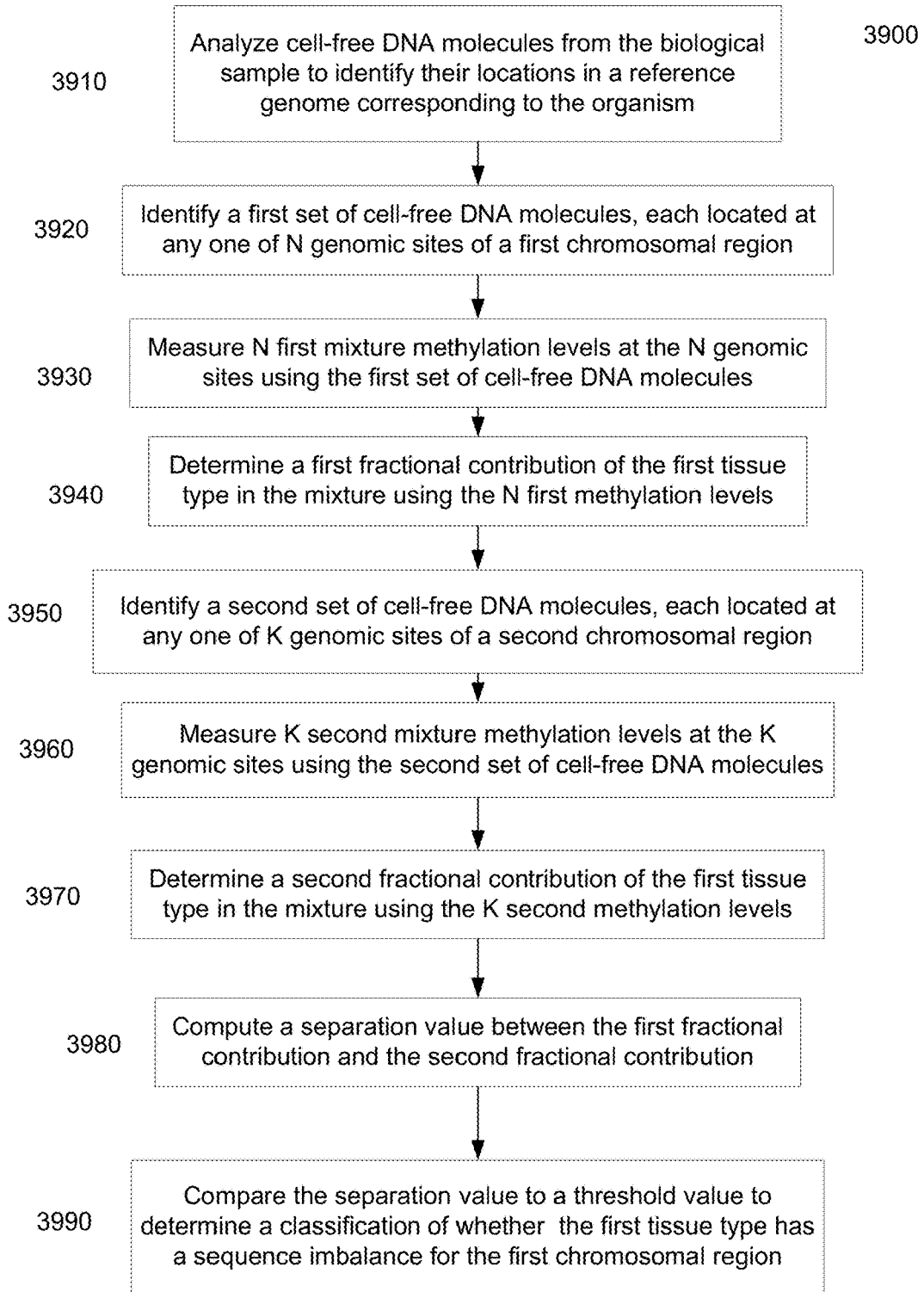
FIG. 39 is a flowchart illustrating a method of analyzing a biological sample of an organism to determine whether a chromosomal region exhibits a sequence imbalance using methylation deconvolution according to embodiments of the present invention.

FIG. 39 is a flowchart illustrating a method 3900 of analyzing a biological sample of an organism to determine whether a chromosomal region exhibits a sequence imbalance using methylation deconvolution according to embodiments of the present invention. The biological sample includes a mixture of cell-free DNA molecules from a plurality of tissues types, including a first tissue type. Method 3900 is performed at least partially using a computer system.

At block 3910, a plurality of cell-free DNA molecules from the biological sample are analyzed. Block 3910 can be performed in a similar manner as block 140 of method 100 of FIG. 1.

For example, at least 1,000 cell-free DNA molecules can be analyzed to determine where the cell-free DNA molecules are located, and methylation levels can be measured as described below.

At block 3920, a first set of the plurality of cell-free DNA molecules is identified. Each of the DNA molecules of the first set are located at any one of N genomic sites of a first chromosomal region of the reference genome corresponding to the organism. For example, one DNA molecule can be located at (e.g., having a sequence read aligned to) a first of the N genomic sites, and another DNA molecule can be located at a second of the N genomic sites. Both, DNA molecules would be included in the first set.

The N genomic sites can be identified in various ways and using various criteria. Techniques described in section II may be used. The N genomic sites can satisfy certain criteria, such as methylation levels across tissues and across individuals. The genomic sites may be identified based on data from other samples, e.g., methylation analyses from databases. N is an integer, which may be greater than or equal to 10.

The N genomic sites would be within the first chromosomal region, which may be contiguous or composed of non-contiguous subregions. The first chromosomal region can be selected based on a CNA analysis, e.g., as described above. For instance, a region can be identified as having an over-representation or under-representation of DNA molecules relative to other regions, where the analysis can potentially use the same biological sample as used for the methylation analysis. The over or under-representation suggests a copy number aberration, and the methylation analysis below can determine which tissue is an origin of the CNA.

At block 3930, N first mixture methylation levels are measured at the N genomic sites using the first set of the plurality of cell-free DNA molecules. One first mixture methylation level can be measured for each of the N genomic sites. Block 3930 can be performed in a similar manner as block 150 of method 100 of FIG. 1. Thus, any technique for measuring a methylation level of a DNA molecule may be used. In some embodiments, the measurement of the methylation level of a DNA molecule can use methylation-aware sequencing results, which may also be used to determine the location of the DNA molecule.

At block 3940, a first fractional contribution of the first tissue type in the mixture is determined using the N first methylation levels. In some embodiments, block 3940 can be performed via blocks 160 and 170 of method 100 of FIG. 1. Thus, a fractional contribution can be determined simultaneously for a panel of M tissue types.

Block 3940 may use N issue-specific methylation levels at N genomic sites, determined for each of M tissue types, e.g., as in block 120 of method 100 of FIG. 1. In some embodiments, the N tissue-specific methylation levels may just be for the first tissue type and collectively for all other tissue types. Thus, M may effectively just be 2. If the first tissue type is the only tissue type of interest, such a generalization does not lose any information. The collective value for the other tissue types may be generated from the separate values for each of the other tissue types.

At block 3950, a second set of the plurality of cell-free DNA molecules are identified. Each of the DNA molecules of the second set are located at any one of K genomic sites of a second chromosomal region of the reference genome corresponding to the organism. The second chromosomal region is different than the first chromosomal region (e.g., different chromosomes), and thus the K genomic sites are different than the N genomic sites. K is an integer, which may be greater than or equal to 10. The values of K and N can also be different, and thus K may not equal N. Block 3950 may be performed in a similar manner as block 3920.

The second chromosomal region can be identified as a region not exhibiting any aberration. The identification may be based on a measurement of a sample from the organism, e.g., in a similar manner as the first chromosomal region was identified, but not showing any over or under-representation. In other embodiments, the second chromosomal region can be identified as having an opposite aberration from the first chromosomal region, where the aberrations can be assumed to come from the same tissue type.

In yet other embodiments, the second chromosomal region may be identified based on typical locations of aberrations or lack thereof. For the example of a fetus, aneuploidies are relatively more common to occur for chromosomes 13, 18, and 21, but relatively uncommon for the other chromosomes. Thus, one or more of the other chromosomes may be used as the second chromosomal region. The second chromosomal region may be contiguous or contiguous or composed of non-contiguous subregions.

At block 3960, K second mixture methylation levels are measured at the K genomic sites using the second set of the plurality of cell-free DNA molecules. One second mixture methylation level can be measured for each of the K genomic sites. Block 3960 can be performed in a similar manner as block 3930.

At block 3970, a second fractional contribution of the first tissue type in the mixture is determined using the K second methylation levels. Block 3970 can be performed in a similar manner as block 3940.

At block 3980, a first separation value between the first fractional contribution and the second fractional contribution is computed. As examples, a separation value can include a difference or a ratio of the first fractional contribution and the second fractional contribution. The separation value can include other factors, e.g., multiplicative factors. As other examples, a difference of functions of the fractional contributions can be used, e.g., a difference of the natural logarithms (ln) of the fractional contributions.

At block 3990, the first separation value is compared to a threshold value to determine a classification of whether the first tissue type has a sequence imbalance for the first chromosomal region. The classification can be that the first tissue type has a sequence imbalance for the first chromosomal region when the separation value exceeds the threshold value. As described in the previous sections, a large separation value indicates that a sequence imbalance (e.g., a copy number aberration) exists for the first tissue type. As an example, if the first fractional contribution is larger than the second fractional contribution by the threshold value, it can be determined that the first chromosomal region exhibits an amplification in the first tissue type. If the first fractional contribution is smaller than the second fractional contribution by the threshold value, it can be determined that the first chromosomal region exhibits a deletion in the first tissue type.

In one example, the organism is pregnant with a fetus, and the first tissue type is placental tissue, as for section V.C.1. Thus, the method can detect whether fetus has an aneuploidy in the first chromosomal region. In another example, the first tissue type may not be placental tissue, even when the organism is pregnant. Such a test can determine whether other tissues have a sequence imbalance, e.g., as in section V.C.3.

As mentioned above, the first chromosomal region can be identified as exhibiting a copy number aberration based on an amount of cell-free DNA molecules that are located in the first chromosomal region. An over or under-representation of the amount relative to another region (e.g., by at least a threshold) can indicate a copy number aberration. As examples, the amount of cell-free DNA molecules that are located in the first chromosomal region can be a raw count of cell-free DNA molecules, an accumulated length of cell-free DNA molecules, and a density, which may be determined as a count per unit length in of the region.

Once a region is identified for testing, separation values can be determined for M tissue types. Thus, for each of the first and second chromosomal regions, M fractional contributions can be determine for each of the M tissue types. Each of the separation values can be compared to a threshold to determine whether a tissue type is an origin. The separation values may indicate more than one tissue type exhibits the sequence imbalance, as in V.C.4. In one embodiment, the largest separation value can be identified as being the primary cancer.

If the organism is identified as having a sequence imbalance for the first chromosomal region in certain tissue (e.g., not placental tissue), then the organism can be classified as having a certain level of cancer for the certain tissue. The level of cancer can be determined based on the extent of the separation value. The level of cancer can be further determined based on a level of over-representation or under-representation for the first chromosomal region, as well as the number of chromosomal regions that exhibit an aberration.

In some embodiments, multiple regions can be tested for a sequence imbalance in the first tissue type. If many regions (e.g., more than a cutoff value) exhibit a sequence imbalance for the first tissue type, then the identification of the first tissue type as the origin can have greater statistical accuracy. And, if many regions are tested, the threshold for determining a sequence imbalance can be reduced, with a cutoff of a number of regions having a sequence imbalance being used to improve the specificity. Thus, the classification of whether the first tissue type has the sequence imbalance for the first chromosomal region can be based on the number of the different chromosomal regions having a corresponding separation value that exceeds the threshold value. In this manner, sensitivity can be increased by identifying regions having a small separation value (which otherwise may have not been detected). The threshold value can be dependent on the cutoff value, with a lower threshold value for a higher cutoff value, and vice versa.

Once an organism is diagnosed with a certain level of cancer, the organism can be treated based on the diagnosis. Treatment can also be performed for other methods that classify a diseased state. As examples, treatment can include surgery, radiotherapy, or chemotherapy.

VI. Targeted Analysis

The deconvolution of tissue contribution based on methylation analysis can involve the determination of the methylation status of CpG sites. In addition to using non-targeted bisulfite sequencing to determine the genome-wide methylation profile of the DNA mixture (e.g., plasma DNA), a targeted approach can also be used to study the methylation status or methylation densities of CpG sites of interest, or other methylation levels. The targeting of the CpG sites of interest can be performed, for example, but not limited to, DNA hybridization, microarray, PCR amplification and methylation-specific PCR. Combinations of these techniques can also be used. The targeted approach can increase the methylation information regarding individual CpG sites without substantially increase the amount of overall sequencing. The targeted approach can also increase the sensitivity and/or specificity and/or precision for detection the DNA contribution from a tissue into a bodily fluid, especially from one that is a minor contributor when compared with one or more other tissues.

In one example, the regions of interest can be enriched by hybridization, for example, but not limited to using the Nimblegen SeqCap system or the Agilent SureSelect Target Enrichment system. In another example, hybridization probes can be designed to capture specifically bisulfite converted DNA sequences. The sequencing libraries enriched for the regions of interest can then be sequenced. Using this strategy, the sequencing depth of the regions of interest can be significantly increased with the same number of DNA molecules sequenced from the sample compared with the non-targeted sequencing approach.

As another example, the regions of interest can be targeted using PCR amplification. PCR primers can be designed to amplify regions with CpG sites that are informative for the methylation deconvolution analysis. The amplified regions can be analyzed, for example, but not limited to using massively parallel sequencing, including single molecule sequencing (such as nanopore sequencing or the Pacific Biosciences Single Molecule Real-Time system), real-time PCR, digital PCR or mass spectrometry, for the overall methylation levels.

In one implementation, the PCR primers can be designed to target either the methylated sequences or the unmethylated sequences. In this implementation, the amounts of DNA molecules that are methylated and unmethylated can be compared so as to determine the methylation levels of the informative CpG sites (type I or type II methylation markers). In another implementation, the PCR primers only hybridize to regions without differential methylation, for example, a region without a CpG site. In this case, both methylated and unmethylated sequences can be amplified. However, the amplified amplicon would contain CpG sites and the methylation status of each amplified molecule can then be determined, for example, but not limited to using fluorescent probes that are specific to either the methylated or the unmethylated sequences. Alternatively, the PCR products can be analyzed using massively parallel sequencing or mass spectrometry.

Various embodiments can also be applied for analyzing the methylation profiles of different CpG sites so as to maximize the cost-effectiveness of the analysis.

A. Targeted for Both Type I and Type II Markers

Targeting both type I and type II markers is useful for increasing the overall cost-effectiveness of the methylation deconvolution analysis, as a large amount analyzed cell-free DNA molecules would correspond to the genomic sites being used. In other words, to get the same number of informative DNA molecules for methylation deconvolution analysis, the amount of sequencing using the targeted approach can be substantially reduced compared with using the genome-wide analysis.

B. Targeted for Type I Markers and Genome-Wide of Type II Markers

Targeting type I markers and a genome-wide analysis of Type II markers is particularly useful when the contribution of a specific-type of tissue needs to be determined more precisely and the contributions of other tissues are of interest in general. Targeting both type I and type II markers can also achieve this, but designing the assays to target both types of markers can require a lot of efforts.

In this situation, the type I markers that are differentially methylated in the tissue of interest can be analyzed in a targeted manner so that their methylation levels in the DNA mixture, e.g. plasma DNA and urinary DNA, can be more precisely determined. In some examples, the tissues targeted by the type I markers are minor contributors to the plasma DNA pool. Targeting such tissues using type I markers would increase the sensitivity that one can detect and measure their contributions to the plasma DNA pool. Another advantage is that one can tune the concentration range that such measurements would be optimized for.

As an illustration, if one wishes to target a tissue A that normally contributes a very low level of DNA into the plasma, one can use multiple type I markers to target tissue A, e.g., using 10 or 100 markers. One can make further adjustment of the measured contribution of tissue A to plasma if only a fraction of the 10 or 100 markers, respectively, would be positive for a particular plasma sample. When the contribution of tissue A to the plasma is very low, the probability of detecting markers that are specific for tissue A in plasma would be low and the detection rate is governed by one or more statistical functions, for example the Poisson distribution. In this case, the relative contribution of tissue A to plasma DNA can be deduced by the percentage of type I markers that are detectable in the plasma. The contributions of other tissues can be determined using type II markers.

C. Targeted for Type II Markers and Genome-Wide of Type I Markers

Targeting type II markers and a genome-wide analysis of Type I markers may be useful to exclude the contribution of a particular tissue type. For example, the contribution of the placenta is expected to drop to undetectable level after delivery. The targeted analysis of type II markers and genome-wide analysis of type I markers that are specific for the placenta can be useful to determine accurately the contributions of different tissue organs and to exclude the contribution of the placenta to the plasma DNA. This may be useful to exclude the retaining of gestational product in a previously pregnant woman.

VII. Methylation Deconvolution of Different Cell-Free Fluids

A. Urine DNA

DNA methylation deconvolution can also be performed on urine DNA. Previous studies have demonstrated that cell-free DNA can be detected in the urine of healthy subjects and patients with a wide variety of diseases (Hung et al. Clin Chem. 2009; 55:715-22; Chan et al. Clin Cancer Res. 2008; 14:4809-13; Garcia Moreira et al. Clin Biochem. 2009; 42:729-31; Hoque et al. J Natl Cancer Inst. 2006; 98:996-1004). The cell-free DNA in the urine can be derived locally from the cells in the renal and urinary system (Hogue et al. J Natl Cancer Inst. 2006; 98:996-1004) or derived transrenally from the blood plasma (Hung et al. Clin Chem. 2009; 55:715-22; Chan et al. Clin Cancer Res. 2008; 14: 4809-13). Methylation deconvolution analysis can be useful for the identification of local and systemic diseases.

In one embodiment, methylation deconvolution of urine DNA can be used for the monitoring of patients who had received renal transplantation. It was previously shown that increased DNA would be released from the grafted kidney into urine in renal transplant recipient in the presence of graft rejection (Zhong et al. Ann N Y Acad Sci. 2001; 945:250-7). Thus, the elevation of the percentage contribution of the kidney in the urine DNA would be useful to indicate the presence of renal rejection.

In another embodiment, the presence of malignancies in the urinary tract can be detected or monitored using urine DNA deconvolution. The tissue of origin of the cancer can be indicated with the increase in contribution to the urine DNA. For example, patients with bladder and prostate cancer would be expected to have an elevated contribution from the bladder and the prostate, respectively. One can also performed methylation deconvolution in conjunction with genomic aberrations (e.g. copy number aberrations and single nucleotide variants) to locate the tissue of origin of the genomic aberrations.

Other clinical scenarios, such as infection and trauma can also be detected through the deconvolution of urine DNA. In the case of infection, one would see increased concentrations from the leukocyte populations to the urine DNA following methylation deconvolution.

One can also apply urine DNA methylation deconvolution for detecting and monitoring disorders of the kidney. For example, the technology can be applied to detect and monitor kidney disease with an autoimmune origin. In one embodiment, one would see aberrant contributions from selected leukocyte populations (e.g. from the lymphocytes) into the urine DNA pool. Examples of autoimmune related kidney disorders include the IgA nephropathy and glomerulonephritis due to systemic lupus erythematosus.

As another example, the technology can be applied to detect and monitor kidney disease in which there is damage to the glomerular filtration barrier. In such cases, one would expect an increase in the transrenal component of urine DNA. In yet another embodiment, one can use urine DNA methylation deconvolution to detect malignancies of the kidney, e.g. renal cell cancer and transitional cell carcinoma of the renal pelvis. In this scenario, one can also perform methylation deconvolution in conjunction with genomic aberrations (e.g. copy number aberrations and single nucleotide variants) to locate the tissue of origin of the genomic aberrations.

Urine samples were collected from two pregnant women who were at the third trimester of pregnancy. For each urine sample, DNA was extracted from 17 mL urine using the Wizard Plus Minipreps DNA Purification System (Promega) as previously described (Tsui et al. PLoS One 2012; 7:e48319). DNA sequencing libraries were prepared with the KAPA DNA library preparation Kit (Kapa Biosystems). The urine DNA sequencing libraries were then subjected to 2 rounds of bisulfite modification using an EpiTect Bisulfite Kit (Qiagen). The adapter-ligated DNA molecules were enriched by 10 PCR cycles. Bisulfite-treated DNA libraries were sequenced for 75 bp in a paired-end format on HiSeq 2000 instruments (Illumina). The sequenced reads were aligned to the human reference genome (hg19). Deconvolution analysis based on the methylation level of the 1013 type I and 5820 type II markers was performed to determine the contribution of the different organs to the urine DNA.

TABLE 6

Fractional contributions determined from a urine sample.

| | Case 1 | Case 2 |
|---|---|---|
| Liver | 6.6 | 7.3 |
| Lung | 14.2 | 16.9 |
| Colon | 8.5 | 6.0 |
| Small intestines | 3.3 | 1.3 |
| Pancreas | 15.8 | 12.6 |
| Bladder | 12.2 | 8.5 |
| Adrenal glands | 1.6 | 0.0 |
| Esophagus | 17.8 | 8.1 |
| Adipose tissues | 0.0 | 1.8 |
| Heart | 0.0 | 0.0 |
| Brain | 8.4 | 6.5 |
| T cells | 0.0 | 0.0 |
| B cells | 0.0 | 6.6 |
| Neutrophils | 7.4 | 19.3 |
| Placenta | 4.3 | 5.0 |

Table 6 shows a percentage contributions of the different organs to the urine of the two pregnant women. 4.3% and 5% of the urine DNA was deduced to be from the placenta. This is consistent with the previous findings that fetal DNA can be transrenally passed into the urine of pregnant women (Tsui et al. PLoS One 2012; 7:e48319). In addition, the bladder has also contributed 12.2% and 8.1% of the total DNA in the two urine samples.

The size of each urine DNA molecule can be deduced from the genomic coordinates of the outermost nucleotides.

Figure 40A:
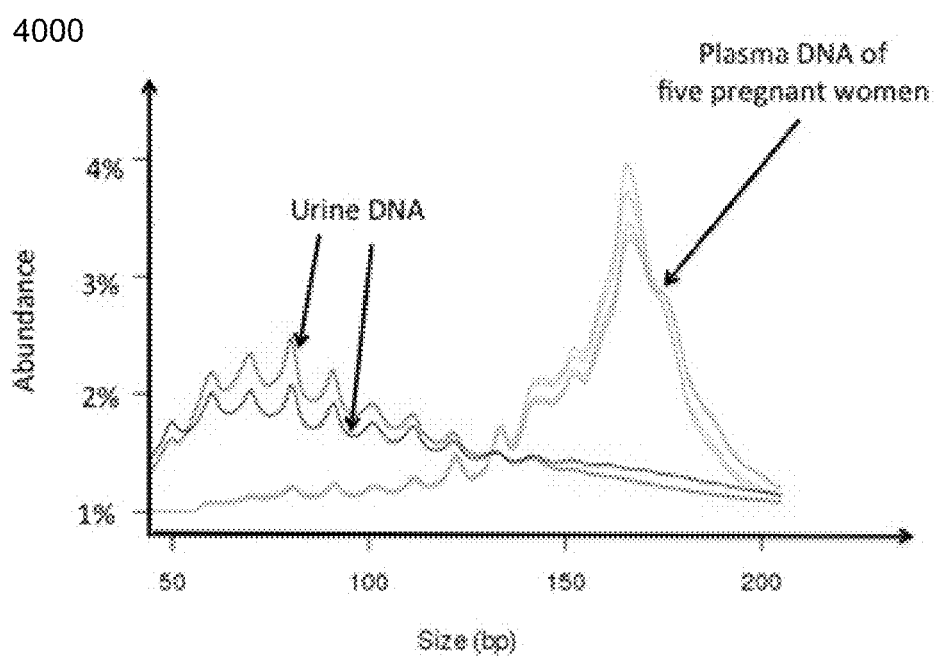
FIG. 40A is a plot showing size distributions of the urine DNA of the two pregnant women according to embodiments of the present invention.

FIG. 40A is a plot 4000 showing size distributions of the urine DNA of the two pregnant women according to embodiments of the present invention. As comparison, the size distributions of the plasma DNA of five pregnant women are also shown. The size distributions of the urine DNA were significantly shorter than that of the plasma DNA. These findings indicate that methylation deconvolution on the short urine DNA is feasible.

Figure 40B:
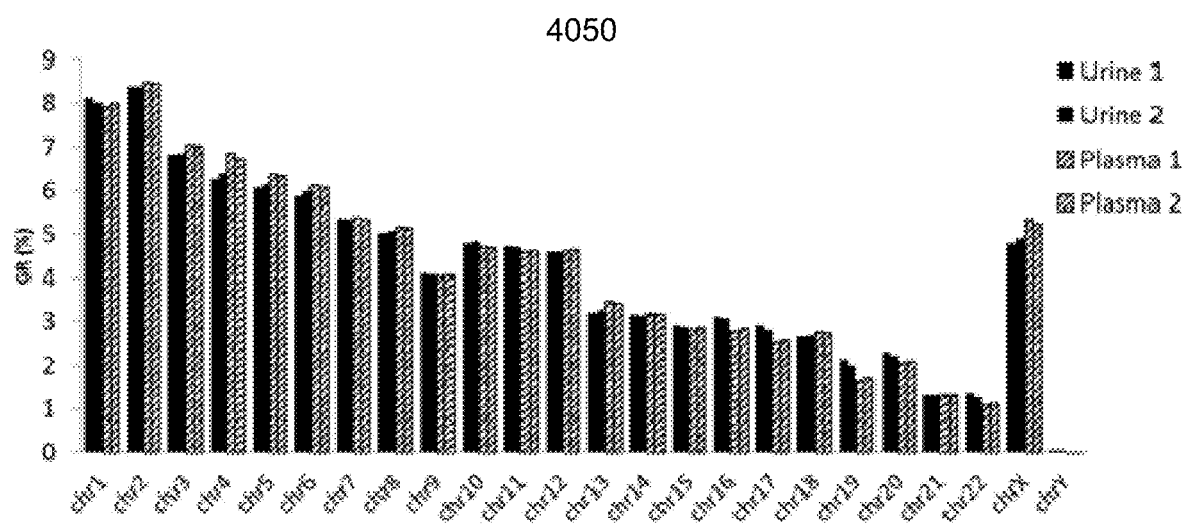
FIG. 40B shows a graph of the genomic representation (GR) of different chromosomes in the urine DNA according to embodiments of the present invention.

FIG. 40B shows a graph 4050 of the genomic representation (GR) of different chromosomes in the urine DNA according to embodiments of the present invention. As comparison, the genomic representations of the chromosomes of the plasma DNA samples from the two pregnant women are also shown. The proportional representations of different chromosomes were similar between urine DNA and plasma DNA samples. 0.063% and 0.059% of the urine DNA sequences aligned to the chromosome Y. This is compatible with the fact that both pregnant women were carrying male fetuses.

B. Cerebrospinal Fluid (CSF)

As another example, methylation deconvolution can also be performed on DNA extracted from CSF. Increased tissue destruction can be associated with different intracranial pathology, for example, cerebrovascular disease, infections, cancers, autoimmune disorders (e.g. multiple sclerosis) and degenerative disorders (e.g. Alzheimer's disease, Parkinson's disease, etc. The increased contribution of a specific cell type to the DNA of the CSF would be associated with the increased cell turnover of that particular cell type and can be used for the detection and monitoring (including response to treatment) of various disease.

C. Pleural Fluid and Ascitic Fluid

In a further example, methylation deconvolution can also be performed on DNA extracted from pleural fluid. Pleural effusion is commonly observed in patients suffering from various pulmonary pathologies. Pleural effusion is also observed in patients with heart failure, kidney diseases and those with liver diseases. In a previous study, it was shown that the measurement of DNA concentration in pleural fluid in patients with pleural effusion is useful to classify the pleural effusion into transudative and exudative (Chan et al. Clin Chem. 2003; 49:740-5). This classification is useful to indicate the possible pathologies the patient is suffering. The deconvolution of pleural fluid DNA would be useful to indicate the tissue origin of the pathology. For example, in patients suffering from malignant pleural effusion, the deconvolution of the pleural fluid can indicate whether the pleural effusion is due to a primary lung cancer or a metastatic cancer from another organ to the lung. In addition, methylation deconvolution can be performed on the regions exhibiting various types of genetic aberrations, including copy number aberrations and point mutations, so that the tissue origin of the aberrations can be determined.

In yet another example, methylation deconvolution can be performed on the DNA extracted from ascitic fluid. Ascites can be observed in various pathologies, for example liver cirrhosis, infection and malignancies. It can also be observed in subjects with heart failure and kidney diseases. Deconvolution of ascitic fluid DNA would be useful to indicate the tissue origin of the pathology. In particular, the identification of the origin of malignancies leading to the ascites. Similar to the analysis of the pleural fluid, methylation deconvolution can be performed on the regions exhibiting various types of genetic aberrations, including copy number aberrations and point mutations, so that the tissue origin of the aberrations can be determined.

VIII. Computer System

Figure 41:
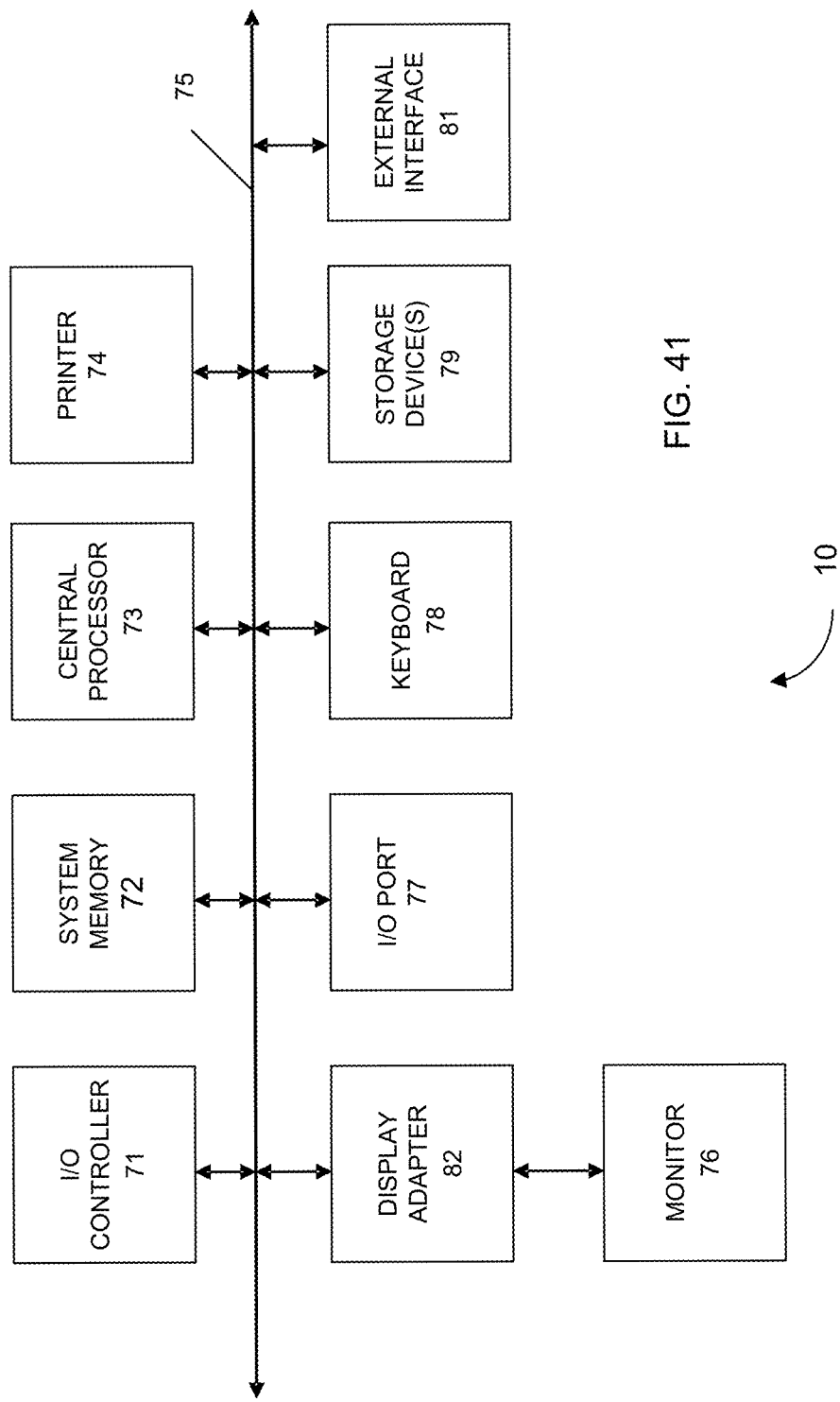
FIG. 41 shows a block diagram of an example computer system 10 usable with system and methods according to embodiments of the present invention.

Any of the computer systems mentioned herein may utilize any suitable number of subsystems. Examples of such subsystems are shown in FIG. 41 in computer apparatus 10. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 41 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive or optical disk), as well as the exchange of information between subsystems. The system memory 72 and/or the storage device(s) 79 may embody a computer readable medium. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned here are incorporated by reference in their entirety for all purposes. None is admitted to be prior art.

What is claimed is:

1. A method of analyzing a biological sample of an organism, the organism being a human suspected of having cancer, the biological sample including a mixture of cell-free DNA molecules from a plurality of tissues types, including a first tissue type, the method comprising:
   analyzing a plurality of cell-free DNA molecules from the biological sample, the plurality of cell-free DNA molecules being at least 1,000 cell-free DNA molecules, wherein analyzing a cell-free DNA molecule includes:
      identifying a location of the cell-free DNA molecule in a reference genome corresponding to the organism;
   identifying a first set of the plurality of cell-free DNA molecules that are each located at any one of N genomic sites of a first chromosomal region of the reference genome corresponding to the organism, N being an integer greater than or equal to 10;
   measuring N first mixture methylation levels at the N genomic sites using the first set of the plurality of cell-free DNA molecules;
   determining, by a computer system, a first fractional contribution of the first tissue type in the mixture using the N first mixture methylation levels;
   identifying a second set of the plurality of cell-free DNA molecules that are each located at any one of K genomic sites of a second chromosomal region of the reference genome corresponding to the organism, K being an integer greater than or equal to 10, wherein the second chromosomal region is different from the first chromosomal region;

measuring K second mixture methylation levels at the K genomic sites using the second set of the plurality of cell-free DNA molecules;

determining, by the computer system, a second fractional contribution of the first tissue type in the mixture using the K second mixture methylation levels;

computing a first separation value between the first fractional contribution and the second fractional contribution;

comparing the first separation value to a threshold value to determine a classification of whether the first tissue type has a sequence imbalance for the first chromosomal region; and outputting, by the computer system, the classification of whether the first tissue type has the sequence imbalance for the first chromosomal region.

2. The method of claim 1, wherein measuring the N first mixture methylation levels at the N genomic sites includes analyzing methylation-aware sequencing results, and wherein the locations of the plurality of cell-free DNA molecules are determined using the methylation-aware sequencing results.

3. The method of claim 1, wherein the organism is pregnant with a fetus, wherein the first tissue type is placental tissue, the method further comprising:
detecting whether the fetus has an aneuploidy in the first chromosomal region based on the classification.

4. The method of claim 1, wherein the organism is pregnant with a fetus, and wherein the first tissue type is not placental tissue.

5. The method of claim 1, wherein the classification is that the first tissue type has the sequence imbalance for the first chromosomal region when the first separation value exceeds the threshold value.

6. The method of claim 5, further comprising:
computing a plurality of separation values for the first tissue type, each of the plurality of separation values corresponding to a different chromosomal region; and
determining a number of the different chromosomal regions having a corresponding separation value that exceeds the threshold value.

7. The method of claim 6, further comprising:
determining the classification of whether the first tissue type has the sequence imbalance for the first chromosomal region based on the number of the different chromosomal regions having a corresponding separation value that exceeds the threshold value.

8. The method of claim 7, wherein the first tissue type is determined to have the sequence imbalance for the first chromosomal region when the number of the different chromosomal regions exceeds a cutoff value.

9. The method of claim 8, wherein the threshold value is dependent on the cutoff value.

10. The method of claim 6, wherein each of the plurality of separation values are computed using the second fractional contribution.

11. The method of claim 6, further comprising:
determining a level of cancer for the first tissue type based on the number of the different chromosomal regions.

12. The method of claim 11, further comprising:
for each of the number of the different chromosomal regions:
determining an extent that the corresponding separation value exceeds the threshold value,
wherein determining the level of cancer for the first tissue type is further based on the extents that the corresponding separation values exceed the threshold values.

13. The method of claim 12, wherein determining the extent that the corresponding separation value exceeds the threshold value includes:
comparing the corresponding separation value to a plurality of threshold values.

14. The method of claim 1, further comprising:
identifying the first chromosomal region as exhibiting a copy number aberration based on a first amount of cell-free DNA molecules that are located in the first chromosomal region; and
determining which of M tissue types is associated with the copy number aberration by testing corresponding separation values in fractional contributions for each of the M tissue types, the first tissue type being one of the M tissue types.

15. The method of claim 14, wherein determining which of the M tissue types is associated with the copy number aberration identifies at least two tissue types as being associated with the copy number aberration by the at least two tissue types each having a corresponding separation value that exceeds the threshold value.

16. The method of claim 15, wherein the first tissue type is one of the at least two tissue types, the method further comprising:
identifying the first tissue type as an origin of primary cancer when the first separation value has a highest value among the corresponding separation values.

17. The method of claim 14, wherein the first chromosomal region exhibits an amplification, the method further comprising:
identifying the second chromosomal region as exhibiting a deletion based on a second amount of cell-free DNA molecules that are located in the second chromosomal region; and
using the second chromosomal region to determine the first separation value based on the second chromosomal region exhibiting of the deletion.

18. The method of claim 1, wherein the first chromosomal region and the second chromosomal region are different chromosomes.

19. The method of claim 1, wherein K does not equal N.

20. The method of claim 1, wherein the first chromosomal region is composed of non-contiguous subregions of a first chromosome for which the sequence imbalance is being tested.

21. The method of claim 1, wherein the second chromosomal region is composed of non-contiguous subregions of one or more reference chromosomes that do not include the first chromosomal region.

22. The method of claim 1, wherein the first chromosomal region exhibits an amplification and wherein the second chromosomal region exhibits a deletion.

23. The method of claim 1, wherein analyzing the plurality of cell-free DNA molecules comprises:
performing methylation-aware sequencing of the plurality of cell-free DNA molecules, including at the N genomic sites of the first chromosomal region and at the K genomic sites of the second chromosomal region, to obtain sequence reads; and
aligning the sequence reads to the reference genome, wherein the N first mixture methylation levels are measured using sequence reads that each aligns to at least one of the N genomic sites of the reference genome, and wherein the K second mixture methylation levels are measured using sequence reads that each aligns to at least one of the K genomic sites of the reference genome.

24. The method of claim 23, wherein the methylation-aware sequencing includes using massively parallel sequencing for whole genome analysis.

25. The method of claim 1, wherein the N first mixture methylation levels form a methylation vector b, and wherein determining the first fractional contribution of the first tissue type includes:
for each of M tissue types:
obtaining N tissue-specific methylation levels at the N genomic sites, N being greater than or equal to M, wherein the N tissue-specific methylation levels form a matrix A of dimensions N by M, the M tissue types including the first tissue type;
solving for a composition vector x that provides the methylation vector b for the matrix A; and
for each of one or more components of the composition vector x:
using the component to determine a corresponding fractional contribution of a corresponding tissue type of the M tissue types in the mixture.

26. The method of claim 1, further comprising:
for each of the first set of the plurality of cell-free DNA molecules:
determining a size of the cell-free DNA molecule;
identifying a first group of the first set of cell-free DNA molecules that have sizes within a first size range;
measuring N third mixture methylation levels at the N genomic sites using the first group of the plurality of cell-free DNA molecules;
determining a third fractional contribution of the first tissue type in the mixture using the N third mixture methylation levels;
identifying a second group of the first set of the plurality of cell-free DNA molecules that have sizes within a second size range, the second size range different than the first size range;
measuring N fourth mixture methylation levels at the N genomic sites using the second group of the plurality of cell-free DNA molecules;
determining a fourth fractional contribution of the first tissue type in the mixture using the N fourth mixture methylation levels;
computing a second separation value between the third fractional contribution and the fourth fractional contribution; and
comparing the second separation value to another threshold value to determine another classification of whether the first tissue type has the sequence imbalance for the first chromosomal region.

27. The method of claim 1, wherein analyzing the plurality of cell-free DNA molecules comprises:
performing methylation-aware sequencing of the plurality of cell-free DNA molecules, including at the N genomic sites of the first chromosomal region and at the K genomic sites of the second chromosomal region, to obtain sequence reads; and
aligning the sequence reads to the reference genome to identify the locations of the cell-free DNA molecules, wherein the N first mixture methylation levels are measured using sequence reads that each aligns to at least one of the N genomic sites of the reference genome, and wherein the K second mixture methylation levels are measured using sequence reads that each aligns to at least one of the K genomic sites of the reference genome,
wherein the N first mixture methylation levels form a methylation vector b, and wherein determining the first fractional contribution of the first tissue type includes:
for each of M tissue types:
obtaining N tissue-specific methylation levels at the N genomic sites, N being greater than or equal to M, wherein the N tissue-specific methylation levels form a matrix A of dimensions N by M, the M tissue types including the first tissue type;
minimizing a cost function including a vector difference between the methylation vector b and a resultant vector of the matrix A operating on a composition vector x to determine the composition vector x that provides the methylation vector b for the matrix A; and
for each of one or more components of the composition vector x:
using the component to determine a corresponding fractional contribution of a corresponding tissue type of the M tissue types in the mixture.

28. The method of claim 1, further comprising:
enriching the biological sample for cell-free DNA molecules that are from the N genomic sites;
enriching the biological sample for cell-free DNA molecules that are from the K genomic sites;
performing methylation-aware sequencing of the cell-free DNA molecules in the enriched biological sample, including at the N genomic sites of the first chromosomal region and at the K genomic sites of the second chromosomal region, to obtain sequence reads; and
aligning the sequence reads to the reference genome to identify the locations of the cell-free DNA molecules, wherein the N first mixture methylation levels are measured using sequence reads that each align to at least one of the N genomic sites of the reference genome, and wherein the K second mixture methylation levels are measured using sequence reads that each aligns to at least one of the K genomic sites of the reference genome.

29. The method of claim 1, wherein the classification is that the first tissue type has the sequence imbalance for the first chromosomal region, the method further comprising:
performing surgery, radiotherapy, or chemotherapy on the organism to treat the first tissue type.

30. The method of claim 1, further comprising:
prior to analyzing the plurality of cell-free DNA molecules, performing a physical separation to filter cell-free DNA molecules that are smaller than a specified cutoff.

31. A computer product comprising a non-transitory computer readable medium storing a plurality of instructions for analyzing a biological sample of an organism, the biological sample including a mixture of cell-free DNA molecules from a plurality of tissues types, including a first tissue type, that when executed on one or more processors of a computer system, cause the computer system to perform:
analyzing a plurality of cell-free DNA molecules from the biological sample, the plurality of cell-free DNA molecules being at least 1,000 cell-free DNA molecules, wherein analyzing a cell-free DNA molecule includes:
identifying a location of the cell-free DNA molecule in a reference genome corresponding to the organism;
identifying a first set of the plurality of cell-free DNA molecules that are each located at any one of N genomic sites of a first chromosomal region of the reference genome corresponding to the organism, N being an integer greater than or equal to 10;

measuring N first mixture methylation levels at the N genomic sites using the first set of the plurality of cell-free DNA molecules;

determining a first fractional contribution of the first tissue type in the mixture using the N first mixture methylation levels;

identifying a second set of the plurality of cell-free DNA molecules that are each located at any one of K genomic sites of a second chromosomal region of the reference genome corresponding to the organism, K being an integer greater than or equal to 10, wherein the second chromosomal region is different from the first chromosomal region;

measuring K second mixture methylation levels at the K genomic sites using the second set of the plurality of cell-free DNA molecules;

determining a second fractional contribution of the first tissue type in the mixture using the K second mixture methylation levels;

computing a first separation value between the first fractional contribution and the second fractional contribution;

comparing the first separation value to a threshold value to determine a classification of whether the first tissue type has a sequence imbalance for the first chromosomal region; and outputting, by the computer system, the classification of whether the first tissue type has the sequence imbalance for the first chromosomal region.

32. The computer product of claim 31, wherein the classification is that the first tissue type has the sequence imbalance for the first chromosomal region when the first separation value exceeds the threshold value.

33. The computer product of claim 32, wherein the plurality of instructions when executed on the one or more processors cause the computer system to further perform:
computing a plurality of separation values for the first tissue type, each of the plurality of separation values corresponding to a different chromosomal region; and
determining a number of the different chromosomal regions having a corresponding separation value that exceeds the threshold value.

34. The computer product of claim 33, wherein the plurality of instructions when executed on the one or more processors cause the computer system to further perform:
determining the classification of whether the first tissue type has the sequence imbalance for the first chromosomal region based on the number of the different chromosomal regions having a corresponding separation value that exceeds the threshold value.

35. The computer product of claim 34, wherein the first tissue type is determined to have the sequence imbalance for the first chromosomal region when the number of the different chromosomal regions exceeds a cutoff value.

36. The computer product of claim 35, wherein the threshold value is dependent on the cutoff value.

37. The computer product of claim 33, wherein each of the plurality of separation values are computed using the second fractional contribution.

38. The computer product of claim 33, wherein the plurality of instructions when executed on the one or more processors cause the computer system to further perform:
determining a level of cancer for the first tissue type based on the number of the different chromosomal regions.

39. The computer product of claim 38, wherein the plurality of instructions when executed on the one or more processors cause the computer system to further perform:
for each of the number of the different chromosomal regions:
determining an extent that the corresponding separation value exceeds the threshold value,
wherein determining the level of cancer for the first tissue type is further based on the extents that the corresponding separation values exceed the threshold values.

40. The computer product of claim 39, wherein determining the extent that the corresponding separation value exceeds the threshold value includes:
comparing the corresponding separation value to a plurality of threshold values.

41. The computer product of claim 31, wherein the plurality of instructions when executed on the one or more processors cause the computer system to further perform:
identifying the first chromosomal region as exhibiting a copy number aberration based on a first amount of cell-free DNA molecules that are located in the first chromosomal region; and
determining which of M tissue types is associated with the copy number aberration by testing corresponding separation values in fractional contributions for each of the M tissue types, the first tissue type being one of the M tissue types.

42. The computer product of claim 41, wherein determining which of the M tissue types is associated with the copy number aberration identifies at least two tissue types as being associated with the copy number aberration by the at least two tissue types each having a corresponding separation value that exceeds the threshold value.

43. The computer product of claim 42, wherein the first tissue type is one of the at least two tissue types, wherein the plurality of instructions when executed on the one or more processors cause the computer system to further perform:
identifying the first tissue type as an origin of primary cancer when the first separation value has a highest value among the corresponding separation values.

44. The computer product of claim 41, wherein the first chromosomal region exhibits an amplification, wherein the plurality of instructions when executed on the one or more processors cause the computer system to further perform:
identifying the second chromosomal region as exhibiting a deletion based on a second amount of cell-free DNA molecules that are located in the second chromosomal region; and
using the second chromosomal region to determine the first separation value based on the second chromosomal region exhibiting of the deletion.

45. The computer product of claim 31, wherein the first chromosomal region exhibits an amplification, and wherein the second chromosomal region exhibits a deletion.

46. The computer product of claim 31, wherein analyzing the plurality of cell-free DNA molecules comprises:
sequencing the plurality of cell-free DNA molecules to obtain sequence reads; and
aligning the sequence reads to the reference genome, wherein the N first mixture methylation levels are measured using sequence reads that each aligns to at least one of the N genomic sites of the reference genome, and wherein the K second mixture methylation levels are measured using sequence reads that each aligns to at least one of the K genomic sites of the reference genome.

47. The computer product of claim 31, wherein the N first mixture methylation levels form a methylation vector b, and wherein determining the first fractional contribution of the first tissue type includes:

for each of M tissue types:
  obtaining N tissue-specific methylation levels at the N genomic sites, N being greater than or equal to M, wherein the N tissue-specific methylation levels form a matrix A of dimensions N by M, the M tissue types including the first tissue type;
  solving for a composition vector x that provides the methylation vector b for the matrix A; and
  for each of one or more components of the composition vector x:
    using the component to determine a corresponding fractional contribution of a corresponding tissue type of the M tissue types in the mixture.

48. The computer product of claim 31, wherein the plurality of instructions when executed on the one or more processors cause the computer system to further perform:
  for each of the first set of the plurality of cell-free DNA molecules:
    determining a size of the cell-free DNA molecule;
  identifying a first group of the first set of cell-free DNA molecules that have sizes within a first size range;
  measuring N third mixture methylation levels at the N genomic sites using the first group of the plurality of cell-free DNA molecules;
  determining a third fractional contribution of the first tissue type in the mixture using the N third mixture methylation levels;
  identifying a second group of the first set of the plurality of cell-free DNA molecules that have sizes within a second size range, the second size range different than the first size range;
  measuring N fourth mixture methylation levels at the N genomic sites using the second group of the plurality of cell-free DNA molecules;
  determining a fourth fractional contribution of the first tissue type in the mixture using the N fourth mixture methylation levels;
  computing a second separation value between the third fractional contribution and the fourth fractional contribution; and
  comparing the second separation value to another threshold value to determine another classification of whether the first tissue type has the sequence imbalance for the first chromosomal region.

* * * * *